US006461586B1

(12) United States Patent
Unger

(10) Patent No.: US 6,461,586 B1
(45) Date of Patent: Oct. 8, 2002

(54) METHOD OF MAGNETIC RESONANCE FOCUSED SURGICAL AND THERAPEUTIC ULTRASOUND

(75) Inventor: Evan C. Unger, Tucson, AZ (US)

(73) Assignee: Imarx Therapeutics, Inc., Tucson, AZ (US)

( * ) Notice: Subject to any disclaimer, the term of this patent is extended or adjusted under 35 U.S.C. 154(b) by 0 days.

(21) Appl. No.: 09/613,210

(22) Filed: Jul. 10, 2000

Related U.S. Application Data

(60) Division of application No. 08/476,317, filed on Jun. 7, 1995, now Pat. No. 6,088,613, and a continuation-in-part of application No. 08/307,305, filed on Sep. 16, 1994, now Pat. No. 5,773,024, and a continuation-in-part of application No. 08/159,687, filed on Nov. 30, 1993, now Pat. No. 5,585,112, which is a continuation-in-part of application No. 08/076,239, filed on Jun. 11, 1993, now Pat. No. 5,469,854, said application No. 08/476,317, is a continuation-in-part of application No. 08/160,232, filed on Nov. 30, 1993, now Pat. No. 5,542,935, which is a continuation-in-part of application No. 08/076,250, filed on Jun. 11, 1993, now Pat. No. 5,580,575, application No. 09/613,210, which is a continuation-in-part of application No. 08/401,974, filed on Mar. 9, 1995, now Pat. No. 5,922,304, which is a continuation-in-part of application No. 08/212,553, filed on Mar. 11, 1994, now abandoned, said application No. 08/076,250, is a continuation-in-part of application No. 07/716,899, filed on Jun. 18, 1991, now abandoned, and a continuation-in-part of application No. 07/717,084, filed on Jun. 18, 1991, now Pat. No. 5,228,446, which is a continuation-in-part of application No. 07/569,828, filed on Aug. 20, 1990, now Pat. No. 5,088,499, which is a continuation-in-part of application No. 07/455,707, filed on Dec. 22, 1989, now abandoned.

(51) Int. Cl.$^7$ .......................... A61B 5/055; A61B 8/00; A61B 5/05

(52) U.S. Cl. ................. 424/9.32; 424/9.321; 424/9.36; 424/9.52; 600/420

(58) Field of Search ..................... 424/9, 9.3, 9.32, 424/9.321, 9.322, 9.33, 9.34, 9.341, 9.35, 9.36, 9.5, 9.51, 9.52, 93; 600/420, 437

(56) References Cited

U.S. PATENT DOCUMENTS

| 3,015,128 | A | 1/1962 | Sommerville et al. ....... 18/2.6 |
| 3,291,843 | A | 12/1966 | Fritz et al. .................. 260/614 |
| 3,293,114 | A | 12/1966 | Kenaga et al. ............. 162/168 |
| 3,479,811 | A | 11/1969 | Walters ....................... 57/153 |
| 3,488,714 | A | 1/1970 | Walters et al. ............. 161/161 |
| 3,532,500 | A | 10/1970 | Priest et al. ................... 96/91 |
| 3,557,294 | A | 1/1971 | Dear et al. ................. 424/342 |
| 3,594,326 | A | 7/1971 | Himmel et al. ............ 252/316 |
| 3,615,972 | A | 10/1971 | Morehouse et al. .......... 156/79 |
| 3,650,831 | A | 3/1972 | Jungermann et al. |
| 3,732,172 | A | 5/1973 | Herbig et al. .............. 252/316 |
| 3,873,564 | A | 3/1975 | Schneider et al. ....... 270/309.6 |
| 3,945,956 | A | 3/1976 | Garner .................... 270/2.5 B |
| 3,960,583 | A | 6/1976 | Netting et al. ............. 106/122 |
| 3,968,203 | A | 7/1976 | Spitzer et al. ................ 424/47 |
| 4,027,007 | A | 5/1977 | Messina ..................... 424/46 |
| 4,089,801 | A | 5/1978 | Schneider ................... 252/316 |
| 4,108,806 | A | 8/1978 | Cohrs et al. ................. 521/54 |
| 4,138,383 | A | 2/1979 | Rembaum et al. ..... 270/29.7 H |
| 4,162,282 | A | 7/1979 | Fulwyler et al. .............. 274/9 |
| 4,179,546 | A | 12/1979 | Garner et al. ................ 521/56 |
| 4,192,859 | A | 3/1980 | Mackaness et al. ............ 424/5 |
| 4,224,179 | A | 9/1980 | Schneider ................... 252/316 |
| 4,229,360 | A | 10/1980 | Schneider et al. .......... 270/403 |
| 4,265,251 | A | 5/1981 | Tickner ...................... 128/660 |
| 4,276,885 | A | 7/1981 | Tickner et al. ............. 128/660 |
| 4,310,505 | A | 1/1982 | Baldeschwieler et al. ...... 424/1 |

(List continued on next page.)

FOREIGN PATENT DOCUMENTS

| AU | 641363 | 3/1990 |
| AU | B-30351/89 | 3/1993 |
| DE | 25 21 003 | 8/1976 |
| DE | 38 03 972 A1 | 8/1989 |
| EP | 0 052 575 | 5/1982 |
| EP | 0 107 559 | 5/1984 |
| EP | 0 077 752 B1 | 3/1986 |
| EP | 0 224 934 A2 | 6/1987 |
| EP | 0 231 091 | 8/1987 |
| EP | 0 243 947 | 11/1987 |
| EP | 0 272 091 | 6/1988 |
| EP | 0 324 938 | 1/1989 |
| EP | 0 320 433 A2 | 6/1989 |
| EP | 0 338 971 | 10/1989 |
| EP | 357163 A1 | 3/1990 |
| EP | 0 359 246 A2 | 3/1990 |
| EP | 0 361 894 | 4/1990 |
| EP | 0 216 730 | 1/1991 |
| EP | 441468 A2 | 8/1991 |
| EP | 0 357 164 B1 | 10/1991 |

(List continued on next page.)

OTHER PUBLICATIONS

Hautanen, A., et al., "Effects of modifications of the RGD sequence and its context on recognition by the fibronectin receptor," *J. Biol. Chem.*, 1989, 264(3), 1437–1442.

Takeuchi, M., et al., "Enhanced visualization of intravascular thrombus with the use of a thrombus targeting ultrasound contrast agent (MRX408): Evidence from in vivo experimental echocardiographic studies," *J. Am. College of Cardiology*, 1998, 81(12), 1 page, Abstract XP–000952675.

Unger, E.C., et al., "In vitrostudies of a new thrombus–specific ultrasound contrast agent," *J. of Cardiology*, 1998, 81(12), 58G–61G, Abstract XP–002087505.

Wu, Y., et al., "Binding and lysing of blood clots using MRX–408," *Investigate Radiology*, 1998, 33(12), 880–885.

(List continued on next page.)

*Primary Examiner*—Russell Travers
*Assistant Examiner*—Lauren Q. Wells
(74) *Attorney, Agent, or Firm*—Woodcock Washburn LLP

(57) ABSTRACT

A novel method for the controlled delivery of therapeutic compounds to a region of a patient, using magnetic resonance focused therapeutic ultrasound, is disclosed.

51 Claims, No Drawings

U.S. PATENT DOCUMENTS

| | | | |
|---|---|---|---|
| 4,310,506 A | 1/1982 | Baldeschwieler et al. ....... | 424/1 |
| 4,315,514 A | 2/1982 | Drewes et al. ............... | 128/653 |
| 4,331,654 A | 5/1982 | Morris ......................... | 424/38 |
| 4,342,826 A | 8/1982 | Cole ............................ | 435/7 |
| 4,344,929 A | 8/1982 | Bonsen et al. ................. | 424/15 |
| 4,420,442 A | 12/1983 | Sands ........................... | 274/13 |
| 4,421,562 A | 12/1983 | Sands et al. ................... | 106/75 |
| 4,426,330 A | 1/1984 | Sears ............................ | 270/403 |
| 4,427,649 A | 1/1984 | Dingle et al. .................. | 424/38 |
| 4,428,924 A | 1/1984 | Millington .................... | 424/4 |
| 4,442,843 A | 4/1984 | Rasor et al. ................... | 128/660 |
| 4,466,442 A | 8/1984 | Hilmann et al. ............... | 128/653 |
| 4,485,193 A | 11/1984 | Rubens et al. ................. | 521/58 |
| 4,530,360 A | 7/1985 | Duarte ......................... | 128/419 F |
| 4,533,254 A | 8/1985 | Cook et al. ................... | 366/176 |
| 4,534,899 A | 8/1985 | Sears ............................ | 270/403 |
| 4,540,629 A | 9/1985 | Sands et al. ................... | 428/402 |
| 4,544,545 A | 10/1985 | Ryan et al. .................... | 424/1.1 |
| 4,549,892 A | 10/1985 | Baker et al. ................... | 65/21.4 |
| 4,569,836 A | 2/1986 | Gordon ........................ | 424/1.1 |
| 4,572,203 A | 2/1986 | Feinstein ..................... | 128/661 |
| 4,586,512 A | 5/1986 | Do-huu et al. ............... | 128/660 |
| 4,603,044 A | 7/1986 | Geho et al. ................... | 424/9 |
| 4,615,879 A | 10/1986 | Runge et al. .................. | 424/9 |
| 4,620,546 A | 11/1986 | Aida et al. .................... | 128/660 |
| 4,621,023 A | 11/1986 | Redziniak et al. ......... | 428/402.2 |
| 4,646,756 A | 3/1987 | Watmough et al. ......... | 128/804 |
| 4,657,756 A | 4/1987 | Rasor et al. ................... | 424/9 |
| 4,658,828 A | 4/1987 | Dory ........................... | 128/660 |
| 4,663,161 A | 5/1987 | Mannino et al. .............. | 424/89 |
| 4,675,310 A | 6/1987 | Chapman et al. .............. | 514/6 |
| 4,681,119 A | 7/1987 | Rasor et al. ................... | 128/660 |
| 4,684,479 A | 8/1987 | D'Arrigo .................... | 252/307 |
| 4,689,986 A | 9/1987 | Carson et al. ................. | 73/19 |
| 4,693,999 A | 9/1987 | Axelsson et al. ............. | 514/174 |
| 4,718,433 A | 1/1988 | Feinstein ..................... | 128/660 |
| 4,728,575 A | 3/1988 | Gamble et al. ........... | 428/402.2 |
| 4,728,578 A | 3/1988 | Higgins et al. .............. | 428/462 |
| 4,731,239 A | 3/1988 | Gordon ........................ | 424/9 |
| 4,737,323 A | 4/1988 | Martin et al. ................. | 274/4.3 |
| 4,774,958 A | 10/1988 | Feinstein ............... | 128/660.01 |
| 4,775,522 A | 10/1988 | Clark, Jr. ..................... | 424/9 |
| 4,776,991 A | 10/1988 | Farmer et al. ............. | 274/4.3 |
| 4,781,871 A | 11/1988 | West, III et al. ............. | 274/4.3 |
| 4,789,501 A | 12/1988 | Day et al. .................... | 252/645 |
| 4,790,891 A | 12/1988 | Halliday et al. ............... | 149/2 |
| 4,822,534 A | 4/1989 | Lencki et al. ................. | 274/4.3 |
| 4,830,858 A | 5/1989 | Payne et al. .................. | 424/450 |
| 4,834,964 A | 5/1989 | Rosen .......................... | 424/9 |
| 4,844,882 A | 7/1989 | Widder et al. ................. | 424/9 |
| 4,863,717 A | 9/1989 | Keana ........................... | 424/9 |
| 4,865,836 A | 9/1989 | Long, Jr. ....................... | 424/5 |
| 4,877,561 A | 10/1989 | Iga et al. ..................... | 274/4.3 |
| 4,893,624 A | 1/1990 | Lele ............................ | 128/399 |
| 4,895,719 A | 1/1990 | Radhakrishnan ............. | 424/45 |
| 4,898,734 A | 2/1990 | Mathiowitz et al. ......... | 424/427 |
| 4,900,540 A | 2/1990 | Ryan et al. ................... | 424/9 |
| 4,918,065 A | 4/1990 | Stindl et al. .................. | 514/179 |
| 4,919,895 A | 4/1990 | Heldebrant et al. ......... | 422/129 |
| 4,921,706 A | 5/1990 | Roberts et al. ............... | 424/450 |
| 4,927,623 A | 5/1990 | Long, Jr. ....................... | 424/5 |
| 4,933,121 A | 6/1990 | Law et al. ................... | 264/4.3 |
| 4,938,947 A | 7/1990 | Nicolau et al. ............... | 424/1.1 |
| 4,957,656 A | 9/1990 | Cerny et al. ................. | 252/311 |
| 4,972,002 A | 11/1990 | Volkert ........................ | 521/120 |
| 4,981,692 A | 1/1991 | Popescu et al. .............. | 424/422 |
| 4,984,573 A | 1/1991 | Leunbach ................... | 128/653 |
| 4,985,550 A | 1/1991 | Charpiot et al. ........... | 536/18.4 |
| 4,987,154 A | 1/1991 | Long, Jr. ...................... | 514/772 |
| 4,993,415 A | 2/1991 | Long ....................... | 128/653 A |
| 4,996,041 A | 2/1991 | Arai et al. ...................... | 424/9 |
| 5,000,960 A | 3/1991 | Wallach ........................ | 424/450 |
| 5,004,611 A | 4/1991 | Leigh ........................... | 424/450 |
| 5,008,050 A | 4/1991 | Cullis et al. .................. | 274/4.3 |
| 5,008,109 A | 4/1991 | Tin .............................. | 424/422 |
| 5,013,556 A | 5/1991 | Woodle et al. ............... | 424/450 |
| 5,019,370 A | 5/1991 | Jay et al. ........................ | 424/4 |
| 5,045,304 A | 9/1991 | Schneider et al. ............. | 424/9 |
| 5,049,388 A | 9/1991 | Knight et al. ................. | 424/450 |
| 4,229,360 A | 11/1991 | Schneider et al. ........... | 270/403 |
| 5,078,994 A | 1/1992 | Nair et al. .................... | 424/501 |
| 5,088,499 A | 2/1992 | Unger ...................... | 128/662.2 |
| 5,107,842 A | 4/1992 | Levene et al. .......... | 128/662.02 |
| 5,114,703 A | 5/1992 | Wolf et al. ..................... | 424/5 |
| 5,123,414 A | 6/1992 | Unger ......................... | 128/654 |
| 5,135,000 A | 8/1992 | Akselrod et al. ....... | 128/662.02 |
| 5,137,928 A | 8/1992 | Erbel et al. ................... | 521/56 |
| 5,141,738 A | 8/1992 | Rasor et al. ................... | 424/2 |
| 5,147,631 A | 9/1992 | Glajch et al. .................. | 424/9 |
| 5,149,319 A | 9/1992 | Unger ........................... | 604/22 |
| 5,171,755 A | 12/1992 | Kaufman ...................... | 514/759 |
| 5,186,922 A | 2/1993 | Shell et al. ................... | 128/654 |
| 5,190,766 A | 3/1993 | Ishihara ...................... | 424/489 |
| 5,190,982 A | 3/1993 | Erbel et al. ................... | 521/56 |
| 5,192,549 A | 3/1993 | Barenolz et al. ............. | 424/450 |
| 5,194,188 A | 3/1993 | Guitierrez ................... | 264/4.1 |
| 5,194,266 A | 3/1993 | Abra et al. .................. | 424/450 |
| 5,195,520 A | 3/1993 | Schlief et al. .......... | 128/660.02 |
| 5,196,183 A | 3/1993 | Yudelson et al. ............... | 424/9 |
| 5,196,348 A | 3/1993 | Schweighardt et al. ...... | 436/173 |
| 5,198,225 A | 3/1993 | Meybeck et al. ............ | 424/450 |
| 5,205,287 A | 4/1993 | Erbel et al. ................. | 128/632 |
| 5,205,290 A | 4/1993 | Unger ...................... | 128/653.4 |
| 5,209,720 A | 5/1993 | Unger ......................... | 604/22 |
| 5,213,804 A | 5/1993 | Martin et al. ................ | 424/450 |
| 5,215,680 A | 6/1993 | D'Arrigo ..................... | 252/307 |
| 5,219,538 A | 6/1993 | Henderson et al. ....... | 428/402.2 |
| 5,228,446 A | 7/1993 | Unger et al. ............ | 128/662.02 |
| 5,230,882 A | 7/1993 | Unger ........................... | 424/9 |
| 5,247,935 A | 9/1993 | Cline et al. ............... | 128/653.2 |
| 5,271,928 A | 12/1993 | Schneider et al. ............. | 424/9 |
| 5,281,408 A | 1/1994 | Unger ........................... | 424/4 |
| 5,283,255 A | 2/1994 | Levy et al. .................... | 514/410 |
| 5,305,757 A | 4/1994 | Unger et al. ............ | 128/662.02 |
| 5,310,540 A | 5/1994 | Giddey et al. ................. | 424/9 |
| 5,315,997 A | 5/1994 | Widder et al. ............ | 128/653.3 |
| 5,315,998 A | 5/1994 | Tachibana et al. ...... | 128/660.01 |
| 5,316,771 A | 5/1994 | Barenholz et al. ........... | 424/450 |
| 5,334,381 A | 8/1994 | Unger ........................... | 424/9 |
| 5,339,814 A | 8/1994 | Lasker ...................... | 128/653.4 |
| 5,344,930 A | 9/1994 | Riess et al. ................... | 544/84 |
| 5,350,571 A | 9/1994 | Kaufman et al. .............. | 424/9 |
| 5,352,435 A | 10/1994 | Unger ........................... | 424/9 |
| 5,354,549 A | 10/1994 | Klaveness et al. .............. | 424/3 |
| 5,358,702 A | 10/1994 | Unger ........................... | 424/9 |
| 5,362,477 A | 11/1994 | Moore et al. ................... | 424/9 |
| 5,362,478 A | 11/1994 | Desai et al. .................... | 424/9 |
| 5,380,411 A | 1/1995 | Schlief .................... | 204/157.15 |
| 5,380,519 A | 1/1995 | Schneider et al. ............. | 424/9 |
| 5,393,524 A | 2/1995 | Quay ............................ | 424/9 |
| 5,409,688 A | 4/1995 | Quay ............................ | 424/9 |
| 5,410,516 A | 4/1995 | Uhlendorf et al. .............. | 367/7 |
| 5,413,774 A | 5/1995 | Schneider et al. .......... | 424/9.51 |
| 5,425,366 A | 6/1995 | Reinhardt et al. ...... | 128/662.02 |
| 5,433,204 A | 7/1995 | Olson ..................... | 128/661.08 |
| 5,445,813 A | 8/1995 | Schneider et al. .......... | 424/9.51 |
| 5,456,900 A | 10/1995 | Unger ......................... | 424/9.4 |
| 5,460,800 A | 10/1995 | Walters ........................ | 429/9.6 |
| 5,469,854 A | 11/1995 | Unger et al. ............ | 128/662.02 |
| 5,470,582 A | 11/1995 | Supersaxo et al. .......... | 424/489 |
| 5,485,839 A | 1/1996 | Aida et al. ............... | 128/653.1 |

| | | | | | | |
|---|---|---|---|---|---|---|
| 5,487,390 A | 1/1996 | Cohen et al. ......... 128/662.02 | | 5,736,121 A | 4/1998 | Unger ....................... 424/9.4 |
| 5,496,535 A | 3/1996 | Kirkland .................... 424/9.37 | | 5,740,807 A | 4/1998 | Porter .................. 128/662.02 |
| 5,498,421 A | 3/1996 | Grinstaff et al. ............ 424/450 | | 5,770,222 A | 6/1998 | Unger et al. ................ 424/450 |
| 5,501,863 A | 3/1996 | Rössling et al. ............ 424/489 | | 5,804,162 A | 9/1998 | Kabalnov et al. .......... 424/9.51 |
| 5,502,094 A | 3/1996 | Moore et al. ................ 524/145 | | 5,830,430 A | 11/1998 | Unger et al. ................ 424/1.21 |
| 5,505,932 A | 4/1996 | Grinstaff et al. ............. 424/9.3 | | 5,840,023 A | 11/1998 | Oraevsky et al. ........... 600/407 |
| 5,508,021 A | 4/1996 | Grinstaff et al. ......... 424/9.322 | | 5,846,517 A | 12/1998 | Unger ....................... 424/9.52 |
| 5,512,268 A | 4/1996 | Grinstaff et al. ............ 424/322 | | 5,849,727 A | 12/1998 | Porter et al. ................ 514/156 |
| 5,527,521 A | 6/1996 | Unger ........................ 424/93 | | 5,855,865 A | 1/1999 | Lambert et al. ........... 424/9.52 |
| 5,529,766 A | 6/1996 | Klaveness et al. ......... 424/9.52 | | 5,858,399 A | 1/1999 | Lanza et al. ................ 424/450 |
| 5,531,980 A | 7/1996 | Schneider et al. ......... 424/9.52 | | 5,874,062 A | 2/1999 | Unger ....................... 424/9.4 |
| 5,536,489 A | 7/1996 | Lohrmann et al. ......... 424/9.52 | | 5,897,851 A | 4/1999 | Quay et al. ................ 424/9.52 |
| 5,536,490 A | 7/1996 | Klaveness et al. ......... 424/9.52 | | 5,928,626 A * | 7/1999 | Klaveness et al. ........... 424/9.3 |
| 5,539,814 A | 7/1996 | Shoji ......................... 379/215 | | 5,976,501 A | 11/1999 | Jablonski ................... 424/9.52 |
| 5,540,909 A | 7/1996 | Schutt ....................... 424/9.52 | | 5,997,898 A | 12/1999 | Unger ....................... 424/450 |
| 5,542,935 A | 8/1996 | Unger et al. ................ 604/190 | | 6,056,938 A | 5/2000 | Unger et al. ................ 424/1.21 |
| 5,545,396 A | 8/1996 | Albert et al. .................. 424/93 | | 6,068,857 A | 5/2000 | Weitschies et al. ......... 424/489 |
| 5,547,656 A | 8/1996 | Unger ........................ 424/9.4 | | 6,159,445 A | 12/2000 | Klaveness et al. ........... 424/9.6 |
| 5,552,133 A | 9/1996 | Lambert et al. ........... 424/9.52 | | 6,261,537 B1 | 7/2001 | Klaveness et al. ......... 424/9.52 |
| 5,552,155 A | 9/1996 | Bailey et al. ................ 424/450 | | 6,331,289 B1 | 12/2001 | Klaveness et al. ......... 424/9.52 |
| 5,556,372 A | 9/1996 | Talish et al. .................... 601/2 | | | | |
| 5,556,610 A | 9/1996 | Yan et al. ................... 424/9.52 | | | | |
| 5,558,092 A | 9/1996 | Unger et al. ............ 128/660.03 | | | | |

FOREIGN PATENT DOCUMENTS

| | | |
|---|---|---|
| EP | 0 458 745 A1 | 11/1991 |
| EP | 0 467 031 A2 | 1/1992 |
| EP | 0 314 764 B1 | 9/1992 |
| EP | 0 554 213 A1 | 8/1993 |
| EP | 0 586 875 | 3/1994 |
| EP | 0 614 656 A1 | 9/1994 |
| EP | 0 633 030 A1 | 1/1995 |
| EP | 0 727 225 A2 | 8/1996 |
| EP | 0 901 793 A1 | 3/1999 |
| FR | 2 700 952 | 8/1994 |
| GB | 1044680 | 10/1966 |
| GB | 2193095 A | 2/1988 |
| JP | 62 286534 | 12/1987 |
| JP | SHO 63-60943 | 3/1988 |
| WO | WO 80/02365 | 11/1980 |
| WO | WO 82/01642 | 5/1982 |
| WO | WO 84/02909 | 8/1984 |
| WO | WO 85/01161 | 3/1985 |
| WO | WO 85/02772 | 7/1985 |
| WO | WO 86/00238 | 1/1986 |
| WO | WO 86/01103 | 2/1986 |
| WO | WO 89/05040 | 6/1989 |
| WO | WO 90/01952 | 3/1990 |
| WO | WO 90/04384 | 5/1990 |
| WO | WO 90/04943 | 5/1990 |
| WO | WO 91/00086 | 1/1991 |
| WO | WO 91/03267 | 3/1991 |
| WO | WO 91/09629 | 7/1991 |
| WO | WO 91/12823 | 9/1991 |
| WO | WO 91/15244 | 10/1991 |
| WO | WO 92/05806 | 4/1992 |
| WO | WO 92/10166 | 6/1992 |
| WO | WO 92/11873 | 7/1992 |
| WO | WO 92/15284 | 9/1992 |
| WO | WO 92/17212 | 10/1992 |
| WO | WO 92/17213 | 10/1992 |
| WO | WO 92/17436 | 10/1992 |
| WO | WO 92/17514 | 10/1992 |
| WO | WO 92/21382 | 12/1992 |
| WO | WO 92/22247 | 12/1992 |
| WO | WO 92/22249 | 12/1992 |
| WO | WO 92/22298 | 12/1992 |
| WO | WO 93/00933 | 1/1993 |
| WO | WO 93/05819 | 1/1993 |
| WO | WO 93/06869 | 4/1993 |
| WO | WO 93/13809 | 7/1993 |
| WO | WO 93/17718 | 9/1993 |
| WO | WO 93/20802 | 10/1993 |
| WO | WO 94/00110 | 1/1994 |

| | | |
|---|---|---|
| 5,558,094 A | 9/1996 | Quay .................... 128/662.02 |
| 5,558,853 A | 9/1996 | Quay ......................... 424/9.5 |
| 5,558,854 A | 9/1996 | Quay ........................ 424/9.52 |
| 5,558,855 A | 9/1996 | Quay ......................... 424/9.5 |
| 5,558,856 A | 9/1996 | Klaveness et al. ......... 424/9.37 |
| 5,560,364 A | 10/1996 | Porter .................... 128/662.02 |
| 5,562,608 A | 10/1996 | Sekins et al. ................. 604/20 |
| 5,562,893 A | 10/1996 | Lohrmann ................. 424/9.52 |
| 5,565,215 A | 10/1996 | Gref et al. .................. 424/501 |
| 5,567,413 A | 10/1996 | Klaveness et al. ......... 424/9.51 |
| 5,567,414 A | 10/1996 | Schneider et al. ......... 424/9.52 |
| 5,567,415 A | 10/1996 | Porter ....................... 424/9.52 |
| 5,567,765 A | 10/1996 | Moore et al. ................ 524/801 |
| 5,569,448 A | 10/1996 | Wong et al. ................ 424/9.45 |
| 5,569,449 A | 10/1996 | Klaveness et al. ......... 424/9.51 |
| 5,571,797 A | 11/1996 | Ohno et al. ................... 514/44 |
| 5,573,751 A | 11/1996 | Quay ........................ 424/9.52 |
| 5,578,292 A | 11/1996 | Schneider et al. ......... 424/9.51 |
| 5,585,112 A | 12/1996 | Unger et al. ................ 424/450 |
| 5,593,680 A | 1/1997 | Bara et al. ................... 424/401 |
| 5,595,723 A | 1/1997 | Quay ......................... 424/9.5 |
| 5,605,673 A | 2/1997 | Schutt et al. ............... 424/9.51 |
| 5,606,973 A | 3/1997 | Lambert et al. ........ 128/662.02 |
| 5,612,057 A | 3/1997 | Lanza et al. ................ 424/450 |
| 5,612,318 A | 3/1997 | Weichselbaum et al. ...... 514/44 |
| 5,614,169 A | 3/1997 | Klaveness et al. ......... 424/9.52 |
| 5,620,689 A | 4/1997 | Allen et al. ............... 424/178.1 |
| 5,626,833 A | 5/1997 | Schutt et al. ............... 424/9.52 |
| 5,637,289 A * | 6/1997 | Klaveness et al. ........... 424/9.3 |
| 5,639,443 A | 6/1997 | Schutt et al. ............... 424/9.52 |
| 5,639,473 A | 6/1997 | Grinstaff et al. ............ 424/450 |
| 5,643,553 A | 7/1997 | Schneider et al. ......... 424/9.52 |
| 5,648,095 A | 7/1997 | Illum et al. ................. 424/489 |
| 5,648,098 A | 7/1997 | Porter ....................... 424/490 |
| 5,672,585 A | 9/1997 | Pierschbacher et al. ....... 514/11 |
| 5,676,928 A | 10/1997 | Klaveness et al. ......... 424/9.32 |
| 5,679,459 A | 10/1997 | Riess et al. ............... 428/402.2 |
| 5,686,060 A | 11/1997 | Schneider et al. ......... 424/9.52 |
| 5,686,102 A | 11/1997 | Gross et al. ................ 424/450 |
| 5,695,460 A | 12/1997 | Siegel et al. .................. 604/21 |
| 5,701,899 A | 12/1997 | Porter .................... 428/662.02 |
| 5,707,352 A | 1/1998 | Sekins et al. ................. 604/56 |
| 5,707,606 A | 1/1998 | Quay ........................ 424/9.52 |
| 5,707,607 A | 1/1998 | Quay ........................ 424/9.52 |
| 5,711,933 A | 1/1998 | Bichon et al. .............. 424/9.52 |
| 5,716,597 A | 2/1998 | Lohrmann et al. ........... 424/9.5 |
| 5,732,707 A | 3/1998 | Widder et al. .......... 128/661.08 |
| 5,733,527 A | 3/1998 | Schutt ...................... 424/9.52 |

| WO | WO 94/06477 | 3/1994 |
| --- | --- | --- |
| WO | WO 94/07539 | 4/1994 |
| WO | WO 94/09829 | 5/1994 |
| WO | WO 94/16739 | 8/1994 |
| WO | WO 94/21301 | 9/1994 |
| WO | WO 94/21302 | 9/1994 |
| WO | WO 94/28780 | 12/1994 |
| WO | WO 94/28873 | 12/1994 |
| WO | WO 95/03835 | 2/1995 |
| WO | WO 95/06518 | 3/1995 |
| WO | WO 95/07072 | 3/1995 |
| WO | WO 95/23615 | 9/1995 |
| WO | WO 95/24184 | 9/1995 |
| WO | WO 95/32005 | 11/1995 |
| WO | WO 96/04018 | 2/1996 |
| WO | WO 96/09793 | 4/1996 |
| WO | WO 96/36286 | 11/1996 |
| WO | WO 96/40281 | 12/1996 |
| WO | WO 96/40285 | 12/1996 |
| WO | WO 98/00172 | 1/1998 |
| WO | WO 99/13919 | 3/1999 |
| WO | WO 99/39738 | 8/1999 |
| WO | WO 01/15742 | 3/2001 |

OTHER PUBLICATIONS

Frezard, F. et al., "Fluorinated phosphatidycholine–based liposomes: H+/ Na + permeability, active doxorubicin encapsulation and stability in human serum," *Biochimica et Biophysica Acta*, 1994, 1194, pp 61–68.

Gross, U. et al., "Phospholipid vesiculated fluorocarbons promising trend in blood substitutes" *Biomat., Art. Cells & Immob. Biotech.*, 1992, vol. 20, (2–4) pp 831–833.

Riess, Jean G., "Fluorine in our arteries", *New J. Chem.*, 1995, vol. 19 (8–9), pp 891–909.

Riess, Jean G., "Introducing a new element fluorine–into the liposomal membrane" *Journal of Liposome Research*, 1995, vol. 5 (3) pp–413–430.

Santaella, C. et al. "Extended in vivo blood circulation time of fluorinated liposomes", *FEBS*, 1993, 336(3), pp 481–484.

Trevino, L, et al., "Incorporation of a perfluoralkylalkane (rfrh) into the phospholipid bilayer of dmpc liposomes results in greater encapsulation stability", *Journal of Liposome Research.*, 1994, vol. 4 (2) pp 1017–1028.

Zarif L. et al., "Biodistribution and excretion of a mixed flurocarbon–hydrocarbon "dowel" emulsion as determined by 19–F NMR", *Artificial Cells, Blood Substitutes, and Immobilization Biotechnology*, 1994, vol. 22,(4) pp 1193–1198.

Porter, T. R., et al., "Thrombolytic Enhancement with Perfluorocarbon–exposed Sonicated Dextrose Albumin Microbubbles", *American Heart Journal*, Nov. 1996, vol. 132, No. 5, pp. 964–968.

Porter, T.R., et al., "Multifold sonicated dilutions of albumin with fifty percent dextrose improve left ventricular contrast videointensity after intravenous injuction in human beings," *J. Am. Soc. Echocardiogr*, XP 000590864, Sep./Oct. 1994, 7(5), 465–471.

Porter, T.R., et al., "Noninvasive identification of acute myocardinal ischemia and reperfusion with contrast ultrasound using intravenous perfluoropropane–exposed sonicated dextrose albumin," *Am. College of Cardiology*, XP 000590865, Jul. 1995, 26(1), 33–40.

Porter, T.R., et al., "Visually discernible myocardial echocardiographic contrast after intravenous injection of sonicated dextrose albumin microbubbles containing high molecular weight, less soluble gases," *Am. College of Cardiology*, Feb. 1995, 25(2), 509–515.

Srinivasan, S.K., et al., "Characerization of binding sites, extent of binding, and drug interactions of oligonucleotides with albumin," *Antisense Res. And Develop.*, 1995, 5, 131–139.

Xie, F., et al., "Acute myocardial ischemia and reperfusion can be visually identified non–invasively with intravenous perfluoropropane–enhanced sonicated dextrose albumin ultrasound contrast," *Circulation*, Oct. 1994, 90(4), Part 2, Abstract 2989, 1 page.

Fitzpatrick, et al., "Metal Ion Catalyzed Decarboxylation: Kinetics and Mechanism of the Oxidative Decarboxylation of Copper (II) Complexes of Aminomalonic Acid in Aqueous Solution", *Inorganic Chemistry*, vol. 13, No. 3, pp. 568–574 (1974).

Thanassi, "Aminomalonic Acid: Spontaneous Decarboxylation and Reaction with 5–Deoxypyridoxal", *Biochemistry*, vol. 9, No. 3, pp. 525–532 (1970).

Stelmashok et al., *Koordinatsionnaya Khimiya*, vol. 3, No. 4, pp. 524–527 (1977) (Russian and English language versions).

Mayhew et al., "High–Pressure Continuous–Flow System for Drug Entrapment in Liposomes", *Methods in Enzymology*, vol. 149, pp. 64–77 (1987).

Mayhew et al., "Characterization of Liposomes Prepared Using a Microemulsifier", *Biochimica et Biophysica Acta*, vol. 775, pp. 169–174 (1984).

Hope et al., "Production of large unilamellar vesicles by a rapid extrusion procedure. Characterization of size distribution, trapped volume, and ability to maintain a membrane potential", *Biochimica et Biophysica Acta*, vol. 812, pp. 55–65 (1985).

Mayer et al., "Vesicles of Variable Size Produced by a Rapid Extrusion Procedure", *Biochemica et Biophysica Acta*, vol. 858, pp. 161–168 (1986).

Cheng et al., "The Production and Evaluation of Contrast–Carrying Liposomes Made with an Automatic High Pressure System", *Investigation Radiology*, vol. 22, No. 1, pp. 47–55 (1987).

Jain, et al., "Facilitated Transport", *Introduction to Biological Membranes*, Ch. 9, pp. 192–231 (J. Wiley and Sons, N.Y. 1980).

Sigel, H., ed., *Metal Ions in Biological Systems: Antibiotics and Their Complexes*, vol. 19 (Marcel Dekker, N.Y. 1985).

Nayar et al., "Generation of Large Unilamellar Vesicles From Long–chain Saturated Phosphatidylcholines by Extrusion Technique", *Biochimica et Biophysica Acta*, vol. 986, pp. 200–206 (1989).

Hope et al., "Generation of Multilamellar and Unilamellar Phospholipid Vesicles", *Chemistry and Physics of Lipids*, vol. 40, pp. 89–107 (1986).

Mattrey et al., "Perfluorochemicals as US Contrast Agents for Tumor Imaging and Hepatosplenography: Preliminary Clinical Results", *Radiology*, vol. 163, No. 2, pp. 339–343 (1987).

Mattrey et al., "Perfluoroctylbromide: A Liver/Spleen–Specific and Tumor–Imaging Ultrasound Contrast Material", *Radiology*, vol. 145, pp. 759–762 (1982).

Keller et al., "Successful Left Ventricular Opacification Following Peripheral Venous Injection of Sonicated Contrast Agent: An Experimental Evaluation", *LV Contrast Echocardiography*, vol. 114, No. 3, pp. 570–575 (1987).
Feinstein et al., "Two–Dimensional Contrast Echocardiography. I. In Vitro Development and Quantitative Analysis of Echo Contrast Agents", *JACC*, vol. 3, No. 1, pp. 14–20 (1984).
Ten Cate et al., "Two–Dimensional Contrast Echocardiography. II: Transpulmonary Studies", *JACC*, vol. 3, No. 1, pp. 21–27 (1984).
Unger et al., "Hepatic Metastases: Liposomal Gd–DTPA–enhanced MR Imaging", *Radiology*, vol. 171, No. 1, pp. 81–85 (1989).
Deamer et al., "Permeability of Lipid Bilayers to Water and Ionic Solutes", *Chemistry and Physics of Lipids*, vol. 40, pp. 167–188 (1986).
Gutknecht et al., "Diffusion of carbon dioxide through lipid bilayer membranes. Effects of carbonic anhydrase, bicarbonate, and unstirred layers", *Chemical Abstracts*, vol. 87, 34772q, p. 136 (1977).
Scarpa et al., "Cation Permeability of Liposomes as a Function of the Chemical Composition of the Lipid Bilayers", *Biochimica et Biophysica Acta*, vol. 241, pp. 789–797 (1971).
MacNaughton et al., "Effects of Gaseous Anaesthetics and Inert Gases on the Phase Transition in Smectic Mesophases of Dipalmitoyl Phosphatidylcholine", *Biochimica et Biophysica Acta*, vol. 597, pp. 193–198 (1980).
Tilcock et al., "Liposomal Gd–DTPA: Preparation and Characterization of Relaxivity", *Radiology*, vol. 171, No. 1, pp. 77–80 (1989).
Mann et al., "Formation of Iron Oxides in Unilamellar Vesicles", *Journal of Colloid and Interface Science*, vol. 122, No. 2, pp. 326–335 (1988).
Anderson et al., "Manganese (III) Complexes in Oxidative Decarboxylation of Acids", *J. Am. Chem. Soc.*, vol. 92, No. 8, pp. 2450–2460 (1970).
Muhlradt et al., "Vitamin B6 Analogs: An Improved Synthesis of 5–Deoxypyridoxal", *New Compounds*, vol. 10, pp. 129–130 (1967).
Chapman, "Physiochemical Properties of Phospholipids and Lipid–Water Systems", *Liposome Technology*, Gregoriadis, G., ed., Chapter 1, vol. 1, pp. 1–18 (CRC Press, Boca Raton, FL, 1984).
Violante et al., "Particulate Suspensions as Ultrasonic Contrast Agents for Liver and Spleen", *Inv. Rad.*, vol. 23, pp. S294–S297, Sep. 1988.
Fritzsch et al., "Preclinical and Clinical Results with an Ultrasonic Contrast Agent", *Inv. Rad.*, vol. 23, pp. S302–S305, Sep. 1988.
Brochure, *Experience*, Sonicator™, Heat Systems–Ultrasonics, Inc. (1987).
M. Ostro, "Liposomes", Marcel Dekker, New York, pp. 102–103 (1983).
Fukuda et al., "Polymer–Encased Vesicles Derived from Dioctadecyldimethylammonium Methacrylate", *J. Am. Chem. Soc.*, vol. 108, pp. 2321–2327 (1986).
Regen, "Polymerized Vesicles", *J. Am. Chem. Soc.*, vol. 102, pp. 6638–6640 (1980).
Rose, A. and Rose, E., "The Condensed Chemical Dictionary", Reinhold Publishing, New York, pp. 728 and 743 (1966).

A.G. Belykh, *Farmakol Toksikol. (MOSC)*, vol. 44(3), pp. 322–326 (1981) (abstract).
J. Vion–Dury et al., *J. Pharmacol. Exper. Ther.*, vol. 250(3), pp. 1113–1118 (1989) (abstract).
M.R. Zalutsky et al., *Invest. Radiol.*, vol. 22(2), pp. 141–147 (1987) (abstract).
Crowe et al., "Preservation of Freeze–Dried Liposomes by Trehalose", *Archives of Biochemistry and Biophysics*, vol. 242, pp. 240–247 (1985).
Crowe et al., "Preservation of Structural and Functional Activity in Lyophilized Sarcoplasmic Reticulum", *Archives of Biochemistry and Biophysics*, vol. 220, pp. 477–484 (1983).
Dorland's Illustrated Medical Dictionary, p. 946, 27th ed. (W.B. Saunders Company, Philadelphia 1988).
*Liposome Technology*, Gregoriadis, G., ed., vol. I, pp. 1–18, 30–35, 51–65 and 79–107 (CRC Press Inc., Boca Raton, FL, 1984).
Madden et al., "The accumulation of drugs within large unilamellar vesicles exhibiting a proton gradient: a survey", *Chemistry and Physics of Lipids*, vol. 53, pp. 37–46 (1990).
Sinkula et al., "Rationale for Design of Biologically Reversible Drug Derivatives: Prodrugs", *J. Pharm. Sci.*, vol. 64, No. 2, pp. 181–210 (1975).
Shiina et al., "Hyperthermia by Low–frequency Synthesized Ultrasound", *IEEE Engineering*, pp. 879–880, vol. 2 (1988) (abstract).
McAvoy et al., *IEEE Engineering, Ultrasonics Symposium Proceedings*, vol. 2, pp. 677–1248 (1989) (abstract).
Chapman et al., "Biomembrane Phase Transitions", *J. Biol. Chem.*, vol. 249, pp. 2512–2521(1974).
Hug et al., "Liposomes for the Transformation of Eukaryotic Cells", *Biochimica et Biophysica Acta*, 1991, 1097:1–17.
Marsh, *CRC Handbook of Lipid Bilayers* (CRC Press, Boca Raton, FL 1990) pp. 139–141.
Szoka et al., "Procedure for preparation of liposomes with large internal aqueous space . . . ", *Proc. Natl. Acad. Sci.*, vol. 75, No. 9, pp. 4194–4198 (1978).
Acoustic Imaging; AI5200; Convex Curved Linear Array Ultrasound Transducers Operator's Manual, Nov. 20, 1989, 4700–0003–1C, p. 4.
Bangham et al., "Diffusion of Univalent Ions across the Lamellae of Swollen Phospholipids", *J. Mol. Biol.*, 1965, 13:238–252.
Carson et al., "Ultrasound Power and Intensitites Produced By Diagnostic Ultrasound Equipment", *Ultrasound in Med. & Biol.*, vol. 3, pp. 341–350 (1978).
Kost et al., *Polymers in Medicine II: Biomedical and Pharmaceutical Applications*, "Ultrasonic Modulated Drug Delivery Systems", Chiellini et al., eds., (Plenum Press, New York and London), pp. 387–396 (1985).
deGier et al., "Relations Between Liposomes and Biomembranes", *Annals of New York Academy of Sciences*, vol. 308, pp. 85–99 (1978).
Felgner et al., "Lipofection: A highly efficient, lipid–mediated DNA–transfection procedure", *Proc. Natl. Acad. Sci.*, vol. 84, pp. 7413–7417 (1987).
Gabizon et al., "Liposome formulations with prolonged circulation time in blood and enhanced uptake by tumors", *Proc. Natl. Acad. Sci.*, vol. 85, pp. 6949–6953 (1988).
Garelli, et al., "Incorporation of new amphiphilic perfluoroalkylated bypyridine platinum and palladium complexes into liposomes: stability and . . . " *Biochimica et Biophysica Acta*, vol. 1127, pp. 41–48 (1992).

Kawai et al., "New Procedure for DNA Transfection with Polycation and Dimethyl Sulfoxide", *Molecular and Cellular Biology*, vol. 4, No. 6, pp. 1172–1174 (1984).

Kuo et al., "Metallocene Antitumor Agents. Solution and Solid–State Molybdenocene Coordination . . . ", *J. Am. Chem. Soc.*, vol. 113, No. 24, pp. 9027–9045 (1991).

MacDonald, *Mammalian Cell Biotechnology: A Practical Approach*, M. Butler, ed., (Oxford University Press, New York), Chapter 4, pp. 57–70 (1991).

Mathiowitz et al., "Photochemical Rupture of Microcapsules: A Model System", *Journal of Applied Polymer Science*, vol. 26, pp. 809–822 (1981).

May et al., "Cationic Liposomes Enable Bovine Herpesvirus Type 2 DNA to Infect Cells", *Acta virol.*, 1991, 35:107.

Poznansky et al., "Biological Approaches to the Controlled Delivery of Drugs: A Critical Review", *Pharmacol. Rev.*, vol. 36, No. 4, pp. 277–336 (1984).

Sato et al., "Recent Aspects In The Use Of Liposomes In Biotechnology And Medicine", *Prog. Lipid Res.*, vol. 31, No. 4, pp. 345–372 (1992).

Simons et al., "Antisense c–myb oligonucleotides inhibit intimal arterial smooth muscle cell accumulation in vivo", *Nature*, vol. 359, pp. 67–70 (1992).

Thompson,"At Age 2, Gene Therapy Enters a Growth Phase", *Science*, vol. 258, pp. 744–746 (1992).

Trubetskoy et al., "Cationic liposomes enhance targeted delivery and expression of exogenous DNA . . . ", *Biochimica et Biophysica Acta*, vol. 1131, pp. 311–313 (1992).

Umemura et al., "Studies on Sonodynamic Cancer Therapy", *IEEE*, O–7803–0785, pp. 354–355 (1992).

Williams, "Human Gene Therapy: Searching for Better Vectors", *ASM News [American Society for Microbiology]* vol. 58, pp. 67–69 (1992).

Woodle et al., "Versatility in lipid compositions showing prolonged circulation . . . ", *Biochimica et Biophysica Acta* 1992, 1105:193–200.

Zhou et al., "Targeted delivery of DNA by liposomes and polymers", *J. of Controlled Release*, vol. 19, pp. 269–274 (1992).

Mathiowitz et al., "Polyanhydride Microspheres as Drug Carriers. II. Microencapsulation by Solvent Removal", *Journal of Applied Polymer Science*, vol. 35, pp. 755–774 (1988).

Sankaram et al., "Cholesterol–Induced Fluid–Phase Immiscibility in Membranes", *Proc. Natl. Acad. Sci.*, vol. 88, pp. 8686–8690 (1991).

*Scientific Apparatus Catalog 92/93* (VWR Scientific, 1991), "Syringes", pp. 1511–1513; "Filtration, Syringe Filters", pp. 766–768; "Filtration, Membranes", pp. 750–753; "Filtration, Filter Holders", p. 744.

Gramiak et al., "Detection of Intracardiac Blood Flow by Pulsed Echo–Ranging", *Radiology*, vol. 100, pp. 415–418 (1971).

Feigenbaum et al., *Circulation*, "Identification of Ultrasound Echoes from the Left Ventricle by Use on Intracardiac Injections of Indocyanine Green", vol. XL1, pp. 615–621, Apr. 1970.

Santaella, et al., "Extended In Vivo Blood Circulation Time of Fluorinated Liposomes", *FEBS 13463*, vol. 336, No. 3, pp. 481–484 (1993).

Brown and Langer, *Annual Review Medicine*, 1988, 39:221 29, Annual Review, Inc., "Transdermal Delivery of Drugs", pp. 221–229.

Moseley, et al., *Microbubbles: A Novel MR Susceptibility Contrast Agent*, abstract, 1991 Napa, California Meeting of the Society for Magnetic Resonance in Medicine.

Ter–Pogossian, "Physical Principles and Instrumentation", *Computed Body Tomography*, Lee, et al., eds., Raven Press, New York, Chapter 1, pp. 1–7 (1988).

Aronberg, "Techniques", *Computed Body Tomograhy*, Lee, et al., eds., Raven Press, New York, Chapter 2, pp. 9–36 (1988).

Miller, *Ultrasonics* (Sep. 1981), "Ultrasonic detection of resonant cavitation bubbles in a flow tube by their second–harmonic emissions," pp. 217–224.

Dittrich, "Cardiac Muscle Ischemia and Infarction", *The Second Annual International Symposium on Contrast Agents in Diagnostic Ultrasound*, Atlantic City, NJ (May 7, 1996) (abstract).

Pantely, "Intravenous Contrast Echocardiography–Tissue Imaging & Quatification of Coronary Blood Flow", *The Second Annual International Symposium on Contrast Agents in Diagnostic Ultrasound*, Atlantic City, NJ (May 7, 1996) (abstract).

Schutt et al., "Osmotically Stabilized Microbubble Sonographic Contrast Agents",*Acad. Radiol.*, vol. 3, Suppl. 2, pp. S188–S190 (Aug. 1996).

Frézard, et al., "Permeability and stability in buffer and in human serum of fluorinated phospholipid–based liposomes", *Biochimica et Biophysica Acta*, 1192, pp. 61–70 (1994).

Frézard, et al., "Fluorinated Phospholipid–Based Vesicles as Potential Drug Carriers: Encapsulation/Sustaining of Drugs and Stability in Human Serum", *Art, Cells, Blood Subs., and Immob. Biotech.*, 22(4), pp. 1403–1408 (1994).

Chang, "Semipermeable Aqueous Microcapsules", *Canadian J. Of Phys. And Pharm.*, 1966, vol. 44, pp. 115–128 (1978).

Chang, "Semipermeable Microcapsules", *Science*, 1964, 146, 524–525.

Deasy, Microencapsulation and Related Drug Processes, vol. 20, Chs. 9 and 10, pp. 195–239 (1983) (Marcel Dekker, Inc., NY).

Yeung et al., "Preparation of Microencapsulated Liposomes", *J. Microencapsulation*, 1988, 5, 331–337.

Mattrey et al., *Gas Emulsions as Ultrasound Contrast Agents; Preliminary Results in Rabbits and Dogs*, *Investigative Radiology*, vol. 29, Jun. Supp. 2, pp. S139–S141, 1994.

Meltzer et al., *Transmission of Ultrasonic Contrast Through the Lungs*, Ultrasound in Med. & Biol., vol. 7, No. 4, 377–384, 1981.

PR Newswire, Apr. 1, 1986.

Swanson et al., "Enhancement Agents for Ultrasound: Fundamentals", *Pharmaceuticals In Medical Imaging*, Chapter 22, pp. 682–687 (1990).

Ophir et al., "Contrast Agents in Diagnostic Ultrasound", *Ultrasound in Med. & Biol*, vol. 15, No. 4, pp. 319–333 (1989).

Jacobs, "Intraocular gas measurement using A–scan ultrasound", *Current Eye Research*, vol. 5, No. 8, pp. 575–578 (1986).

Lincoff et al., "Intravitreal Expansion of Perfluorocarbon Bubbles", *Arch Ophthalmol.*, vol. 98, p. 1646, Sep. 1980.

Lincoff et al., "Intravitreal Longevity of Three Perflurocarbon Gases", *Arch. Ophthalmol.*, vol. 98, pp. 1610–1611, Sep. 1980.

Lincoff et al., "The Perfluorocarbon Gases in the Treatment of Retinal Detachment", *Ophthalmology*, vol. 90, No. 5, pp. 546–551, May 1983.

Gardner et al., "A Survey of Intraocular Gas Use in North America", *Arch. Ophthalmol.*, vol. 106, pp. 1188–1189, Sep. 1988.

Unger et al., "Liposomal MR Contrast Agents", *J. Liposome Research*, 4(2), pp. 811–834 (1994).

Feinstein, Steven B., "Myocardial Perfusion Imaging: Contrast Echocardiography Today and Tomorrow," *Journal of the American College of Cardiology*, 8(1):251–253 (1986).

Keller et al., "The Behavior of Sonicated Albumini Microbubbles Within the Microcirculation: A Basis for Their Use During Myocardial Contrast Echocardiography", *Circulation Res,*, vol. 65, No. 2, pp. 458–467 (Aug. 1989).

Lincoff et al., "Perfluoro–n–butane: A Gas for Maximum Duration Retinal Tamponade," *Arch Ophthalmology*, 101:460–462 (1983).

*Remington's Pharmaceutical Sciences*, John Hoover, managing ed., Mack Publishing Company, Easton, PA, pp. 295–298; 736; 1242–1244 (1975).

*Handbook of Pharmaceutical Excipients*, American Pharmaceutical Association, Washington, D.C. and The Pharmaceutical Society of Great Britain, London, England, pp. 181–183 (1986).

Barnhart et al., "Characteristics of Albunex™: Air–Filled Microspheres for Echocardiography Contrast Enhancement," *Investigative Radiology*, 25:S162–164 (Sep. 1990).

Levene et al., "Characterization of Albunex™," *J. Acoust. Soc. Am.*, 87 (Suppl. 1):569–70 (Spring 1990).

Miller et al., "Physiochemical Approaches to the Mode of Action of General Anesthetics," *J. Amer. Soc. Anesthesiologists*, 36(4):339–351 (1972).

"Properties and Applications of the 'Freon' Fluorocarbons" in DuPont Freon Technical Bulletin B–2 (E.I. DuPont de Nemours and Company, Wilmington, DE), pp. 1–11 (1964).

"'Freon' Fluorocarbons: Properties and Applications" in DuPont Technical Bulletin G–1 (E.I. DuPont de Nemours and Company, Wilmington, DE), pp. 1–10 (1987).

"Encyclopedia of Polymer Science and Engineering," John Wiley & Sons, New York, 1:164–169 (1985).

"Concise Encyclopedia of Polymer Science and Engineering," J. Kroschwitz, ed., John Wiley & Sons, New York, pp. 12–13 (1990).

Wheatley et al., "Contrast Agents for Diagnostic Ultrasound: Development and Evaluation of Polymer–Coated Microbubbles," *Biomaterials*, 11:713–717 (1990).

Villaneuva et al., "Characterization of Spatial Patterns of Flow Within the Reperfused Myocardium by Myocardial Contrast Echocardiography", *Circulation*, vol. 88, No. 6, pp. 2596–2606 (Dec. 1993).

Desir et al., "Assessment of regional myocardial perfusion with myocardial contrast echocardiography in a canine model of varying degrees of coronary stenosis", *American Heart Journal*, vol. 127, No. 1, pp. 56–63 (Jan. 1994).

Sekins et al., "Lung Cancer Hyperthermia via Ultrasound and PFC Liquids", *Published in Proceedings of 5th International Symposium on Hyperthermic Oncology*, Kyoto, Japan, (3 pages) (Aug. 29–Sep. 3, 1998).

Pietersen, "A New Warning System for Fires of Electrical Origin", *CERN European Organization for Nuclear Research, Health and Safety Division*, pp. 1–5 (Mar. 1977).

Nomura et al., "US Contrast Enhancement of Hepatic Tumor with Helium Gas Microbubbles: A Preliminary Report", *Jpn. J. Med. Ultrasonics*, vol. 18, No. 5 (1991) (Japanese with English language abstract).

Lindner et al., "Myocardial Perfusion Characteristics and Hemodynamic Profile of MRX–115, a Venous Echocardiographic Contrast Agent, During Acute Myocardial Infarction," *J. Am. Soc. of Echocardiography*, vol. 11, No. 1, pp. 36–46 (Jan. 1998).

Regen et al., "Polymerized Phosphatidylcholine Vesicles. Synthesis and Characterization," *J. Am. Chem. Soc.*, vol. 104, No. 3, pp. 191–195 (1982).

Wei et al., "Quantification of Myocardial Blood Flow With Ultrasound–Induced Destruction of Microbubbles Administered as a Constant Venous Infusion," *Circulation*, vol. 97, pp. 473–483 (1998).

Hynynen et al., "The Usefulness of a Contrast Agent and Gradient–Recalled Acquisition in a Steady–State Imaging Sequence for Magnetic Resonance Imaging–Guided Noninvasive Ultrasound Surgery," *Investigative Radiology*, vol. 29, pp. 897–903 (Oct. 1994).

Lejbkowicz et al., "The response of normal and malignant cells to ultrasound in vitro." Database *BIOSIS*, No. 1993:95122245 (abstract only).

Jackson et al., "Effect of ultrasound therapy on the repair of Achilles tendon injuries in rats." *Medicine And Science In Sports And Exercise*, vol. 23, No. 2, pp. 171–176, 1991.

Maxwell, "Therapeutic Ultrasound: Its Effects on the Cellular and Molecular Mechanisms of Inflammation and Repair." *Physiotherapy*, vol. 78, No. 6, pp. 421–426, Jun. 1992.

Tuncay et al., "Expression of Genes Associated with Tissue Remodeling Upon Ultrasound Perturbation in the Gingival Fibroblast." *Journal of Dental Research*, vol. 75, p. 143, 1996 (abstract only).

Wang et al., "Low Intensity Ultrasound Treatment Increases Strength in a Rat Femoral Fracture Model." *Journal of Orthopaedic Research*, vol. 12, No. 1, pp. 40–47, 1994.

Yang et al., "Exposure to Low–Intensity Ultrasound Increases Aggrecan Gene Expression in a Rat Femur Fracture Model." *Journal of Orthopaedic Research*, vol. 14, No. 5, pp. 802–809, 1996.

Young et al., "Effect of therapeutic ultrasound on the healing of full–thickness excised skin lesions." *Ultrasonics*, vol. 28, No. 3, pp. 175–180, 1990.

Young et al., "The Effect of Therapeutic Ultrasound On Angiogenesis." *Ultrasound in Medicine and Biology*, vol. 16, No. 3, pp. 261–269, 1990.

Chortkoff et al., "Pharmacokinetics Do Not Explain the Absence of an Anesthetic Effect of Perfluoropropane or Perfluoropentane." *Anesth. Analg.*, 79, pp. 234–237, 1994.

Sharma et al., "Emulsification Methods For Perfluorochemicals." *Drug Development And Industrial Pharmacy*, 14 (15–17), pp. 2371–2376 (1988).

Tilcock et al., "PEG–coated Lipid Vesicles with Encapsulated Technetium–99m as Blood Pool Agents for Nuclear Medicine." *2211b Nuclear Medicine and Biology*, 21, No. 2, pp. 165–170, 1994.

Tilcock et al., "$^{99m}$Tc–labeling of Lipid Vesicles Containing the Lipophilic Chelator PE–DTTA: Effect of Tin–to–chelate Ratio, Chelate Content and Surface Polymer on Labeling Efficiency and Biodistribution Behavior." *2211b Nuclear Medicine and Biology*, 21, No. 1, pp. 89–96, 1994.

Zarif et al., "Synergistic Stabilization of Perfluorocarbon–Pluronic F–68 Emulsion by Perfluoroalkylated Polyhydroxylated Surfactants." *JAOCS*, vol. 66, No. 10, pp. 1515–1523, 1989.

Ding et al., *Chung Kuo Yao Li Hsueh Pao*, 1989 Sep.; 10(5):473–5 (Abstract only).

P.N.T. Wells, "Pulse–Echo Methods", *Biomedical Ultrasonics*, Academic Press, pp. 209–220 (1977).

Robinson, et al., F.J. Fry, ed., *Ultrasound: Its Applications In Medicine And Biology*, Elsevier Scientific Publishing Company, vol. 3, Chap. XI, pp. 593–596 (1978).

Kinsler, et al., *Fundamentals of Acoustics*, third ed., pp. 228–331 (1982).

* cited by examiner

METHOD OF MAGNETIC RESONANCE FOCUSED SURGICAL AND THERAPEUTIC ULTRASOUND

REFERENCE TO COPENDING APPLICATIONS

This application is a divisional of application Ser. No. 08/476,317, filed Jun. 7, 1995, now U.S. Pat. No. 6,088,613.

This application is a continuation-in-part of copending application Ser. No. 08/401,974, filed Mar. 9, 1995, now U.S. Pat. No. 5,922,304, which is a continuation-in-part of copending application Ser. No. 08/212,553, filed Mar. 11, 1994 now abandoned, the disclosures of which are hereby incorporated herein by reference, in their entirety, and priority to which is hereby claimed.

This application is also a continuation-in-part of copending application Ser. No. 08/076,250, filed Jun. 11, 1993, now U.S. Pat. No. 5,580,575 which is a continuation-in-part of U.S. Ser. No. 07/716,899 now abandoned, and U.S. Ser. No. 07/717,084, now U.S. Pat. No. 5,228,446, each filed Jun. 18, 1991, which in turn are continuations-in-part of U.S. Ser. No. 07/569,828, filed Aug. 20, 1990, now U.S. Pat. No. 5,088,499 which in turn is a continuation-in-part of U.S. Ser. No. 07/455,707, filed Dec. 22, 1989, now abandoned discloses therapeutic drug delivery systems comprising gas filled microspheres containing a therapeutic agent, with particular emphasis on the use of ultrasound techniques to monitor and determine the presence of said microspheres in a patient's body, and then to rupture said microspheres in order to release said therapeutic agent in the region of the patient's body where said microspheres are found.

This application is also a continuation-in-part of copending application Ser. No. 08/076,239, filed Jun. 11, 1993, now U.S. Pat. No. 5,469,854 which has the identical parentage of preceding applications as Ser. No. 08/076,250 set out immediately above, discloses methods and apparatus for preparing gas filled microspheres suitable for use as contrast agents for ultrasonic imaging or as drug delivery agents.

This application is also a continuation-in-part of copending applications Ser. No. 08/307,305, filed Sep. 16, 1994, now U.S. Pat. No. 5,773,024 and copending applications Ser. No. 08/159,687 now U.S. Pat. No. 5,585,112, and Ser. No. 08/160,232, now U.S. Pat. No. 5,542,935 both of which were filed Nov. 30, 1993, which in turn are continuation-in-parts, respectively, of applications Ser. No. 08/076,239, now U.S. Pat. No. 5,469,854, and U.S. Ser. No. 08/076,250, now U.S. Pat. No. 5,580,575, both of which were filed Jun. 11, 1993, disclose novel therapeutic delivery systems and methods of preparing gas and gaseous precursor filled microspheres and multiphase lipid and gas compositions useful in diagnostic and therapeutic applications.

Benefit of the filing dates of applications Ser. Nos. 08/307,305, 08/159,687, 08/160,232, 08/076,239 and 08/076,250, and their parentage, is hereby claimed, and they are incorporated herein by reference in their entirety.

Reference is also made to application Ser. No. 07/507,125, filed Apr. 10, 1990 now abandoned, which discloses the use of biocompatible polymers, either alone or in admixture with one or more contrast agents such as paramagnetic, superparamagnetic or proton density contrast agents. The polymers or polymer/contrast agent admixtures may optionally be admixed with one or more biocompatible gases to increase the relaxivity of the resultant preparation.

BACKGROUND OF THE INVENTION

1. Field of the Invention

This invention relates to the field of magnetic resonance imaging, more specifically to the use of stabilized gas filled vesicles as contrast media for magnetic resonance imaging (MRI) directed ultrasound surgery.

There are a variety of imaging techniques that have been used to diagnose disease in humans. One of the first imaging techniques employed was X-rays. In X-rays, the images produced of the patients' body reflect the different densities of body structures. To improve the diagnostic utility of this imaging technique, contrast agents are employed to increase the density of tissues of interest as compared to surrounding tissues to make the tissues of interest more visible on X-ray. Barium and iodinated contrast media, for example, are used extensively for X-ray gastrointestinal studies to visualize the esophagus, stomach, intestines and rectum. Likewise, these contrast agents are used for X-ray computed tomographic studies (that is, computer assisted tomography or CAT) to improve visualization of the gastrointestinal tract and to provide, for example, a contrast between the tract and the structures adjacent to it, such as the vessels or lymph nodes. Such contrast agents permit one to increase the density inside the esophagus, stomach, intestines and rectum, and allow differentiation of the gastrointestinal system from surrounding structures.

Magnetic resonance imaging (MRI) is a relatively new imaging technique which, unlike X-rays, does not utilize ionizing radiation. Like computer assisted tomography (CAT), MRI can make cross-sectional images of the body, however MRI has the additional advantage of being able to make images in any scan plane (i.e., axial, coronal, sagittal or orthogonal). Unfortunately, the full utility of MRI as a diagnostic modality for the body is hampered by the need for new or better contrast agents. Without suitable agents, it is often difficult using MRI to differentiate the target tissue from adjacent tissues. If better contrast agents were available, the overall usefulness of MRI as an imaging tool would improve, and the diagnostic accuracy of this modality would be greatly enhanced.

MRI employs a magnetic field, radio frequency energy and magnetic field gradients to make images of the body. The contrast or signal intensity differences between tissues mainly reflect the T1 (longitudinal) and T2 (transverse) relaxation values and the proton density (effectively, the free water content) of the tissues. In changing the signal intensity in a region of a patient by the use of a contrast medium, several possible approaches are available. For example, a contrast medium could be designed to change either the T1, the T2 or the proton density.

2. Brief Description of the Prior Art

In the past, attention has mainly been focused on paramagnetic contrast media for MRI. Paramagnetic contrast agents contain unpaired electrons which act as small local magnets within the main magnetic field to increase the rate of longitudinal (T1) and transverse (T2) relaxation. Most paramagnetic contrast agents are metal ions which in most cases are toxic. In order to decrease toxicity, these metal ions are generally chelated using ligands. The resultant paramagnetic metal ion complexes have decreased toxicity. Metal oxides, most notably iron oxides, have also been tested as MRI contrast agents. While small particles of iron oxide, e.g., under 20 nm diameter, may have paramagnetic relaxation properties, their predominant effect is through bulk susceptibility. Therefore magnetic particles have their predominant effect on T2 relaxation. Nitroxides are another class of MRI contrast agent which are also paramagnetic. These have relatively low relaxivity and are generally less effective than paramagnetic ions as MRI contrast agents. All of these contrast agents can suffer from some toxic effects in certain use contexts and none of them are ideal for use as perfusion contrast agents by themselves.

The existing MRI contrast agents suffer from a number of limitations. For example, positive contrast agents are known to exhibit increased image noise arising from intrinsic peristaltic motions and motions from respiration or cardiovascular action. Positive contrast agents such as Gd-DTPA are subject to the further complication that the signal intensity depends upon the concentration of the agent as well as the pulse sequence used. Absorption of contrast agent from the gastrointestinal tract, for example, complicates interpretation of the images, particularly in the distal portion of the small intestine, unless sufficiently high concentrations of the paramagnetic species are used (Kornmesser et al., *Magn. Reson. Imaging*, 6:124 (1988)). Negative contrast agents, by comparison, are less sensitive to variation in pulse sequence and provide more consistent contrast. However at high concentrations, particulates such as ferrites can cause magnetic susceptibility artifacts which are particularly evident, for example, in the colon where the absorption of intestinal fluid occurs and the superparamagnetic material may be concentrated. Negative contrast agents typically exhibit superior contrast to fat, however on T1-weighted images, positive contrast agents exhibit superior contrast versus normal tissue. Since most pathological tissues exhibit longer T1 and T2 than normal tissue, they will appear dark on T1-weighted and bright on T2-weighted images. This would indicate that an ideal contrast agent should appear bright on T1-weighted images and dark on T2-weighted images. Many of the currently available MRI contrast media fail to meet these dual criteria.

Toxicity is another problem with the existing contrast agents. With any drug there is some toxicity, the toxicity generally being dose related. With the ferrites there are often symptoms of nausea after oral administration, as well as flatulence and a transient rise in serum iron. The paramagnetic contrast agent Gd-DTPA is an organometallic complex of gadolinium coupled with the complexing agent diethylene triamine pentaacetic acid. Without coupling, the free gadolinium ion is highly toxic. Furthermore, the peculiarities of the gastrointestinal tract, for example, wherein the stomach secretes acids and the intestines release alkalines, raise the possibility of decoupling and separation of the free gadolinium or other paramagnetic agent from the complex as a result of these changes in pH during gastrointestinal use. Certainly, minimizing the dose of paramagnetic agents is important for minimizing any potential toxic effects.

New and/or better contrast agents useful in magnetic resonance imaging as well as improved imaging techniques are needed. The present invention is directed, inter alia, to these important ends.

In the work on MRI contrast agents described above for application Ser. No. 07/507,125, filed Apr. 10, 1990, it has been disclosed how gas can be used in combination with polymer compositions and paramagnetic or superparamagnetic agents as MRI contrast agents. Therein it has been shown how the gas stabilized by said polymers would function as an effective susceptibility contrast agent to decrease signal intensity on T2 weighted images; and that such systems are particularly effective for use as gastrointestinal MRI contrast media.

Widder et al. published application EP-A-0 324 938 discloses stabilized microbubble-type ultrasonic imaging agents produced from heat-denaturable biocompatible protein, e.g., albumin, hemoglobin, and collagen.

There is also mentioned a presentation believed to have been made by Moseley et al., at a 1991 Napa, Calif. meeting of the Society for Magnetic Resonance in Medicine, which is summarized in an abstract entitled "Microbubbles: A Novel MR Susceptibility Contrast Agent." The microbubbles which are utilized comprise air coated with a shell of human albumin. The stabilized gas filled vesicles of the present invention are not suggested.

For intravascular use, however, the inventors have found that for optimal results, it is advantageous that any gas be stabilized with flexible compounds. Proteins such as albumin may be used to stabilize the bubbles but the resulting bubble shells may be brittle and inflexible. This is undesirable for several reasons. Firstly, a brittle coating limits the capability of the bubble to expand and collapse. As the bubble encounters different pressure regions within the body (e.g., moving from the venous system into the arteries upon circulation through the heart) a brittle shell may break and the gas will be lost. This limits the effective period of time for which useful contrast can be obtained in vivo from the bubbles contrast agents. Also such brittle, broken fragments can be potentially toxic. Additionally the inflexible nature of brittle coatings such as albumin, and stiff resulting bubbles make it extremely difficult to measure pressure in vivo.

Quay published application WO 93/05819 discloses that gases with high Q numbers are ideal for forming stable gases, but the disclosure is limited to stable gases, rather than their stabilization and encapsulation, as in the present invention. In a preferred embodiment described on page 31, sorbitol is used to increase viscosity, which in turn is said to extend the life of a microbubble in solution. Also, it is not an essential requirement of the present invention that the gas involved have a certain Q number or diffusibility factor.

Lanza et al. published application WO 93/20802 discloses acoustically reflective oligolamellar liposomes, which are multilamellar liposomes with increased aqueous space between bilayers or have liposomes nested within bilayers in a nonconcentric fashion, and thus contain internally separated bilayers. Their use as ultrasonic contrast agents to enhance ultrasonic imaging, and in monitoring a drug delivered in a liposome administered to a patient, is also described.

D'Arrigo U.S. Pat. Nos. 4,684,479 and 5,215,680 disclose gas-in-liquid emulsions and lipid-coated microbubbles, respectively.

In accordance with the present invention it has been discovered that stabilized gas filled vesicles are extremely effective, non-toxic contrast agents for simultaneous magnetic resonance focused noninvasive ultrasound.

SUMMARY OF THE INVENTION

The present invention is directed to a method of magnetic resonance imaging focused surgical and therapeutic ultrasound comprising administering a contrast medium for magnetic resonance imaging comprising gas filled vesicles to a patient requiring surgery, using said contrast medium to scan the patient with magnetic resonance imaging to identify the region of the patient requiring surgery, and applying ultrasound to the region to carry out surgery. The application of ultrasound may be followed by a second scanning step whereby the patient is scanned with magnetic resonance imaging. The ultrasound application may be simultaneous with magnetic resonance imaging. The scanning and surgical ultrasound steps may be performed repeatedly until the desired effect is achieved. The gas filled vesicles may comprise a therapeutic which may be released to a localized region of a patient upon ultrasound.

In addition, the present invention comprises a method for the controlled delivery of a therapeutic to a region of a patient using magnetic resonance imaging focused therapeutic ultrasound comprising administering to the patient vesicles comprising gas-filled vesicles comprising a therapeutic compound; monitoring the vesicles using magnetic resonance imaging to determine the presence of the vesicles in the region; and rupturing the vesicles using ultrasound to release the therapeutic in the region.

The present invention is also directed to a method of magnetic resonance focused surgical ultrasound comprising administering a contrast medium for magnetic resonance imaging comprising gaseous precursor filled vesicles to a patient requiring surgery, allowing the gaseous precursor to undergo a phase transition from a liquid to a gas, scanning the patient with magnetic resonance imaging to identify the region of the patient requiring surgery, and applying surgical ultrasound to the region. The phase transition step and the magnetic resonance scanning step may be performed simultaneously.

The contrast medium comprises stabilized gas filled vesicles, wherein the gas is a biocompatible gas, e.g., nitrogen or perfluoro-propane, but may also be derived from a gaseous precursor, e.g., perfluorooctylbromide, and the vesicles are stabilized by being formed from a stabilizing compound, e.g., a biocompatible lipid or polymer. The present invention may be carried out, often with considerable attendant advantage, by using gaseous precursors to form the gas of the gas filled vesicles. These gaseous precursors may be activated by a number of factors, but preferably are temperature activated. Such a gaseous precursor is a compound which, at a selected activation or transition temperature, changes phases from a liquid or solid to a gas. Activation thus takes place by increasing the temperature of the compound from a point below, to a point above the activation or transition temperature. Where a lipid is used to form the vesicle, the lipid may be in the form of a monolayer or bilayer, and the mono- or bilayer lipids may be used to form a series of concentric mono- or bilayers. Thus, the lipid may be used to form a unilamellar liposome (comprised of one monolayer or bilayer lipid), an oligolamellar liposome (comprised of two or three monolayer or bilayer lipids) or a multilamellar liposome (comprised of more than three monolayer or bilayer lipids). Preferably, the biocompatible lipid comprises a phospholipid. Optionally, the contrast medium may include paramagnetic and/or superparamagnetic contrast agents, preferably encapsulated by the vesicles. Also, optionally, the contrast medium may further comprise a liquid fluorocarbon compound, e.g., a perfluorocarbon, to further stabilize the vesicles. Preferably the fluorocarbon liquid is encapsulated by the vesicles.

These and other aspects of the invention will become more apparent from the following detailed description.

DETAILED DESCRIPTION OF THE INVENTION

The present invention is directed, inter alia, to a method of magnetic resonance imaging focused surgical and therapeutic ultrasound comprising administering a contrast medium for magnetic resonance imaging comprising gas filled vesicles to a patient requiring surgery, using contrast medium to scan the patient with magnetic resonance imaging to identify the region of the patient requiring surgery, and applying ultrasound to the region to carry out surgery. The ultrasound step may be performed simultaneously with magnetic resonance imaging. The application of ultrasound may be followed by a second scanning step whereby the patient is scanned with magnetic resonance imaging. The gas filled vesicles may comprise a therapeutic which may be released to a localized region of a patient upon ultrasound.

The scanning and surgical ultrasound steps may be performed repeatedly until the desired effect is achieved. In accordance with the present invention, simultaneous refers to scanning with ultrasound and magnetic resonance concurrently or synchronously; sequentially or successively; such that visualization of the disruption of vesicles and tissues by ultrasound is observed. Thus, ultrasound and magnetic resonance may be performed at the same time, or one may be followed by the other. The use of magnetic resonance imaging together with ultrasound improves the accuracy of currently available imaging modalities. The precision of magnetic resonance imaging and ultrasound together confirm the location of the vesicles, as the entire body is able to be scanned by magnetic resonance imaging which provides a large field of view, and, once located, the vesicles may be ruptured by ultrasound in the given regions of the body.

The present invention is also directed to a method of magnetic resonance focused surgical ultrasound comprising administering a contrast medium for magnetic resonance imaging comprising gaseous precursor filled vesicles to a patient requiring surgery, allowing the gaseous precursor to undergo a phase transition from a liquid to a gas, using said contrast medium to scan the patient with magnetic resonance imaging to identify the region of the patient requiring surgery, and applying surgical ultrasound to the region.

In addition, the present invention comprises a method for the controlled delivery of a therapeutic to a region of a patient using magnetic resonance focused therapeutic ultrasound comprising administering to the patient contrast medium comprising gas-filled vesicles comprising a therapeutic compound; monitoring the vesicles using magnetic resonance imaging to determine the presence of the vesicles in the region; and rupturing the vesicles using ultrasound to release the therapeutic in the region.

As employed above and throughout the disclosure, the following terms, unless otherwise indicated, shall be understood to have the following meanings.

"Magnetic resonance imaging" (MRI) uses a static main magnetic field; pulsed radiofrequency energy and pulsed magnetic gradients to create images, i.e. to visualize the vesicles. The radiofrequency and electrical gradients may be used to cause local energy deposition and activate the vesicles, however, ultrasound is the preferred energy for the purpose of activating the vesicles. In carrying out the magnetic resonance imaging method of the present invention, the contrast medium can be used alone, or in combination with other diagnostic, therapeutic or other agents. Such other agents include excipients such as flavoring or coloring materials. The magnetic resonance imaging techniques which are employed are conventional and are described, for example, in D. M. Kean and M. A. Smith, *Magnetic Resonance Imaging: Principles and Applications,* (William and Wilkins, Baltimore 1986). Contemplated MRI techniques include, but are not limited to, nuclear magnetic resonance (NMR) and electronic spin resonance (ESR), and magnetic resonance angioplasty (MRA). The preferred imaging modality is NMR. Of course, in addition to MRI, magnetic imaging may also be used to detect vesicles within the scope of the present invention. Magnetic imaging uses a magnetic field yet need not use pulsed gradients or radiofrequency energy. Magnetic imaging may be used to detect magnetic vesicles, such as and not limited to ferromagnetic vesicles. Magnetic imaging may be performed by a magnetometer superconducting quantum inferometry device (SQUID). SQUID permits rapid screening of all of the body tissues for the magnetic particles; the ultrasound may then be localized to those regions. In this application, magnetic resonance imaging includes magnetic imaging, while it is understood that magnetic imaging is the imaging of magnetic vesicles and does not include resonance of the nuclei thereof.

"Ultrasound imaging" is performed on the tissues of interest and ultrasound energy may be used to activate or rupture the vesicles once they reach their intended tissue destination. Focused or directed ultrasound refers to the application of ultrasound energy to a particular region of the body, such that the ultrasound energy is concentrated to a selected area or target zone. In addition, focused refers to the magnetic resonance which guides the ultrasound by visualizing the vesicles and the target zone; and simultaneous with ultrasound visualizing the disruption of tissues thereby. Noninvasive refers to the disruption or disturbance of internal body tissues without an incision in the skin. Ultrasound, as defined in accordance with the present invention refers to surgery resulting in tissue necrosis, i.e. disruption or destruction of tissue; repair of apertures, openings, breaks, or tears in tissue (such as a hernia); alleviation of all or part of diseased tissue (such as tumors); and the activation or rupture of vesicles adjacent to tissue by ultrasonic energy. Ultrasound is a diagnostic imaging technique which is unlike nuclear medicine and X-rays since it does not expose the patient to the harmful effects of ionizing radiation. Moreover, unlike magnetic resonance imaging, ultrasound is relatively inexpensive and can be conducted as a portable examination. In using the ultrasound technique, sound is transmitted into a patient or animal via a transducer. When the sound waves propagate through the body, they encounter interfaces from tissues and fluids. Depending on the acoustic properties of the tissues and fluids in the body, the ultrasound sound waves are partially or wholly reflected or absorbed. When sound waves are reflected by an interface they are detected by the receiver in the transducer and processed to form an image. The acoustic properties of the tissues and fluids within the body determine the contrast which appears in the resultant image. Alternatively, ultrasound may be used to visualize the vesicles and magnetic resonance imaging may be used to activate the vesicles. In addition, the strength of ultrasound energy may be at an intensity to result in rupture or activation of vesicles. The activation of the vesicles in turn disrupts the adjacent tissue such that necrosis of the tissue results.

Any of the various types of diagnostic ultrasound imaging devices may be employed in the practice of the invention, the particular type or model of the device not being critical to the method of the invention. Also suitable are devices designed for administering ultrasonic hyperthermia, such devices being described in U.S. Pat. Nos. 4,620,546, 4,658,828, and 4,586,512, the disclosures of each of which are hereby incorporated herein by reference in their entirety. Preferably, the device employs a resonant frequency (RF) spectral analyzer. The transducer probes may be applied externally or may be implanted. Ultrasound is generally initiated at lower intensity and duration, preferably at peak resonant frequency, and then intensity, time, and/or resonant frequency increased until the microsphere ruptures.

"Vesicle" refers to a spherical entity which is characterized by the presence of an internal void. Preferred vesicles are formulated from lipids, including the various lipids described herein. In any given vesicle, the lipids may be in the form of a monolayer or bilayer, and the mono- or bilayer lipids may be used to form one or more mono- or bilayers. In the case of more than one mono- or bilayer, the mono- or bilayers are generally concentric. The vesicles described herein include such entities commonly referred to as liposomes, micelles, bubbles, microbubbles, aerogels, clathrate bound vesicles, and the like. Thus, the lipids may be used to form a unilamellar vesicle (comprised of one monolayer or bilayer), an oligolamellar vesicle (comprised of about two or about three monolayers or bilayers) or a multilamellar vesicle (comprised of more than about three monolayers or bilayers). The internal void of the vesicles may be filled with a liquid, including, for example, an aqueous liquid, a gas, a gaseous precursor, and/or a solid or solute material, including, for example, a targeting ligand and/or a bioactive agent, as desired.

"Liposome" refers to a generally spherical cluster or aggregate of amphipathic compounds, including lipid compounds, typically in the form of one or more concentric layers. Most preferably the gas filled liposome is constructed of a single layer (i.e. unilamellar) or a single monolayer of lipid. A wide variety of lipids may be used to fabricate the liposomes including phospholipids and non-ionic surfactants (e.g. niosomes). Most preferably the lipids comprising the gas filled liposomes are in the gel state at physiological temperature. The liposomes may be cross-linked or polymerized and may bear polymers such as polyethylene glycol on their surfaces. Targeting ligands directed to endothelial cells are bound to the surface of the gas filled liposomes. A targeting ligand is a substance which is bound to a vesicle and directs the vesicle to a particular cell type such as and not limited to endothelial tissue and/or cells. The targeting ligand may be bound to the vesicle by covalent or non-covalent bonds. The liposomes may also be referred to herein as lipid vesicles. Most preferably the liposomes are substantially devoid of water in their interiors.

"Micelle" refers to colloidal entities which form from lipidic compounds when the concentration of the lipidic compounds, such as lauryl sulfate, is above a critical concentration. Since many of the compounds which form micelles also have surfactant properties (i.e. ability to lower surface tension and both water and fat loving—hydrophilic and lipophilic domains), these same materials may also be used to stabilize bubbles. In general these micellular materials prefer to adopt a monolayer or hexagonal H2 phase configuration, yet may also adopt a bilayer configuration. When a micellular material is used to form a gas filled vesicle, the compounds will generally adopt a radial configuration with the aliphatic (fat loving) moieties oriented toward the vesicle and the hydrophilic domains oriented away from the vesicle surface. For targeting to endothelial cells, the targeting ligands may be attached to the micellular compounds or to amphipathic materials admixed with the micellular compounds. Alternatively, targeting ligands may be adsorbed to the surface of the micellular materials stabilizing the vesicles.

"Aerogel" refers to structures which are similar to microspheres except that the internal structure of the aerogels is generally comprised of multiple small voids rather than one void. Additionally the aerogels are preferably constructed of synthetic materials (e.g. a foam prepared from baking resorcinol and formaldehyde), however natural materials such as polysaccharides or proteins may also be used to prepare aerogels. Targeting ligands may be attached to the surface of the aerogel.

"Clathrates" are generally solid materials which bind the vesicles as a host rather than coating the surface of the vesicle. A solid, semi-porous, or porous clathrate may serve as the agent stabilizing the vesicle, however the clathrate itself does not coat the entire surface of the vesicle. Rather, the clathrate forms a structure known as a "cage" having spaces into which the vesicles may fit. One or more vesicles may be adsorbed by the clathrate. Similar to microspheres, one or more surfactants may be incorporated with the clathrate and these surfactants will help to stabilize the vesicle. The surfactants will generally coat the vesicle and help to maintain the association of the vesicle with the clathrate. Useful clathrate materials for stabilizing vesicles include porous apatites such as calcium hydroxyapatite and precipitates of polymers with metal ions such as alginic acid with calcium salts. Targeting ligands directed to endothelial cells may be incorporated into the clathrate itself or into the surfactant material used in association with the clathrate.

While not intending to be bound by any particular theory of operation, the present invention is believed to rely, at least in part, on the fact that gas, liquid, and solid phases have different magnetic susceptibilities. At the interface of gas and water, for example, the magnetic domains are altered and this results in dephasing of the spins of, e.g., the hydrogen nuclei. In imaging, this is seen as a decrease in signal intensity adjacent to the gas/water interface. This effect is more marked on T2 weighted images and most prominent on gradient echo pulse sequences. The effect is increased by using narrow bandwidth extended read-out pulse sequences. The longer the echo time on a gradient echo pulse sequence, the greater the effect (i.e., the greater the degree and size of signal loss).

The stabilized gas filled vesicles useful in the present invention are believed to rely on this phase magnetic susceptibility difference, as well as on the other characteristics described in more detail herein, to provide high performance level magnetic resonance imaging contrast medium and effective rupture of vesicles of the contrast medium. The vesicles are formed from, i.e., created out of, a matrix of stabilizing compounds which permit the gas filled vesicles to be established and thereafter retain their size and shape for the period of time required to be useful in magnetic resonance imaging. The compounds also permit rupture of the vesicles at a certain energy level, which energy is preferably ultrasound energy. These stabilizing compounds are most typically those which have a hydrophobic/hydrophilic character which allows them to form monolayers or bilayers, etc., and vesicles, in the presence of water. Thus, water, saline or some other water-based medium, often referred to hereafter as a diluent, is generally an aspect of the stabilized gas filled vesicle contrast medium of the present invention.

The stabilizing compound may, in fact, be a mixture of compounds which contribute various desirable attributes to the stabilized vesicles. For example, compounds which assist in the dissolution or dispersion of the fundamental stabilizing compound have been found advantageous. A further element of the stabilized vesicles is a gas, which can be a gas at the time the vesicles are made, or can be a gaseous precursor which, responsive to an activating factor, such as temperature, is transformed from the liquid or solid phase to the gas phase. The various aspects of the stabilized gas filled contrast medium useful in the present invention will now be described.

Methods of Use

In accordance with the present invention there is provided a method of simultaneous magnetic resonance focused non-invasive ultrasound. The imaging process of the present invention may be carried out by administering a contrast medium for magnetic resonance imaging comprising gas filled vesicles to a patient requiring surgery, scanning the patient with magnetic resonance imaging to identify the region of the patient requiring surgery, and simultaneously applying ultrasound and magnetic resonance to the region. By region of a patient, it is meant the whole patient or a particular area or portion of the patient.

After administration to a patient, the vesicles, which are visible on magnetic resonance imaging, are visualized by MRI. When the location of the vesicles is determined to be in the desired region of the patient, as ascertained by MRI, then energy, preferably ultrasound energy, is applied to the region. The vesicles are activated by the energy, heating and direct and rapid coagulative necrosis of the surrounding tissue (i.e. surgical ultrasound) results. Simultaneously, the region may also be visualized by magnetic resonance imaging if desired. Preferably, the energy used for vesicle activation is high energy continuous wave ultrasound, preferably over 50 milliwatts/cm$^2$, even more preferably over 100 milliwatts/cm$^2$. Depending upon the desired therapeutic effect, the energy may be even higher, up to about 10 watts/cm$^2$. Most preferably, the energy is deposited into the tissues using a hand held magnetic resonance compatible ultrasound transducer. The ultrasound transducer is made out of non-ferrous and non-ferromagnetic material. The cables supplying energy to the ultrasound transducers may have Faraday shields to decrease the potential for artifacts which may be caused by the electrical energy passing through the cables to supply the transducers.

The amount of energy and pulse duration of ultrasound used for therapy will vary depending upon the therapeutic purpose. The ultrasonic energy is preferably focused and the focal zone is chosen to target the desired regions of vesicles.

Focused ultrasonic surgery may be performed at energies of about 2 watts/cm$^2$. Focused ultrasonic surgery energy may be at least 2 watts/cm$^2$ to about 10 watts/cm$^2$. Direct and rapid coagulative necrosis of the tissue results. Simultaneous MRI may be performed with the vesicles used to visualize the target zone or region. Then together with ultrasound, the vesicles potentiate the surgery in the target zone.

Energy range of from about 500 mW/cm$^2$ to about 10 watts/cm$^2$, preferably greater than about 1 watt is useful for cavitational tissue destruction. The vesicles lower the cavitation threshold such that cavitation will occur within the target tissues at a low energy threshold resulting in tissue destruction.

Rupture or activation of vesicles may take place at an energy range of from about 50 mW/cm$^2$ to about 500 mW/cm$^2$. Vesicles may be ruptured by non-cavitational interaction. As the vesicle is pulsed rapidly and strongly enough by ultrasound energy, the vesicle membrane degenerates. While there is likely a transient microdomain of increased temperature associated with the vesicle rupture, this process may not damage the surrounding tissues when energy and pulsing is applied at an indicated energy range. This effect of vesicle rupture may be advantageously used for localized delivery of a therapeutic. Thus, a therapeutic may be released to a region of the body with this technique. Further, energy from vesicle rupture may be used to create shock waves so that the therapeutic is also deposited released to adjacent tissues. This is particularly useful with gene therapy wherein the shock waves may be used to open transient pores in adjacent cell membranes and facilitate cellular uptake of genetic material.

An energy range of about 500 mW/cm$^2$ to about 5 watts/cm$^2$, with vesicles as nuclei, may be used to increase the conversion of high energy sound into localized tissue, thereby heating the tissue and inducing hyperthermia.

In the case of a gaseous precursor, as ultrasound energy is focused on the precursor, it causes the precursor to convert to the gaseous state. The enlarging gaseous void creates a domain of increasing magnetic susceptibility and is readily monitored on the magnetic resonance images. Monitoring is particularly enhanced by selecting precursors with well defined liquid to gas conversion temperatures, such as perfluorohexane at 56° C. The invention thus may also be used for non-invasive temperature monitoring during MRI. As the vesicles form from gaseous precursors, the materials surrounding the gaseous precursor may be ruptured. In addition, a therapeutic may be released locally into the adjacent tissue where a therapeutic is co-entrapped within the vesicle. As the vesicle forms, the absorption of energy by the vesicle interface increases. This may be used to increase heating for hyperthermia as well as to rupture the vesicle.

The contrast medium may be particularly useful in providing images of and permitting ultrasound mediated surgery and/or drug delivery in the cardiovascular region or the gastrointestinal region, but can also be employed more broadly such as in imaging the vasculature or in other ways as will be readily apparent to those skilled in the art. Cardiovascular region, as that phrase is used herein, denotes the region of the patient defined by the heart and the vasculature leading directly to and from the heart. The phrase gastrointestinal region or gastrointestinal tract, as used herein, includes the region of a patient defined by the esophagus, stomach, small and large intestines and rectum. The phrase vasculature, as used herein, denotes the blood vessels (arteries, veins, etc.) in the body or in an organ or part of the body. The patient can be any type of mammal, but most preferably is a human.

The novel stabilized gas filled vesicles, useful as contrast medium in simultaneous magnetic resonance focused noninvasive ultrasound, will be found to be suitable for use in all areas where MRI is employed.

As one skilled in the art would recognize, administration of the stabilized gas filled vesicles used in the present invention may be carried out in various fashions, such as intravascularly, orally, rectally, etc., using a variety of dosage forms. When the region to be scanned is the cardiovascular region, administration of the contrast medium of the invention is preferably carried out intravascularly. When the region to be scanned is the gastrointestinal region, administration of the contrast medium of the invention is preferably carried out orally or rectally. The useful dosage to be administered and the particular mode of administration will vary depending upon the age, weight and the particular mammal and region thereof to be scanned, and the particular contrast medium of the invention to be employed. Typically, dosage is initiated at lower levels and increased until the desired contrast enhancement is achieved. Various combinations of the stabilized gas filled vesicles may be used to modify the relaxation behavior of the medium or to alter properties such as the viscosity, osmolarity or palatability (in the case of orally administered materials). In carrying out the simultaneous magnetic resonance focused noninvasive ultrasound method of the present invention, the contrast medium can be used alone, or in combination with other diagnostic, therapeutic or other agents. Such other agents include excipients such as flavoring or coloring materials. The magnetic resonance imaging techniques which are employed are conventional and are described, for example, in D. M. Kean and M. A. Smith, *Magnetic Resonance Imaging: Principles and Applications,* (William and Wilkins, Baltimore 1986). Contemplated MRI techniques include, but are not limited to, nuclear magnetic resonance (NMR) and electronic spin resonance (ESR). The preferred imaging modality is NMR.

As noted above, the routes of administration and areas of usefulness of the gas filled vesicles are not limited merely to the blood volume space, i.e., the vasculature. Simultaneous magnetic resonance focused noninvasive ultrasound can be achieved with the gas filled vesicles used in the present invention if the vesicles are ingested by mouth so as to image the gastrointestinal tract and rupture the vesicles therein. Alternatively, rectal administration of these stabilized gas vesicles can result in excellent imaging of the lower gastrointestinal tract including the rectum, descending colon, transverse colon, and ascending colon as well as the appendix, and rupturing the vesicles therein. It may be possible to achieve imaging of the jejunum and conceivably the ileum via this rectal route; and to rupture the vesicles in these areas. As well, direct intraperitoneal administration may be achieved to visualize the peritoneum, and rupture the vesicles therein. It is also contemplated that the stabilized gas vesicles may be administered directly into the ear canals such that one can visualize the canals as well as the Eustachian tubes and, if a perforation exists, the inner ear. Further, activation or rupture of the vesicles in the ear may also take place. It is also contemplated that the stabilized gas vesicles may be administered intranasally to aid in the visualization of the nasal septum as well as the nasal sinuses, and rupture of the vesicles therein. Interstitial administration is also possible.

Other routes of administration of the vesicle contrast agents of the present invention, and tissue areas whose imaging and rupture of the vesicles is enhanced thereby include, but are not limited to 1) intranasally for imaging the nasal passages and sinuses including the nasal region and sinuses and sinusoids; 2) intranasally and orally for imaging the remainder of the respiratory tract, including the trachea, bronchus, bronchioles, and lungs; 3) intracochlearly for imaging the hearing passages and Eustachian tubes, tympanic membranes and outer and inner ear and ear canals; 4) intraocularly for imaging the regions associated with vision; 5) intraperitoneally to visualize the peritoneum; and 6) intravesicularly, i.e., through the bladder, to image all regions of the genitourinary tract via the areas thereof, including, but not limited to, the urethra, bladder, ureters, kidneys and renal vasculature and beyond, e.g., to perform cystography or to confirm the presence of ureteral reflux. In addition, the brain, spine, pulmonay region, and soft tissues such as and not including adipose tissue, muscle, and organs may be similarly imaged and surgery of these areas may be achieved by ultrasound.

Use of the procedures of the invention permit ultrasound mediated surgery. By ultrasound mediated surgery it is meant surgery effectively causing tissue necrosis, i.e. disruption, destruction, or repair of tissue, such as repair of small tears (apertures, openings, or breaks) in tissue membranes (such as a hernia); alleviation of all or part of diseased tissue (such as tumors); and the activation or rupture of vesicles adjacent to tissue by ultrasonic energy.

Gases and Gaseous Precursors

The vesicles of the invention encapsulate a gas and/or gaseous precursor. The term "gas filled and/or gaseous precursor filled", as used herein, means that the vesicles to which the present invention is directed, have an interior volume that is comprised of at least about 10% gas and gaseous precursor, preferably at least about 25% gas and gaseous precursor, more preferably at least about 50% gas and gaseous precursor, even more preferably at least about 75% gas and gaseous precursor, and most preferably at least about 90% gas and gaseous precursor. In use, where the presence of gas is important, it is preferred that the interior vesicle volume comprise at least about 10% gas, preferably at least about 25%, 50%, 75%, and most preferably at least about 90% gas.

Any of the various biocompatible gases and gaseous precursors may be employed in the gas and gaseous precursor filled vesicles of the present invention. Such gases include, for example, air, nitrogen, carbon dioxide, oxygen, argon, fluorine, xenon, neon, helium, rubidium enhanced (hyperpolarized) xenon, rubidium enhanced argon, rubidium enhanced helium, and rubidium enhanced neon, or any and all combinations thereof. Of such gases, nitrogen and fluorine are preferred. For example, the use of NMR together with $^{19}F$ provides more sensitive visualization than the use of a liquid or a solid. Likewise, various fluorinated gaseous compounds, such as various perfluorocarbon, hydrofluorocarbon, and sulfur hexafluoride gases may be utilized in the preparation of the gas filled vesicles. Also, the gases discussed in Quay, published application WO 93/05819, including the high "Q" factor gases described therein, the disclosures of which are hereby incorporated herein by reference in their entirety, may be employed. Further, paramagnetic gases or gases such as $^{17}O$ may be used. The oxygen should be stabilized, since oxygen gas is soluble in blood. Stabilization may be accomplished by an impermeable shell, preferably of a polymerized or cross-linked liposome or a cyanoacrylate microsphere; or used together with a perfluorocarbon, such as perfluoropentane or perfluorobutane. Of all of the gases, perfluorocarbons and sulfur hexafluoride are preferred. Suitable perfluorocarbon gases include, for example, perfluorobutane, perfluorocyclobutane, perfluoromethane, perfluoroethane, perfluoropropane, and perfluoropentane, perfluorohexane, most preferably perfluoropropane. Also preferred are a mixture of different types of gases, such as a perfluorocarbon gas and another type of gas such as oxygen, etc. Indeed, it is believed that a combination of gases may be particularly useful in simultaneous magnetic resonance focused noninvasive ultrasound applications.

The gaseous precursors may also be in the form of a solid. Sodium bicarbonate crystals produce carbon dioxide gas upon activation of the solid precursor form. Solid and liquid gaseous precursors are particularly useful in ultrasonic hyperthermia which activates the precursor into the gaseous state.

Notwithstanding the requirement that the gas and gaseous precursor filled vesicles be made from stabilizing compounds, it is preferred that a rather highly stable gas be utilized as well. By highly stable gas is meant a gas selected from those gases which will have low (limited) solubility and diffusability in aqueous media. Gases such as perfluorocarbons are less diffusible and relatively insoluble and as such are easier to stabilize into the form of bubbles in aqueous media.

The use of gaseous precursors is an optional embodiment of the present invention. In particular, perfluorocarbons have been found to be suitable for use as gaseous precursors. As the artisan will appreciate, a given perfluorocarbon may be used as a gaseous precursor, i.e., in the liquid or solid state when the vesicles of the present invention are first made, or may be used as a gas directly, i.e., in the gas state, to make the gas and gaseous precursor filled vesicles. Whether such a perfluorocarbon is a gas, liquid, or solid depends, of course, on its liquid/gas or solid/gas phase transition temperature, or boiling point. For example, one of the more preferred perfluorocarbons is perfluoropentane, which has a liquid/gas phase transition temperature or boiling point of 27° C., which means that it will be a liquid at ordinary room temperature, but will become a gas in the environment of the human body, where the temperature will be above its liquid/gas phase transition temperature or boiling point. Thus, under normal circumstance, perfluoropentane is a gaseous precursor. As further examples, there is perfluorobutane and perfluorohexane, the next closest homologs of perfluoropentane. The liquid/gas phase transition temperature of perfluorobutane is 4° C. and that of perfluorohexane is 57° C., making the former potentially a gaseous precursor, but generally more useful as a gas, while the latter would generally be a gaseous precursor, except under unusual circumstances, because of its high boiling point.

Another aspect of the present invention is the use of a fluorinated compound, especially a perfluorocarbon compound, which will be in the liquid state at the temperature of use of the vesicles of the present invention, to assist or enhance the stability of said gas and gaseous precursor filled vesicles. Such fluorinated compounds include various liquid fluorinated compounds, such as fluorinated surfactants manufactured by the DuPont Company (Wilmington, Del.), e.g., ZONYL™, as well as liquid perfluorocarbons. Preferably the fluorinated compounds are perfluorocarbons. Suitable perfluorocarbons useful as additional stabilizing agents include perfluorooctylbromide (PFOB), perfluorodecalin, perfluorododecalin, perfluorooctyliodide, perfluorotripropylamine, and perfluorotributylamine. In general, perfluorocarbons over six carbon atoms in length will not be gaseous, i.e., in the gas state, but rather will be liquids, i.e., in the liquid state, at normal human body temperature. These compounds may, however, additionally be utilized in preparing the stabilized gas and gaseous precursor filled vesicles used in the present invention. Preferably this perfluorocarbon is perfluorooctylbromide or perfluorohexane, which is in the liquid state at room temperature. The gas which is present may be, e.g., nitrogen or perfluoropropane, or may be derived from a gaseous precursor, which may also be a perfluorocarbon, e.g., perfluoropentane. In that case, the vesicles of the present invention would be prepared from a mixture of perfluorocarbons, which for the examples given, would be perfluoropropane (gas) or perfluoropentane (gaseous precursor) and perfluorooctylbromide (liquid). Although not intending to be bound by any theory, it is believed that the liquid fluorinated compound is situated at the interface between the gas and the membrane surface of the vesicle. There is thus formed a further stabilizing layer of liquid fluorinated compound on the internal surface of the stabilizing compound, e.g., a biocompatible lipid used to form the vesicle, and this perfluorocarbon layer also serves the purpose of preventing the gas from diffusing through the vesicle membrane. A gaseous precursor, within the context of the present invention, is a liquid or a solid at the temperature of manufacture and/or storage, but becomes a gas at least at or during the time of use.

Thus, it has been discovered that a liquid fluorinated compound, such as a perfluorocarbon, when combined with a gas or gaseous precursor ordinarily used to make the vesicles of the present invention, may confer an added degree of stability not otherwise obtainable with the gas or gaseous precursor alone. Thus, it is within the scope of the present invention to utilize a gas or gaseous precursor, such as a perfluorocarbon gaseous precursor, e.g., perfluoropentane, together with a perfluorocarbon which remains liquid after administration to a patient, i.e., whose liquid to gas phase transition temperature is above the body temperature of the patient, e.g., perfluoroctylbromide.

Any biocompatible gas or gaseous precursor may be used to form the stabilized gas and gaseous precursor filled vesicles. By "biocompatible" is meant a gas or gaseous precursor which, when introduced into the tissues of a human patient, will not result in any degree of unacceptable toxicity, including allergenic responses and disease states, and preferably are inert. Such a gas or gaseous precursor should also be suitable for making gas and gaseous precursor filled vesicles, as described herein.

The size of the gas or gaseous precursor filled vesicles becomes stabilized when the stabilizing compounds described herein are employed; and the size of the vesicles can then be adjusted for the particular intended MRI end use. For example, magnetic resonance imaging of the vasculature may require vesicles that are no larger that about 30µ in diameter, and that are preferably smaller, e.g., no larger than about 12µ in diameter. The size of the gas filled vesicles can be adjusted, if desired, by a variety of procedures including microemulsification, vortexing, extrusion, filtration, sonication, homogenization, repeated freezing and thawing cycles, extrusion under pressure through pores of defined size, and similar methods.

For intravascular use the vesicles are generally under 30µ in mean diameter, and are preferably under about 12µ in mean diameter. For targeted intravascular use, e.g., to bind to a certain tissue such as a tumor, the vesicles can be appreciably under a micron, even under 100 nm diameter. For enteric, i.e., gastrointestinal use the vesicles can be much larger, e.g., up to a millimeter in size, but vesicles between 20µ and 100µ in mean diameter are preferred.

As noted above, the embodiments of the present invention may also include, with respect to their preparation, formation and use, gaseous precursors that can be activated by temperature. Further below is set out Table I listing a series of gaseous precursors which undergo phase transitions from liquid to gaseous states at relatively close to normal body temperature (37° C.) or below, and the size of the emulsified droplets that would be required to form a microbubble of a maximum size of 10 microns.

TABLE I

Physical Characteristics of Gaseous Precursors and
Diameter of Emulsified Droplet to Form a 10 µm Vesicle*

| Compound | Molecular Weight | Boiling Point (° C.) | Density | Diameter (µm) of emulsified droplet to make 10 micron vesicle |
|---|---|---|---|---|
| perfluoro pentane | 288.04 | 28.5 | 1.7326 | 2.9 |
| 1-fluorobutane | 76.11 | 32.5 | 6.7789 | 1.2 |
| 2-methyl butane (isopentane) | 72.15 | 27.8 | 0.6201 | 2.6 |
| 2-methyl 1-butene | 70.13 | 31.2 | 0.6504 | 2.5 |
| 2-methyl-2-butene | 70.13 | 38.6 | 0.6623 | 2.5 |
| 1-butene-3-yne-2-methyl | 66.10 | 34.0 | 0.6801 | 2.4 |
| 3-methyl-1-butyne | 68.12 | 29.5 | 0.6660 | 2.5 |
| octafluoro cyclobutane | 200.04 | -5.8 | 1.48 | 2.8 |

TABLE I-continued

Physical Characteristics of Gaseous Precursors and
Diameter of Emulsified Droplet to Form a 10 µm Vesicle*

| Compound | Molecular Weight | Boiling Point (° C.) | Density | Diameter (µm) of emulsified droplet to make 10 micron vesicle |
|---|---|---|---|---|
| decafluoro butane | 238.04 | -2 | 1.517 | 3.0 |
| hexafluoro ethane | 138.01 | -78.1 | 1.607 | 2.7 |

*Source: Chemical Rubber Company Handbook of Chemistry and Physics, Robert C. Weast and David R. Lide, eds., CRC Press, Inc. Boca Raton, Florida (1989–1990).

There is also set out below a list composed of potential gaseous precursors that may be used to form vesicles of defined size. However, the list is not intended to be limiting, since it is possible to use other gaseous precursors for that purpose. In fact, for a variety of different applications, virtually any liquid can be used to make gaseous precursors so long as it is capable of undergoing a phase transition to the gas phase upon passing through the appropriate temperature, so that at least at some point in use it provides a gas. Suitable gaseous precursors for use in the present invention are the following: hexafluoro acetone, isopropyl acetylene, allene, tetrafluoro-allene, boron trifluoride, isobutane, 1,2-butadiene, 2,3-butadiene, 1,3-butadiene, 1,2,3-trichloro-2-fluoro-1,3-butadiene, 2-methyl-1,3-butadiene, hexafluoro-1,3-butadiene, butadiyne, 1-fluorobutane, 2-methyl-butane, decafluorobutane, 1-butene, 2-butene, 2-methyl-1-butene, 3-methyl-1-butene, perfluoro-1-butene, perfluoro-2-butene, 4-phenyl-3-butene-2-one, 2-methyl-1-butene-3-yne, butyl nitrate, 1-butyne, 2-butyne, 2-chloro-1,1,1,4,4,4-hexafluoro-butyne, 3-methyl-1-butyne, perfluoro-2-butyne, 2-bromo-butyraldehyde, carbonyl sulfide, crotononitrile, cyclobutane, methyl-cyclobutane, octafluoro-cyclobutane, perfluoro-cyclobutene, 3-chlorocyclopentene, octafluorocyclopentene, cyclopropane, 1, 2-dimethylcyclopropane, 1,1-dimethylcyclopropane, 1, 2-dimethylcyclopropane, ethylcyclopropane, methylcyclopropane, diacetylene, 3-ethyl-3-methyl diaziridine, 1,1,1-trifluorodiazoethane, dimethyl amine, hexafluorodimethylamine, dimethylethylamine, bis-(dimethylphosphine)amine, perfluorohexane, 2,3-dimethyl-2-norbornane, perfluorodimethylamine, dimethyloxonium chloride, 1,3-dioxolane-2-one, 4-methyl-1,1,1,2-tetrafluoroethane, 1,1,1-trifluoroethane, 1,1,2,2-tetrafluoroethane, 1,1,2-trichloro-1,2,2-trifluoroethane, 1,1-dichloroethane, 1,1-dichloro-1,2,2,2-tetrafluoroethane, 1,2-difluoroethane, 1-chloro-1,1,2,2,2-pentafluoroethane, 2-chloro-1,1-difluoroethane, 1,1-dichloro-2-fluoroethane, 1-chloro-1,1,2,2-tetrafluoroethane, 2-chloro-1,1-difluoroethane, chloroethane, chloropentafluoroethane, dichlorotrifluoroethane, fluoroethane, hexafluoroethane, nitropentafluoroethane, nitrosopentafluoroethane, perfluoroethylamine, ethyl vinyl ether, 1,1-dichloroethane, 1,1-dichloro-1,2-difluoroethane, 1,2-difluoroethane, methane, trifluoromethanesulfonylchloride, trifluoromethanesulfonylfluoride ,bromodifluoronitrosomethane, bromofluoromethane, bromochlorofluoromethane, bromotrifluoromethane, chlorodifluoronitromethane, chlorodinitromethane, chlorofluoromethane, chlorotrifluoromethane, chlorodifluoromethane, dibromodifluoromethane, dichlorodifluoromethane, dichlorofluoromethane, difluoromethane, difluoroiodomethane, disilanomethane, fluoromethane, iodomethane, iodotrifluoromethane, nitrotrifluoromethane, nitrosotrifluoromethane, tetrafluoromethane, trichlorofluoromethane, trifluoromethane, 2-methylbutane, methyl ether, methyl isopropyl ether, methyllactate, methylnitrite, methylsulfide, methyl vinyl ether, neon, neopentane, nitrogen ($N_2$), nitrous oxide, 1,2,3-nonadecane-tricarboxylic acid-2-hydroxytrimethylester, 1-nonene-3-yne, oxygen ($O_2$), 1,4-pentadiene, n-pentane, perfluoropentane, 4-amino-4-methylpentan-2-one, 1-pentene, 2-pentene (cis), 2-pentene (trans), 3-bromopent-1-ene, perfluoropent-1-ene, tetrachlorophthalic acid, 2,3,6-trimethylpiperidine, propane, 1,1,1,2,2,3-hexafluoropropane, 1,2-epoxypropane, 2,2-difluoropropane, 2-aminopropane, 2-chloropropane, heptafluoro-1-nitropropane, heptafluoro-1-nitrosopropane, perfluoropropane, propene, hexafluoropropane, 1,1,1,2,3,3-hexafluoro-2,3 dichloropropane, 1-chloropropane, chloropropane-(trans), 2-chloropropane, 3-fluoropropane, propyne, 3,3,3-trifluoropropyne, 3-fluorostyrene, sulfur hexafluoride, sulfur (di)-decafluoride ($S_2F_{10}$) , 2,4-diaminotoluene, trifluoroacetonitrile, trifluoromethyl peroxide, trifluoromethyl sulfide, tungsten hexafluoride, vinyl acetylene, vinyl ether, and xenon.

The perfluorocarbons, as already indicated, are preferred for use as the gas or gaseous precursors, as well as additional stabilizing components. Included in such perfluorocarbon compositions are saturated perfluorocarbons, unsaturated perfluorocarbons, and cyclic perfluorocarbons. The saturated perfluorocarbons, which are usually preferred, have the formula $C_nF_{2n+2}$, where n is from 1 to 12, preferably 2 to 10, more preferably 4 to 8, and most preferably 5. Examples of suitable saturated perfluorocarbons are the following: tetrafluoromethane, hexafluoroethane, octafluoropropane, decafluorobutane, dodecafluoropentane, perfluorohexane, and perfluoroheptane. Cyclic perfluorocarbons, which have the formula $C_nF_{2n}$, where n is from 3 to 8, preferably 3 to 6, may also be preferred, and include, e.g., hexafluorocyclopropane, octafluorocyclobutane, and decafluorocyclopentane.

It is part of the present invention to optimize the utility of the vesicles by using gases of limited solubility. By limited solubility, is meant the ability of the gas to diffuse out of the vesicles by virtue of its solubility in the surrounding aqueous medium. A greater solubility in the aqueous medium imposes a gradient with the gas in the vesicle such that the gas will have a tendency to diffuse out of said vesicle. A lesser solubility in the aqueous milieu, will, on the other hand, decrease or eliminate the gradient between the vesicle and the interface such that the diffusion of the gas out of the vesicle will be impeded. Preferably, the gas entrapped in the vesicle has a solubility less than that of oxygen, i.e., 1 part gas in 32 parts water. See Matheson Gas Data Book, 1966, Matheson Company Inc. More preferably, the gas entrapped in the vesicle possesses a solubility in water less than that of air; and even more preferably, the gas entrapped in the vesicle possesses a solubility in water less than that of nitrogen.

Stabilizing Compounds

One or more stabilizing compounds are employed to form the vesicles, and to assure continued encapsulation of the gases or gaseous precursors. Even for relatively insoluble, non-diffusible gases such as perfluoropropane or sulfur hexafluoride, improved vesicle preparations are obtained when one or more stabilizing compounds are utilized in the formation of the gas and gaseous precursor filled vesicles. These compounds maintain the stability and the integrity of the vesicles with regard to their size, shape and/or other attributes.

The terms "stable" or "stabilized", as used herein, means that the vesicles are substantially resistant to degradation, i.e., are resistant to the loss of vesicle structure or encapsulated gas or gaseous precursor for a useful period of time. Typically, the vesicles of the invention have a good shelf life, often retaining at least about 90 percent by volume of its original structure for a period of at least about two or three weeks under normal ambient conditions, although it is preferred that this period be at least a month, more at least preferably two months, even more preferably at least six months, still more preferably eighteen months, and most preferably three years. Thus, the gas and gaseous precursor filled vesicles typically have a good shelf life, sometimes even under adverse conditions, such as temperatures and pressures which are above or below those experienced under normal ambient conditions.

The stability of the vesicles of the present invention is attributable, at least in part, to the materials from which said vesicles are made, and it is often not necessary to employ additional stabilizing additives, although it is optional and often preferred to do so; and such additional stabilizing agents and their characteristics are explained in more detail herein. The materials from which the vesicles used in the present invention are constructed are preferably biocompatible lipid or polymer materials, and of these, the biocompatible lipids are especially preferred. In addition, because of the ease of formulation, i.e., the ability to produce the vesicles just prior to administration, these vesicles may be conveniently made on site.

The lipids and polymers employed in preparing the vesicles of the invention are biocompatible. By "biocompatible" is meant a lipid or polymer which, when introduced into the tissues of a human patient, will not result in any degree of unacceptable toxicity, including allergenic responses and disease states. Preferably the lipids or polymers are inert.

Biocompatible Lipids

For the biocompatible lipid materials, it is preferred that such lipid materials be what is often referred to as "amphiphilic" in nature (i.e., polar lipid), by which is meant any composition of matter which has, on the one hand, lipophilic, i.e., hydrophobic properties, while on the other hand, and at the same time, having lipophobic, i.e., hydrophilic properties.

Hydrophilic groups may be charged moieties or other groups having an affinity for water. Natural and synthetic phospholipids are examples of lipids useful in preparing the stabilized vesicles used in the present invention. They contain charged phosphate "head" groups which are hydrophilic, attached to long hydrocarbon tails, which are hydrophobic. This structure allows the phospholipids to achieve a single bilayer (unilamellar) arrangement in which all of the water-insoluble hydrocarbon tails are in contact with one another, leaving the highly charged phosphate head regions free to interact with a polar aqueous environment. It will be appreciated that a series of concentric bilayers are possible, i.e., oligolamellar and multilamellar, and such arrangements are also contemplated to be an aspect of the present invention. The ability to form such bilayer arrangements is one feature of the lipid materials useful in the present invention.

The lipid may alternatively be in the form of a monolayer, and the monolayer lipids may be used to form a single monolayer (unilamellar) arrangement. Alternatively, the monolayer lipid may be used to form a series of concentric monolayers, i.e., oligolamellar or multilamellar, and such arrangements are also considered to be within the scope of the invention.

It has also been found advantageous to achieving the stabilized vesicles of the present invention that they be prepared at a temperature below the gel to liquid crystalline phase transition temperature of a lipid used as the stabilizing compound. This phase transition temperature is the temperature at which a lipid bilayer will convert from a gel state to a liquid crystalline state. See, for example, Chapman et al., *J. Biol. Chem.* 1974 249, 2512–2521.

It is believed that, generally, the higher the gel state to liquid crystalline state phase transition temperature, the more impermeable the gas and gaseous precursor filled vesicles are at any given temperature. See Derek Marsh, *CRC Handbook of Lipid Bilayers* (CRC Press, Boca Raton, Fla. 1990), at p. 139 for main chain melting transitions of saturated diacyl-sn-glycero-3-phosphocholines. The gel state to liquid crystalline state phase transition temperatures of various lipids will be readily apparent to those skilled in the art and are described, for example, in Gregoriadis, ed., *Liposome Technology*, Vol. I, 1–18 (CRC Press, 1984). Table 2, below, lists some of the representative lipids and their phase transition temperatures:

TABLE 2

Saturated Diacyl sn-Glycero (3) Phosphocholines:
Main Chain Phase Transition Temperatures*

| Carbons in Acyl Chains | Main Phase Transition Temperature ° C. |
|---|---|
| 1,2-(12:0) | −1.0 |
| 1,2-(13:0) | 13.7 |
| 1,2-(14:0) | 23.5 |
| 1,2-(15:0) | 34.5 |
| 1,2-(16:0) | 41.4 |
| 1,2-(17:0) | 48.2 |
| 1,2-(18:0) | 55.1 |
| 1,2-(19:0) | 61.8 |
| 1,2-(20:0) | 64.5 |
| 1,2-(21:0) | 71.1 |
| 1,2-(22:0) | 74.0 |
| 1,2-(23:0) | 79.5 |
| 1,2-(24:0) | 80.1 |

*Derek Marsh, "CRC Handbook of Lipid Bilayers", CRC Press, Boca Raton, Florida (1990), page 139.

It has been found possible to enhance the stability of the vesicles used in the present invention by incorporating at least a small amount, i.e., about 1 to about 10 mole percent of the total lipid, of a negatively charged lipid into the lipid from which the gas and gaseous precursor filled vesicles are to be formed. Suitable negatively charged lipids include, e.g., phosphatidylserine, phosphatidic acid, and fatty acids. Such negatively charged lipids provide added stability by counteracting the tendency of the vesicles to rupture by fusing together, i.e., the negatively charged lipids tend to establish a uniform negatively charged layer on the outer surface of the vesicle, which will be repulsed by a similarly charged outer layer on the other vesicles. In this way, the vesicles will tend to be prevented from coming into touching proximity with each other, which would often lead to a rupture of the membrane or skin of the respective vesicles and consolidation of the contacting vesicles into a single, larger vesicle. A continuation of this process of consolidation will, of course, lead to significant degradation of the vesicles.

The lipid material or other stabilizing compound used to form the vesicles is also preferably flexible, by which is meant, in the context of gas and gaseous precursor filled vesicles, the ability of a structure to alter its shape, for example, in order to pass through an opening having a size smaller than the vesicle.

In selecting a lipid for preparing the stabilized vesicles used in the present invention, a wide variety of lipids will be found to be suitable for their construction. Particularly useful are any of the materials or combinations thereof known to those skilled in the art as suitable for liposome preparation. The lipids used may be of either natural, synthetic, or semi-synthetic origin.

Lipids which may be used to prepare the gas and gaseous precursor filled vesicles used in the present invention include but are not limited to: lipids such as fatty acids, lysolipids, phosphatidylcholine with both saturated and unsaturated lipids including dioleoylphosphatidylcholine; dimyristoylphosphatidylcholine; dipentadecanoylphosphatidylcholine; dilauroylphosphatidylcholine; dipalmitoylphosphatidylcholine (DPPC); distearoylphosphatidylcholine (DSPC); phosphatidylethanolamines such as dioleoylphosphatidylethanolamine and dipalmitoylphosphatidylethanolamine (DPPE); phosphatidylserine; phosphatidylglycerol; phosphatidylinositol; sphingolipids such as sphingomyelin; glycolipids such as ganglioside GM1 and GM2; glucolipids; sulfatides; glycosphingolipids; phosphatidic acids such as dipalymitoylphosphatidic acid (DPPA); palmitic acid; stearic acid; arachidonic acid; oleic acid; lipids bearing polymers such as polyethylene glycol, i.e., PEGylated lipids, chitin, hyaluronic acid or polyvinylpyrrolidone; lipids bearing sulfonated mono-, di-, oligo- or polysaccharides; cholesterol, cholesterol sulfate and cholesterol hemisuccinate; tocopherol hemisuccinate; lipids with ether and ester-linked fatty acids; polymerized lipids (a wide variety of which are well known in the art); diacetyl phosphate; dicetyl phosphate; stearylamine; cardiolipin; phospholipids with short chain fatty acids of 6–8 carbons in length; synthetic phospholipids with asymmetric acyl chains (e.g., with one acyl chain of 6 carbons and another acyl chain of 12 carbons); ceramides; non-ionic liposomes including niosomes such as polyoxyethylene fatty acid esters, polyoxyethylene fatty alcohols, polyoxyethylene fatty alcohol ethers, polyoxyethylated sorbitan fatty acid esters, glycerol polyethylene glycol oxystearate, glycerol polyethylene glycol ricinoleate, ethoxylated soybean sterols, ethoxylated castor oil, polyoxyethylene-polyoxypropylene polymers, and polyoxyethylene fatty acid stearates; sterol aliphatic acid esters including cholesterol sulfate, cholesterol butyrate, cholesterol iso-butyrate, cholesterol palmitate, cholesterol stearate, lanosterol acetate, ergosterol palmitate, and phytosterol n-butyrate; sterol esters of sugar acids including cholesterol glucuroneide, lanosterol glucuronide, 7-dehydrocholesterol glucuronide, ergosterol glucuronide, cholesterol gluconate, lanosterol gluconate, and ergosterol gluconate; esters of sugar acids and alcohols including lauryl glucuronide, stearoyl glucuronide, myristoyl glucuronide, lauryl gluconate, myristoyl gluconate, and stearoyl gluconate; esters of sugars and aliphatic acids including sucrose laurate, fructose laurate, sucrose palmitate, sucrose stearate, glucuronic acid, gluconic acid, accharic acid, and polyuronic acid; saponins including sarsasapogenin, smilagenin, hederagenin, oleanolic acid, and digitoxigenin; glycerol dilaurate, glycerol trilaurate, glycerol dipalmitate, glycerol and glycerol esters including glycerol tripalmitate, glycerol distearate, glycerol tristearate, glycerol dimyristate, glycerol trimyristate; longchain alcohols including n-decyl alcohol, lauryl alcohol, myristyl alcohol, cetyl alcohol, and n-octadecyl alcohol; 6-(5-cholesten-3β-yloxy)-1-thio-β-D- galactopyranoside; digalactosyldiglyceride; 6-(5-cholesten-3β-yloxy)hexyl-6-amino-6-deoxy-1-thio-β-D-galactopyranoside; 6-(5-cholesten-3β-yloxy)hexyl-6-amino-6-deoxyl-1-thio-α-D-mannopyranoside; 12-(((7'-diethylaminocoumarin-3-yl)carbonyl)methylamino)-octadecanoic acid; N-[12-(((7'-diethylaminocoumarin-3-yl) carbonyl)methyl-amino) octadecanoyl]-2-aminopalmitic acid; cholesteryl)4'-trimethylammonio) butanoate; N-succinyldioleoylphosphatidylethanol-amine; 1,2-dioleoyl-sn-glycerol;1,2-dipalmitoyl-sn-3-succinylglycerol; 1,3-dipalmitoyl-2-succinylglycerol;1-hexadecyl-2-palmitoyl-glycerophosphoethanolamine and palmitoylhomocysteine, and/or combinations thereof.

If desired, a variety of cationic lipids such as DOTMA, N-[1-(2,3-dioleoyloxy)propyl]-N,N,N-trimethylammoium chloride; DOTAP, 1,2-dioleoyloxy-3-(trimethylammonio) propane; and DOTB, 1,2-dioleoyl-3-(4'-trimethyl-ammonio) butanoyl-sn-glycerol may be used. In general the molar ratio of cationic lipid to non-cationic lipid in the liposome may be, for example, 1:1000, 1:100, preferably, between 2:1 to 1:10, more preferably in the range between 1:1 to 1:2.5 and most preferably 1:1 (ratio of mole amount cationic lipid to mole amount non-cationic lipid, e.g., DPPC). A wide variety of lipids may comprise the non-cationic lipid when cationic lipid is used to construct the vesicle. Preferably, this non-cationic lipid is dipalmitoylphosphatidylcholine, dipalmitoylphosphatidylethanolamine or dioleoylphosphatidyl-ethanolamine. In lieu of cationic lipids as described above, lipids bearing cationic polymers such as polylysine or polyarginine, as well as alkyl phosphonates, alkyl phosphinates, and alkyl phosphites, may also be used to construct the vesicles.

The most preferred lipids are phospholipids, preferably DPPC, DPPE, DPPA and DSPC, and most preferably DPPC.

In addition, examples of saturated and unsaturated fatty acids that may be used to prepare the stabilized vesicles used in the present invention, in the form of gas and gaseous precursor filled mixed micelles, may include molecules that may contain preferably between 12 carbon atoms and 22 carbon atoms in either linear or branched form. Hydrocarbon groups consisting of isoprenoid units and/or prenyl groups can be used as well. Examples of saturated fatty acids that are suitable include, but are not limited to, lauric, myristic, palmitic, and stearic acids; examples of unsaturated fatty acids that may be used are, but are not limited to, lauroleic, physeteric, myristoleic, palmitoleic, petroselinic, and oleic acids; examples of branched fatty acids that may be used are, but are not limited to, isolauric, isomyristic, isopalmitic, and isostearic acids. In addition, to the saturated and unsaturated groups, gas and gaseous precursor filled mixed micelles can also be composed of 5 carbon isoprenoid and prenyl groups. In addition, partially fluorinated phospholipids can be used as stabilizing compounds for coating the vesicles.

Biocompatible Polymers

The biocompatible polymers useful as stabilizing compounds for preparing the gas and gaseous precursor filled vesicles used in the present invention can be of either natural, semi-synthetic (modified natural) or synthetic origin. As used herein, the term polymer denotes a compound comprised of two or more repeating monomeric units, and preferably 10 or more repeating monomeric units. The phrase semi-synthetic polymer (or modified natural polymer), as employed herein, denotes a natural polymer that has been chemically modified in some fashion. Exemplary natural polymers suitable for use in the present invention include naturally occurring polysaccharides. Such polysaccharides include, for example, arabinans, fructans, fucans, galactans, galacturonans, glucans, mannans, xylans (such as, for example, inulin), levan, fucoidan, carrageenan, galatocarolose, pectic acid, pectin, amylose, pullulan, glycogen, amylopectin, cellulose, dextran, pustulan, chitin, agarose, keratan, chondroitan, dermatan, hyaluronic acid, alginic acid, xanthan gum, starch and various other natural homopolymer or heteropolymers such as those containing one or more of the following aldoses, ketoses, acids or amines: erythrose, threose, ribose, arabinose, xylose, lyxose, allose, altrose, glucose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof. Exemplary semi-synthetic polymers include carboxymethylcellulose, hydroxymethylcellulose, hydroxypropylmethylcellulose, methylcellulose, and methoxycellulose. Exemplary synthetic polymers suitable for use in the present invention include polyethylenes (such as, for example, polyethylene glycol, polyoxyethylene, and polyethylene terephthlate), polypropylenes (such as, for example, polypropylene glycol), polyurethanes (such as, for example, polyvinyl alcohol (PVA), polyvinylchloride and polyvinylpyrrolidone), polyamides including nylon, polystyrene, polylactic acids, fluorinated hydrocarbons, fluorinated carbons (such as, for example, polytetrafluoroethylene), and polymethylmethacrylate, and derivatives thereof. Methods for the preparation of such polymer-based vesicles will be readily apparent to those skilled in the art, once armed with the present disclosure, when the present disclosure is coupled with information known in the art, such as that described and referred to in Unger, U.S. Pat. No. 5,205,290, the disclosures of which are hereby incorporated herein by reference, in their entirety.

Preferably, when intended to be used in the gastrointestinal tract, the polymer employed is one which has a relatively high water binding capacity. When used, for example, in the gastrointestinal region, a polymer with a high water binding capacity binds a large amount of free water, enabling the polymer to carry a large volume of liquid through the gastrointestinal tract, thereby filling and distending the tract. The filled and distended gastrointestinal tract permits a clearer picture of the region. In addition, where imaging of the gastrointestinal region is desired, preferably the polymer employed is also one which is not substantially degraded within and absorbed from the gastrointestinal region. Minimization of metabolism and absorption within the gastrointestinal tract is preferable, so as to avoid the removal of the contrast agent from the tract as well as avoid the formation of gas within the tract as a result of this degradation. Moreover, particularly where gastrointestinal usage is contemplated, polymers are preferably such that they are capable of displacing air and minimizing the formation of large air bubbles within the polymer composition.

Particularly preferred embodiments of the present invention include vesicles wherein the stabilizing compound from which the stabilized gas and gaseous precursor filled vesicles are formed comprises three components: (1) a neutral (e.g., nonionic or zwitterionic) lipid, (2) a negatively charged lipid, and (3) a lipid bearing a hydrophilic polymer. Preferably, the amount of said negatively charged lipid will be greater than 1 mole percent of total lipid present, and the amount of lipid bearing a hydrophilic polymer will be greater than 1 mole percent of total lipid present. It is also preferred that said negatively charged lipid be a phosphatidic acid. The lipid bearing a hydrophilic polymer will desirably be a lipid covalently bound to said polymer, and said polymer will preferably have a weight average molecular weight of from about 400 to about 100,000. Said hydrophilic polymer is preferably selected from the group consisting of polyethyleneglycol, polypropyleneglycol, polyvinylalcohol, and polyvinylpyrrolidone and copolymers thereof. The PEG or other polymer may be bound to the DPPE or other lipid through a covalent linkage, such as through an amide, carbamate or amine linkage. Alternatively, ester, ether, thioester, thioamide or disulfide (thioester) linkages may be used with the PEG or other polymer to bind the polymer to, for example, cholesterol or other phospholipids. Where the hydrophilic polymer is polyethyleneglycol, a lipid bearing such a polymer will be said to be "PEGylated," which has reference to the abbreviation for polyethyleneglycol: "PEG." Said lipid bearing a hydrophilic polymer is preferably dipalmitoylphosphatidylethanolamine-polyethyleneglycol 5000, i.e., a dipalmitoylphosphatidylethanolamine lipid having a polyethyleneglycol polymer of a mean weight average molecular weight of about 5000 attached thereto (DPPE-PEG5000); or distearoyl-phosphatidylethanolamine-polyethyleneglycol 5000.

Preferred embodiments of the vesicle contemplated by the present invention would include, e.g., 77.5 mole percent dipalmitoylphophatidylcholine (DPPC), with 12.5 mole percent of dipalmitoylphosphatidic acid (DPPA), and with 10 mole percent of dipalmitoylphosphatidylethanolamine-polyethyleneglycol-5000 (DPPE/PEG5000). These compositions in a 82/10/8 ratio of mole percentages, respectively, is also preferred. The DPPC component is effectively neutral, since the phosphtidyl portion is negatively charged and the choline portion is positively charged. Consequently, the DPPA component, which is negatively charged, is added to enhance stabilization in accordance with the mechanism described further above regarding negatively charged lipids as an additional agent. The third component, DPPE/PEG, provides a PEGylated material bound to the lipid membrane or skin of the vesicle by the DPPE moiety, with the PEG moiety free to surround the vesicle membrane or skin, and thereby form a physical barrier to various enzymatic and other endogenous agents in the body whose function is to degrade such foreign materials. It is also theorized that the PEGylated material, because of its structural similarity to water, is able to defeat the action of the macrophages of the human immune system, which would otherwise tend to surround and remove the foreign object. The result is an increase in the time during which the stabilized vesicles can function as contrast media.

Other and Auxiliary Stabilizing Compounds

It is also contemplated to be a part of the present invention to prepare stabilized gas and gaseous precursor filled vesicles using compositions of matter in addition to the biocompatible lipids and polymers described above, provided that the vesicles so prepared meet the stability and other criteria set forth herein. These compositions may be basic and fundamental, i.e., form the primary basis for creating or establishing the stabilized gas and gaseous precursor filled vesicles. On the other hand, they may be auxiliary, i.e., act as subsidiary or supplementary agents which either enhance the functioning of the basic stabilizing compound or compounds, or else contribute some desired property in addition to that afforded by the basic stabilizing compound.

However, it is not always possible to determine whether a given compound is a basic or an auxiliary agent, since the functioning of the compound in question is determined empirically, i.e., by the results produced with respect to producing stabilized vesicles. As examples of how these basic and auxiliary compounds may function, it has been observed that the simple combination of a biocompatible lipid and water or saline when shaken will often give a cloudy solution subsequent to autoclaving for sterilization. Such a cloudy solution may function as a contrast agent, but is aesthetically objectionable and may imply instability in the form of undissolved or undispersed lipid particles. Thus, propylene glycol may be added to remove this cloudiness by facilitating dispersion or dissolution of the lipid particles. The propylene glycol may also function as a thickening agent which improves vesicle formation and stabilization by increasing the surface tension on the vesicle membrane or skin. It is possible that the propylene glycol further functions as an additional layer that coats the membrane or skin of the vesicle, thus providing additional stabilization. As examples of such further basic or auxiliary stabilizing compounds, there are conventional surfactants which may be used; see D'Arrigo U.S. Pat. Nos. 4,684,479 and 5,215,680.

Additional auxiliary and basic stabilizing compounds include such agents as peanut oil, canola oil, olive oil, safflower oil, corn oil, or any other oil commonly known to be ingestible which is suitable for use as a stabilizing compound in accordance with the requirements and instructions set forth in the instant specification.

In addition, compounds used to make mixed micelle systems may be suitable for use as basic or auxiliary stabilizing compounds, and these include, but are not limited to: lauryltrimethylammonium bromide (dodecyl-), cetyltrimethylammonium bromide (hexadecyl-), myristyltrimethylammonium bromide (tetradecyl-), alkyldimethylbenzylammonium chloride (alkyl=$C_{12}, C_{14}, C_{16}$,), benzyldimethyldodecylammonium bromide/chloride, benzyldimethyl hexadecylammonium bromide/ chloride, benzyldimethyl tetradecylammonium bromide/chloride, cetyldimethylethylammonium bromide/chloride, or cetylpyridinium bromide/chloride.

It has been found that the gas and gaseous precursor filled vesicles used in the present invention may be controlled according to size, solubility and heat stability by choosing from among the various additional or auxiliary stabilizing agents described herein. These agents can affect these parameters of the vesicles not only by their physical interaction with the lipid coatings, but also by their ability to modify the viscosity and surface tension of the surface of the gas and gaseous precursor filled vesicle. Accordingly, the gas and gaseous precursor filled vesicles used in the present invention may be favorably modified and further stabilized, for example, by the addition of one or more of a wide variety of (a) viscosity modifiers, including, but not limited to carbohydrates and their phosphorylated and sulfonated derivatives; and polyethers, preferably with molecular weight ranges between 400 and 100,000; di- and trihydroxy alkanes and their polymers, preferably with molecular weight ranges between 200 and 50,000; (b) emulsifying and/or solubilizing agents may also be used in conjunction with the lipids to achieve desired modifications and further stabilization; such agents include, but are not limited to, acacia, cholesterol, diethanolamine, glyceryl monostearate, lanolin alcohols, lecithin, mono- and di-glycerides, mono-ethanolamine, oleic acid, oleyl alcohol, poloxamer (e.g., poloxamer 188, poloxamer 184, and poloxamer 181), polyoxyethylene 50 stearate, polyoxyl 35 castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan mono-laurate, sorbitan mono-oleate, sorbitan monopalmitate, sorbitan monostearate, stearic acid, trolamine, and emulsifying wax; (c) suspending and/or viscosity-increasing agents that may be used with the lipids include, but are not limited to, acacia, agar, alginic acid, aluminum mono-stearate, bentonite, magma, carbomer 934P, carboxymethylcellulose, calcium and sodium and sodium 12, carrageenan, cellulose, dextran, gelatin, guar gum, locust bean gum, veegum, hydroxyethyl cellulose, hydroxypropyl methylcellulose, magnesium-aluminum-silicate, methylcellulose, pectin, polyethylene oxide, povidone, propylene glycol alginate, silicon dioxide, sodium alginate, tragacanth, xanthum gum, α-d-gluconolactone, glycerol and mannitol; (d) synthetic suspending agents may also be utilized such as polyethyleneglycol (PEG), polyvinylpyrrolidone (PVP), polyvinylalcohol (PVA), polypropylene glycol, and polysorbate; and (e) tonicity raising agents may be included; such agents include but are not limited to sorbitol, propyleneglycol and glycerol.

Aqueous Diluents

As mentioned earlier, where the vesicles are lipid in nature, a particularly desired component of the stabilized vesicles is an aqueous environment of some kind, which induces the lipid, because of its hydrophobic/hydrophilic nature, to form vesicles, the most stable configuration which it can achieve in such an environment. The diluents which can be employed to create such an aqueous environment include, but are not limited to water, either deionized or containing any number of dissolved salts, etc., which will not interfere with creation and maintenance of the stabilized vesicles or their use as MRI contrast agents; and normal saline and physiological saline.

Paramagnetic and Superparamagnetic Contrast Agents

In a further embodiment of the present invention, the stabilized gas filled vesicle based contrast medium of the invention may further comprise additional contrast agents such as conventional contrast agents, which may serve to increase the efficacy of the contrast medium for simultaneous magnetic resonance focused noninvasive ultrasound. Many such contrast agents are well known to those skilled in the art and include paramagnetic and superparamagnetic contrast agents.

Exemplary paramagnetic contrast agents suitable for use in the subject invention include stable free radicals (such as, for example, stable nitroxides), as well as compounds comprising transition, lanthanide and actinide elements, which may, if desired, be in the form of a salt or may be covalently or noncovalently bound to complexing agents (including lipophilic derivatives thereof) or to proteinaceous macromolecules.

Preferable transition, lanthanide and actinide elements include Gd(III), Mn(II), Cu(II), Cr(III), Fe(II), Fe(III), Co(II), Er(II), Ni(II), Eu(III) and Dy(III). More preferably, the elements include Gd(III), Mn(II), Cu(II), Fe(II), Fe(III), Eu(III) and Dy(III), especially Mn(II) and Gd(III).

These elements may, if desired, be in the form of a salt, such as a manganese salt, e.g., manganese chloride, manganese carbonate, manganese acetate, and organic salts of manganese such as manganese gluconate and manganese hydroxylapatite; and such as an iron salt, e.g., iron sulfides and ferric salts such as ferric chloride.

These elements may also, if desired, be bound, e.g., covalently or noncovalently, to complexing agents (including lipophilic derivatives thereof) or to proteinaceous macromolecules. Preferable complexing agents include, for example, diethylenetriamine-pentaacetic acid (DTPA), ethylene-diaminetetraacetic acid (EDTA), 1,4,7,10-tetraazacyclododecane-N,N',N',N'''-tetraacetic acid (DOTA), 1,4,7,10-tetraazacyclododecane-N,N',N''-triacetic acid (DO3A), 3,6,9-triaza-12-oxa-3,6,9-tricarboxymethylene-10-carboxy-13-phenyl-tridecanoic acid (B-19036), hydroxybenzylethylene-diamine diacetic acid (HBED), N,N'-bis(pyridoxyl-5-phosphate)ethylene diamine, N,N'-diacetate (DPDP), 1,4,7-triazacyclononane-N,N',N''-triacetic acid (NOTA), 1,4,8,11-tetraazacyclotetradecane-N,N',N'',N'''-tetraacetic acid (TETA), kryptands (that is, macrocyclic complexes), and desferrioxamine. More preferably, the complexing agents are EDTA, DTPA, DOTA, DO3A and kryptands, most preferably DTPA. Preferable lipophilic complexes thereof include alkylated derivatives of the complexing agents EDTA, DOTA, etc., for example, EDTA-DDP, that is, N,N'-bis-(carboxy-decylamidomethyl-N-2,3-dihydroxypropyl)-ethylenediamine-N,N'-diacetate; EDTA-ODP, that is N,N'-bis-(carboxy-octadecylamido-methyl-N-2,3-dihydroxypropyl)-ethylenediamine-N,N'-diacetate; EDTA-LDP N,N'-Bis-(carboxy-laurylamidomethyl-N-2,3-dihydroxypropyl)-ethylenediamine-N,N'-diacetate; etc.; such as those described in U.S. Ser. No. 887,290, filed May 22, 1992, the disclosures of which are hereby incorporated herein by reference in its entirety. Preferable proteinaceous macromolecules include albumin, collagen, polyarginine, polylysine, polyhistidine, γ-globulin and β-globulin. More preferably, the proteinaceous macromolecules comprise albumin, polyarginine, polylysine, and polyhistidine.

Suitable complexes thus include Mn(II)-DTPA, Mn(II)-EDTA, Mn(II)-DOTA, Mn(II)-DO3A, Mn(II)-kryptands, Gd(III)-DTPA, Gd(III)-DOTA, Gd(III)-DO3A, Gd(III)-kryptands, Cr(III)-EDTA, Cu(II)-EDTA, or iron-desferrioxamine, especially Mn(II)-DTPA or Gd(III)-DTPA.

Paramagnetic chelates, such as alkylated chelates of paramagnetic ions, as disclosed in U.S. Pat. No. 5,312,617, the disclosure of which is incorporated herein by reference in its entirety, paramagnetic copolymeric chelates as in U.S. Pat. No. 5,385,719 useful for attaching to gas filled liposomes and to the surface of gas filled polymeric liposomes, nitroxide stable free radicals (NSFRs) useful for attaching to lipids in gas filled liposomes as well as to polymers for construction gas filled liposomes and hybrid complexes comprised of chelate moieties containing one or more paramagnetic ions in close proximity with one or more NSFRs as outlined in U.S. Pat. No. 5,407,657, may be used for constructing paramagnetic gas filled liposomes. These hybrid complexes have greatly increased relaxivity and therefore increase the sensitivity to the vesicle on magnetic resonance.

Nitroxides are paramagnetic contrast agents which increase both T1 and T2 relaxation rates by virtue of one unpaired electron in the nitroxide molecule. The paramagnetic effectiveness of a given compound as an MRI contrast agent is at least partly related to the number of unpaired electrons in the paramagnetic nucleus or molecule, specifically to the square of the number of unpaired electrons. For example, gadolinium has seven unpaired electrons and a nitroxide molecule has only one unpaired electron; thus gadolinium is generally a much stronger MRI contrast agent than a nitroxide. However, effective correlation time, another important parameter for assessing the effectiveness of contrast agents, confers potential increased relaxivity to the nitroxides. When the effective correlation time is very close to the proton Larmour frequency, the relaxation rate may increase dramatically. When the tumbling rate is slowed, e.g., by attaching the paramagnetic contrast agent to a large structure, it will tumble more slowly and thereby more effectively transfer energy to hasten relaxation of the water protons. In gadolinium, however, the electron spin relaxation time is rapid and will limit the extent to which slow rotational correlation times can increase relaxivity. For nitroxides, however, the electron spin correlation times are more favorable and tremendous increases in relaxivity may be attained by slowing the rotational correlation time of these molecules. The gas filled vesicles of the present invention are ideal for attaining the goals of slowed rotational correlation times and resultant improvement in relaxivity. Although not intending to be bound by any particular theory of operation, it is contemplated that since the nitroxides may be designed to coat the perimeters of the gas filled vesicles, e.g., by making alkyl derivatives thereof, that the resulting correlation times can be optimized. Moreover, the resulting contrast medium of the present invention may be viewed as a magnetic sphere, a geometric configuration which maximizes relaxivity.

If desired, the nitroxides may be alkylated or otherwise derivitized, such as the nitroxides 2,2,5,5-tetramethyl-1-pyrrolidinyloxy, free radical, and 2,2,6,6-tetramethyl-1-piperidinyloxy, free radical (TMPO).

Exemplary superparamagnetic contrast agents suitable for use in the subject invention include metal oxides and sulfides which experience a magnetic domain, ferro- or ferrimagnetic compounds, such as pure iron, magnetic iron oxide (such as magnetite), $\gamma\text{-Fe}_2\text{O}_3$, $\text{Fe}_3\text{O}_4$, iron sulfides, manganese ferrite, cobalt, ferrite, nickel ferrite, and ferritin filled with magnetite or other magnetically active materials such as ferromagnetic and superparamagnetic materials.

The contrast agents, such as the paramagnetic and superparamagnetic contrast agents described above, may be employed as a component within the vesicles or in the contrast medium comprising the vesicles. They may be entrapped within the internal space of the vesicles, administered as a solution with the vesicles or incorporated into the stabilizing compound forming the vesicle wall.

Superparamagnetic agents may be used as clathrates to adsorb and stabilize vesicles. For example, emulsions of various perfluorocarbons, such as perfluorohexane or perfluorochlorocarbons mixed with irregular shaped iron oxide compounds. The hydrophobic clefts in the iron oxides cause nano-droplets of the liquid gaseous precursor to adhere to the surface of the solid material.

For example, if desired, the paramagnetic or superparamagnetic agents may be delivered as alkylated or other derivatives incorporated into the stabilizing compound, especially the lipidic walls of the vesicles. In particular, the nitroxides 2,2,5,5-tetramethyl-1-pyrrolidinyloxy, free radical and 2,2,6,6-tetramethyl-1-piperidinyloxy, free radical, can form adducts with long chain fatty acids at the positions of the ring which are not occupied by the methyl groups, via a number of different linkages, e.g., an acetyloxy group. Such adducts are very amenable to incorporation into the stabilizing compounds, especially those of a lipidic nature, which form the walls of the vesicles of the present invention.

Mixtures of any one or more of the paramagnetic agents and/or superparamagnetic agents in the contrast media may similarly be used.

The paramagnetic and superparamagnetic agents described above may also be coadministered separately, if desired.

The gas filled vesicles used in the present invention may not only serve as effective carriers of the superparamagnetic agents, e.g., iron oxides, but also appear to magnify the effect of the susceptibility contrast agents. Superparamagnetic contrast agents include metal oxides, particularly iron oxides but including manganese oxides, and as iron oxides, containing varying amounts of manganese, cobalt and nickel which experience a magnetic domain. These agents are nano or microparticles and have very high bulk susceptibilities and transverse relaxation rates. The larger particles, e.g., 100 nm diameter, have much higher R2 relaxivities than R1 relaxivities but the smaller particles, e.g., 10 to 15 nm diameter have somewhat lower R2 relaxivities, but much more balanced R1 and R2 values. The smallest particles, e.g., monocrystalline iron oxide particles, 3 to 5 nm in diameter, have lower R2 relaxivities, but probably the most balanced R1 and R2 relaxation rates. Ferritin can also be formulated to encapsulate a core of very high relaxation rate superparamagnetic iron. It has been discovered that stabilized gas filled vesicles used in the present invention can increase the efficacy and safety of these conventional iron oxide based MRI contrast agents.

The iron oxides may simply be incorporated into the stabilizing compounds from which the vesicles are made. Particularly, the iron oxides may be incorporated into the walls of the lipid based vesicles, e.g., adsorbed onto the surfaces of the vesicles, or entrapped within the interior of the vesicles as described in U.S. Pat. No. 5,088,499, issued Feb. 18, 1992.

Although there is no intention to limit the present invention to any particular theory as to its mode of action, it is believed that the vesicles increase the efficacy of the superparamagnetic contrast agents by several mechanisms. First, it is believed that the vesicles function so as to increase the apparent magnetic concentration of the iron oxide particles. Second, it is believed that the vesicles increase the apparent rotational correlation time of the MRI contrast agents, both paramagnetic and superparamagnetic agents, so that relaxation rates are increased. Finally, the vesicles appear to operate by way of a novel mechanism which increases the apparent magnetic domain of the contrast medium and is believed to operate in the manner described immediately below.

The vesicles may be thought of as flexible spherical domains of differing susceptibility from the suspending medium, i.e., the aqueous suspension of the contrast medium and the gastrointestinal fluids in the case of gastrointestinal administration, and blood or other body fluids in the cases of intravascular injection or injection into another body space. When considering ferrites or iron oxide particles, it should be noted that these agents have a particle size dependent effect on contrast, i.e., it depends on the particle diameter of the iron oxide particle. This phenomenon is very common and is often referred to as the "secular" relaxation of the water molecules. Described in more physical terms, this relaxation mechanism is dependent upon the effective size of the molecular complex in which a paramagnetic atom, or paramagnetic molecule, or molecules, may reside. One physical explanation may be described in the following Solomon-Bloembergen equations which define the paramagnetic contributions to the $T_1$ and $T_2$ relaxation times of a spin ½ nucleus with gyromagnetic ratio g perturbed by a paramagnetic ion:

$$1/T_1M=(2/15)\ S(S+1)\ \gamma^2 g^2\beta^2/r^6[3\tau_c/(1+\omega_I^2\tau_c^2)+7\tau_c/(1+\omega_s^2\tau_c^2)]+(2/3)\ S(S+1)A^2/h^2[\tau_e/(1+\omega_s 2\tau_e^2)]$$

and $$1/T_2M=(1/15)\ S(S+1)\ \gamma^2 g^2\beta^2/r^6[4\tau_c+3\tau_c/(1+\omega_I^2\tau_c^2)+13\tau_c/(1+\omega_s^2\tau^2)]+(1/3)\ S(S+1)A^2/h^2[\tau_e/(1+\omega_s 2\tau_e^2)]$$

where:

S=electron spin quantum number;

g=electronic g factor;

β=Bohr magneton;

$\omega_I$ and $\omega_s$ (=657 $w_I$)=Larmor angular precession frequencies for the nuclear spins and electron spins;

r=ion-nucleus distance;

A=hyperfine coupling constant;

$\tau_c$ and $\tau_e$=correlation times for the dipolar and scalar interactions, respectively; and h=Planck's constant.

See, e.g., Solomon, I. Phys. Rev. 99, 559 (1955) and Bloembergen, N. J. Chem. Phys. 27, 572, 595 (1957), the disclosures of which are hereby incorporated by reference in their entirety.

A few large particles will generally have a much greater effect than a larger number of much smaller particles, primarily due to a larger correlation time. If one were to make the iron oxide particles very large however, they might be toxic and embolize the lungs or activate the complement cascade system. Furthermore, it is not the total size of the particle that matters, but particularly the diameter of the particle at its edge or outer surface. The domain of magnetization or susceptibility effect falls off exponentially from the surface of the particle. Generally speaking, in the case of dipolar (through space) relaxation mechanisms, this exponential fall off exhibits an $r^6$ dependence. Literally interpreted, a water molecule that is 4 angstroms away from a paramagnetic surface will be influenced 64 times less than a water molecule that is 2 angstroms away from the same paramagnetic surface. The ideal situation in terms of maximizing the contrast effect would be to make the iron oxide particles hollow, flexible and as large as possible. Up until now it has not been possible to do this; furthermore, these benefits have probably been unrecognized until now. By coating the inner or outer surfaces of the vesicles with the contrast agents, even though the individual contrast agents, e.g., iron oxide nanoparticles or paramagnetic ions, are relatively small structures, the effectiveness of the contrast agents may be greatly enhanced. In so doing, the contrast agents may function as an effectively much larger sphere wherein the effective domain of magnetization is determined by the diameter of the vesicle and is maximal at the surface of the vesicle. These agents afford the advantage of flexibility, i.e., compliance. While rigid vesicles might lodge in the lungs or other organs and cause toxic reactions, these flexible vesicles slide through the capillaries much more easily.

Methods of Preparation

The stabilized gas filled vesicles used in the present invention may be prepared by a number of suitable methods. These are described below separately for the case where the vesicles are gas filled, and where they are gaseous precursor filled, although vesicles having both a gas and gaseous precursor are part of the present invention.

Utilizing a Gas

A preferred embodiment comprises the steps of agitating an aqueous solution comprising a stabilizing compound, preferably a lipid, in the presence of a gas at a temperature below the gel to liquid crystalline phase transition temperature of the lipid to form gas filled vesicles. The term agitating, and variations thereof, as used herein, means any motion that shakes an aqueous solution such that gas is introduced from the local ambient environment into the aqueous solution. The shaking must be of sufficient force to result in the formation of vesicles, particularly stabilized vesicles. The shaking may be by swirling, such as by vortexing, side-to-side, or up-and-down motion. Different types of motion may be combined. Also, the shaking may occur by shaking the container holding the aqueous lipid solution, or by shaking the aqueous solution within the container without shaking the container itself.

Further, the shaking may occur manually or by machine. Mechanical shakers that may be used include, for example, a shaker table such as a VWR Scientific (Cerritos, Calif.) shaker table, or a Wig-L-Bug® Shaker from Crescent Dental Mfg. Ltd., Lyons, Ill., which has been found to give excellent results. It is a preferred embodiment of the present invention that certain modes of shaking or vortexing be used to make stable vesicles within a preferred size range. Shaking is preferred, and it is preferred that this shaking be carried out using the Wig-L-Bug® mechanical shaker. In accordance with this preferred method, it is preferred that a reciprocating motion be utilized to generate the gas filled vesicles. It is even more preferred that the motion be reciprocating in the form of an arc. It is still more preferred that the motion be reciprocating in the form of an arc between about 2° and about 20°, and yet further preferred that the arc be between about 5° and about 8°. It is most preferred that the motion is reciprocating between about 6° and about 7°, most particularly about 6.5°. It is contemplated that the rate of reciprocation, as well as the arc thereof, is critical to determining the amount and size of the gas filled vesicles formed. It is a preferred embodiment of the present invention that the number of reciprocations, i.e., full cycle oscillations, be within the range of about 1000 and about 20,000 per minute. More preferably, the number of reciprocations or oscillations will be between 2500 and 8000. The Wig-L-Bug®, referred to above, is a mechanical shaker which provides 2000 pestle strikes every 10 seconds, i.e., 6000 oscillations every minute. Of course, the number of oscillations is dependent upon the mass of the contents being agitated, with the larger the mass, the fewer the number of oscillations). Another means for producing shaking includes the action of gas emitted under high velocity or pressure.

It will also be understood that preferably, with a larger volume of aqueous solution, the total amount of force will be correspondingly increased. Vigorous shaking is defined as at least about 60 shaking motions per minute, and is preferred. Vortexing at least 60–300 revolutions per minute is more preferred. Vortexing at 300–1800 revolutions per minute is most preferred. The formation of gas filled vesicles upon shaking can be detected visually. The concentration of lipid required to form a desired stabilized vesicle level will vary depending upon the type of lipid used, and may be readily determined by routine experimentation. For example, in preferred embodiments, the concentration of 1,2-dipalimitoyl-phosphatidylcholine (DPPC) used to form stabilized vesicles according to the methods of the present invention is about 0.1 mg/ml to about 30 mg/ml of saline solution, more preferably from about 0.5 mg/ml to about 20 mg/ml of saline solution, and most preferably from about 1 mg/ml to about 10 mg/ml of saline solution. The concentration of distearoylphosphatidylcholine (DSPC) used in preferred embodiments is about 0.1 mg/ml to about 30 mg/ml of saline solution, more preferably from about 0.5 mg/ml to about 20 mg/ml of saline solution, and most preferably from about 1 mg/ml to about 10 mg/ml of saline solution.

In addition to the simple shaking methods described above, more elaborate, but for that reason less preferred, methods can also be employed, e.g., liquid crystalline shaking gas instillation processes, and vacuum drying gas instillation processes, such as those described in U.S. Ser. No. 076,250, filed Jun. 11, 1993, which is incorporated herein by reference, in its entirety. When such processes are used, the stabilized vesicles which are to be gas filled, may be prepared prior to gas installation using any one of a variety of conventional liposome preparatory techniques which will be apparent to those skilled in the art. These techniques include freeze-thaw, as well as techniques such as sonication, chelate dialysis, homogenization, solvent infusion, microemulsification, spontaneous formation, solvent vaporization, French pressure cell technique, controlled detergent dialysis, and others, each involving preparing the vesicles in various fashions in a solution containing the desired active ingredient so that the therapeutic, cosmetic or other agent is encapsulated in, enmeshed in, or attached the resultant polar-lipid based vesicle. See, e.g., Madden et al., *Chemistry and Physics of Lipids,* 1990 53, 37–46, the disclosure of which is hereby incorporated herein by reference in its entirety.

The gas filled vesicles prepared in accordance with the methods described above range in size from below a micron to over 100$\mu$ in size. In addition, it will be noted that after the extrusion and sterilization procedures, the agitation or shaking step yields gas filled vesicles with little to no residual anhydrous lipid phase (Bangham, A. D., Standish, M. M, & Watkins, J. C. (1965) *J. Mol. Biol.* 13, 238–252) present in the remainder of the solution. The resulting gas filled vesicles remain stable on storage at room temperature for a year or even longer.

The size of gas filled vesicles can be adjusted, if desired, by a variety of procedures including microemulsification, vortexing, extrusion, filtration, sonication, homogenization, repeated freezing and thawing cycles, extrusion under pressure through pores of defined size, and similar methods. It may also be desirable to use the vesicles of the present invention as they are formed, without any attempt at further modification of the size thereof.

The gas filled vesicles may be sized by a simple process of extrusion through filters; the filter pore sizes control the size distribution of the resulting gas filled vesicles. By using two or more cascaded, i.e., a stacked set of filters, e.g., 10$\mu$ followed by 8$\mu$, the gas filled vesicles have a very narrow size distribution centered around 7–9 $\mu$m. After filtration, these stabilized gas filled vesicles remain stable for over 24 hours.

The sizing or filtration step may be accomplished by the use of a filter assembly when the suspension is removed from a sterile vial prior to use, or even more preferably, the filter assembly may be incorporated into the syringe itself during use. The method of sizing the vesicles will then comprise using a syringe comprising a barrel, at least one filter, and a needle; and will be carried out by a step of extracting which comprises extruding said vesicles from said barrel through said filter fitted to said syringe between said barrel and said needle, thereby sizing said vesicles before they are administered to a patient in the course of using the vesicles as MRI contrast agents in accordance with the present invention. The step of extracting may also comprise drawing said vesicles into said syringe, where the filter will function in the same way to size the vesicles upon entrance into the syringe. Another alternative is to fill such a syringe with vesicles which have already been sized by some other means, in which case the filter now functions to ensure that only vesicles within the desired size range, or of the desired maximum size, are subsequently administered by extrusion from the syringe.

Typical of the devices which can be used for carrying out the sizing or filtration step, is the syringe and filter combination shown in FIG. 2 of U.S. application Ser. No. 08/401, 974, filed Mar. 9, 1995, the disclosure of which is incorporated by reference in its entirety.

In preferred embodiments, the stabilizing compound solution or suspension is extruded through a filter and the said solution or suspension is heat sterilized prior to shaking. Once gas filled vesicles are formed, they may be filtered for sizing as described above. These steps prior to the formation of gas filled vesicles provide the advantages, for example, of reducing the amount of unhydrated stabilizing compound, and thus providing a significantly higher yield of gas filled vesicles, as well as and providing sterile gas filled vesicles ready for administration to a patient. For example, a mixing vessel such as a vial or syringe may be filled with a filtered stabilizing compound, especially lipid suspension, and the suspension may then be sterilized within the mixing vessel, for example, by autoclaving. Gas may be instilled into the lipid suspension to form gas filled vesicles by shaking the sterile vessel. Preferably, the sterile vessel is equipped with a filter positioned such that the gas filled vesicles pass through the filter before contacting a patient.

The first step of this preferred method, extruding the stabilizing, especially lipid, solution through a filter, decreases the amount of unhydrated compound by breaking up the dried compound and exposing a greater surface area for hydration. Preferably, the filter has a pore size of about 0.1 to about 5 $\mu$m, more preferably, about 0.1 to about 4 $\mu$m, even more preferably, about 0.1 to about 2 $\mu$m, and most preferably, about 1 $\mu$m. Unhydrated compound, especially lipid, appears as amorphous clumps of non-uniform size and is undesirable.

The second step, sterilization, provides a composition that may be readily administered to a patient for MRI imaging. Preferably, sterilization is accomplished by heat sterilization, preferably, by autoclaving the solution at a temperature of at least about 100° C., and more preferably, by autoclaving at about 100° C. to about 130° C., even more preferably, about 110° C. to about 130° C., even more preferably, about 120° C. to about 130° C., and most preferably, about 130° C. Preferably, heating occurs for at least about 1 minute, more preferably, about 1 to about 30 minutes, even more preferably, about 10 to about 20 minutes, and most preferably, about 15 minutes.

If desired, alternatively the first and second steps, as outlined above, may be reversed, or only one of the two steps employed.

Where sterilization occurs by a process other than heat sterilization at a temperature which would cause rupture of the gas filled vesicles, sterilization may occur subsequent to the formation of the gas filled vesicles, and is preferred. For example, gamma radiation may be used before and/or after gas filled vesicles are formed.

Utilizing a Gaseous Precursor

In addition to the aforementioned embodiments, one can also use gaseous precursors contained in the lipid-based vesicles that can, upon activation by temperature, light, or pH, or other properties of the tissues of a host to which it is administered, undergo a phase transition from a liquid or solid entrapped in the lipid-based vesicles, to a gaseous state, expanding to create the stabilized, gas filled vesicles used in the present invention. This technique is described in detail in patent applications Ser. No. 08/160,232, filed Nov. 30, 1993, and Ser. No. 08/159,687, filed Nov. 30, 1993, both of which are incorporated herein by reference in their entirety. The techniques for preparing gaseous precursor filled vesicles are generally similar to those described for the preparation of gas filled vesicles herein, except that a gaseous precursor is substituted for the gas.

The preferred method of activating the gaseous precursor is by temperature. Activation or transition temperature, and like terms, refer to the boiling point of the gaseous precursor, the temperature at which the liquid to gaseous phase transition of the gaseous precursor takes place. Useful gaseous precursors are those gases which have boiling points in the range of about −100° C. to 70° C. The activation temperature is particular to each gaseous precursor. An activation temperature of about 37° C., or human body temperature, is preferred for gaseous precursors of the present invention. Thus, a liquid gaseous precursor is activated to become a gas at 37° C. However, the gaseous precursor may be in liquid or gaseous phase for use in the methods of the present invention. The methods of preparing the MRI contrast agents used in the present invention may be carried out below the boiling point of the gaseous precursor such that a liquid is incorporated into a vesicle. In addition, the said methods may be performed at the boiling point of the gaseous precursor such that a gas is incorporated into a vesicle. For gaseous precursors having low temperature boiling points, liquid precursors may be emulsified using a microfluidizer device chilled to a low temperature. The boiling points may also be depressed using solvents in liquid media to utilize a precursor in liquid form. Further, the methods may be performed where the temperature is increased throughout the process, whereby the process starts with a gaseous precursor as a liquid and ends with a gas.

The gaseous precursor may be selected so as to form the gas in situ in the targeted tissue or fluid, in vivo upon entering the patient or animal, prior to use, during storage, or during manufacture. The methods of producing the temperature-activated gaseous precursor-filled vesicles may be carried out at a temperature below the boiling point of the gaseous precursor. In this embodiment, the gaseous precursor is entrapped within a vesicle such that the phase transition does not occur during manufacture. Instead, the gaseous precursor-filled vesicles are manufactured in the liquid phase of the gaseous precursor. Activation of the phase transition may take place at any time as the temperature is allowed to exceed the boiling point of the precursor. Also, knowing the amount of liquid in a droplet of liquid gaseous precursor, the size of the vesicles upon attaining the gaseous state may be determined.

Alternatively, the gaseous precursors may be utilized to create stable gas filled vesicles which are pre-formed prior to use. In this embodiment, the gaseous precursor is added to a container housing a suspending and/or stabilizing medium at a temperature below the liquid-gaseous phase transition temperature of the respective gaseous precursor. As the temperature is then exceeded, and an emulsion is formed between the gaseous precursor and liquid solution, the gaseous precursor undergoes transition from the liquid to the gaseous state. As a result of this heating and gas formation, the gas displaces the air in the head space above the liquid suspension so as to form gas filled lipid spheres which entrap the gas of the gaseous precursor, ambient gas (e.g., air) or coentrap gas state gaseous precursor and ambient air. This phase transition can be used for optimal mixing and stabilization of the MRI contrast medium. For example, the gaseous precursor, perfluorobutane, can be entrapped in the biocompatible lipid or other stabilizing compound, and as the temperature is raised, beyond 4° C. (boiling point of perfluorobutane) stabilizing compound entrapped fluorobutane gas results. As an additional example, the gaseous precursor fluorobutane, can be suspended in an aqueous suspension containing emulsifying and stabilizing agents such as glycerol or propylene glycol and vortexed on a commercial vortexer. Vortexing is commenced at a temperature low enough that the gaseous precursor is liquid and is continued as the temperature of the sample is raised past the phase transition temperature from the liquid to gaseous state. In so doing, the precursor converts to the gaseous state during the microemulsification process. In the presence of the appropriate stabilizing agents, surprisingly stable gas filled vesicles result.

Accordingly, the gaseous precursors may be selected to form a gas filled vesicle in vivo or may be designed to produce the gas filled vesicle in situ, during the manufacturing process, on storage, or at some time prior to use.

As a further embodiment of this invention, by pre-forming the liquid state of the gaseous precursor into an aqueous emulsion and maintaining a known size, the maximum size of the microbubble may be estimated by using the ideal gas law, once the transition to the gaseous state is effectuated. For the purpose of making gas filled vesicles from gaseous precursors, the gas phase is assumed to form instantaneously and no gas in the newly formed vesicle has been depleted due to diffusion into the liquid (generally aqueous in nature). Hence, from a known liquid volume in the emulsion, one actually would be able to predict an upper limit to the size of the gaseous vesicle.

Pursuant to the present invention, an emulsion of a stabilizing compound such as a lipid, and a gaseous precursor, containing liquid droplets of defined size may be formulated, such that upon reaching a specific temperature, the boiling point of the gaseous precursor, the droplets will expand into gas filled vesicles of defined size. The defined size represents an upper limit to the actual size because factors such as gas diffusion into solution, loss of gas to the atmosphere, and the effects of increased pressure are factors for which the ideal gas law cannot account.

The ideal gas law and the equation for calculating the increase in volume of the gas bubbles on transition from the liquid to gaseous states is as follows:

$$PV = nRT$$

where

P=pressure in atmospheres

V=volume in liters n=moles of gas

T=temperature in ° K

R=ideal gas constant=22.4 L atmospheres deg$^{-1}$ mole$^{-1}$

With knowledge of volume, density, and temperature of the liquid in the emulsion of liquids, the amount (e.g., number of moles) of liquid precursor as well as the volume of liquid precursor, a priori, may be calculated, which when converted to a gas, will expand into a vesicle of known volume. The calculated volume will reflect an upper limit to the size of the gas filled vesicle, assuming instantaneous expansion into a gas filled vesicle and negligible diffusion of the gas over the time of the expansion.

Thus, for stabilization of the precursor in the liquid state in an emulsion wherein the precursor droplet is spherical, the volume of the precursor droplet may be determined by the equation:

$$\text{Volume (sphere)} = 4/3\pi r^3$$

where r=radius of the sphere

Thus, once the volume is predicted, and knowing the density of the liquid at the desired temperature, the amount of liquid (gaseous precursor) in the droplet may be determined. In more descriptive terms, the following can be applied:

$$V_{gas} = 4/3\pi (r_{gas})^3$$

by the ideal gas law, $$PV = nRT$$

substituting reveals, $$V_{gas} = nRT/P_{gas}$$

or, $$n = 4/3[\pi r_{gas3}]P/RT \quad (A)$$

$$\text{amount } n = 4/3[\pi r_{gas}^3 \, P/RT]*MW_n$$

Converting back to a liquid volume $$V_{liq} = [4/3[\pi r_{gas}^3]P/RT]*MW_n/D] \quad (B)$$

where D=the density of the precursor
Solving for the diameter of the liquid droplet, $$\text{diameter}/2 = [3/4\pi[4/3*[\pi r_{gas}^3]P/RT]MW_n/D]^{1/3} \quad (C)$$

which reduces to $$\text{Diameter}=2[[r_{gas}^3]P/RT[MW_n/D]]^{1/3}$$

As a further means of preparing vesicles of the desired size for use as MRI contrast agents in the present invention, and with a knowledge of the volume and especially the radius of the stabilizing compound/precursor liquid droplets, one can use appropriately sized filters in order to size the gaseous precursor droplets to the appropriate diameter sphere.

A representative gaseous precursor may be used to form a vesicle of defined size, for example, 10$\mu$ diameter. In this example, the vesicle is formed in the bloodstream of a human being, thus the typical temperature would be 37° C. or 310° K. At a pressure of 1 atmosphere and using the equation in (A), $7.54\times10^{-17}$ moles of gaseous precursor would be required to fill the volume of a 10$\mu$ diameter vesicle.

Using the above calculated amount of gaseous precursor, and 1-fluorobutane, which possesses a molecular weight of 76.11, a boiling point of 32.5° C. and a density of 0.7789 grams/mL$^{-1}$ at 20° C., further calculations predict that $5.74\times10^{-15}$ grams of this precursor would be required for a 10$\mu$ vesicle. Extrapolating further, and armed with the knowledge of the density, equation (B) further predicts that $8.47\times10^{-16}$ mLs of liquid precursor are necessary to form a vesicle with an upper limit of 10$\mu$.

Finally, using equation (C), an emulsion of lipid droplets with a radius of 0.0272$\mu$ or a corresponding diameter of 0.0544$\mu$ need be formed to make a gaseous precursor filled vesicle with an upper limit of a 10$\mu$ vesicle.

An emulsion of this particular size could be easily achieved by the use of an appropriately sized filter. In addition, as seen by the size of the filter necessary to form gaseous precursor droplets of defined size, the size of the filter would also suffice to remove any possible bacterial contaminants and, hence, can be used as a sterile filtration as well.

This embodiment for preparing gas filled vesicles used as simultaneous magnetic resonance focused noninvasive ultrasound contrast agents in the methods of the present invention may be applied to all gaseous precursors activated by temperature. In fact, depression of the freezing point of the solvent system allows the use gaseous precursors which would undergo liquid-to-gas phase transitions at temperatures below 0° C. The solvent system can be selected to provide a medium for suspension of the gaseous precursor. For example, 20% propylene glycol miscible in buffered saline exhibits a freezing point depression well below the freezing point of water alone. By increasing the amount of propylene glycol or adding materials such as sodium chloride, the freezing point can be depressed even further.

The selection of appropriate solvent systems may be explained by physical methods as well. When substances, solid or liquid, herein referred to as solutes, are dissolved in a solvent, such as water based buffers for example, the freezing point is lowered by an amount that is dependent upon the composition of the solution. Thus, as defined by Wall, one can express the freezing point depression of the solvent by the following equation:

$$Inx_a=In(1-x_b)=\Delta H_{fus}/R(1/T_o-1/T)$$

where:

$x_a$=mole fraction of the solvent $x_b$=mole fraction of the solute $\Delta H_{fus}$=heat of fusion of the solvent $T_o$=Normal freezing point of the solvent The normal freezing point of the solvent results from solving the equation. If $x_b$ is small relative to $x_a$, then the above equation may be rewritten:

$$x^b=\Delta H_{fus}/R[T-T_o/T_oT]\sim\Delta H_{fus}\Delta T/RT_o^2$$

The above equation assumes the change in temperature $\Delta T$ is small compared to $T_2$. The above equation can be simplified further assuming the concentration of the solute (in moles per thousand grams of solvent) can be expressed in terms of the molality, m. Thus, $$X_b=m/[m+1000/m_a]\sim mMa/1000$$

where:

Ma=Molecular weight of the solvent, and m=molality of the solute in moles per 1000 grams.

Thus, substituting for the fraction $x_b$:

$$\Delta T=[M_aRT_o^2/1000\Delta H_{fus}]m$$

or $$\Delta T=K_fm,$$

where $$K_f=M_aRT_o^2/1000\Delta H_{fus}$$

$K_f$ is referred to as the molal freezing point and is equal to 1.86 degrees per unit of molal concentration for water at one atmosphere pressure. The above equation may be used to accurately determine the molal freezing point of gaseous-precursor filled vesicle solutions used in the present invention.

Hence, the above equation can be applied to estimate freezing point depressions and to determine the appropriate concentrations of liquid or solid solute necessary to depress the solvent freezing temperature to an appropriate value.

Methods of preparing the temperature activated gaseous precursor-filled vesicles include:

(a) vortexing an aqueous suspension of gaseous precursor-filled vesicles used in the present invention; variations on this method include optionally autoclaving before shaking, optionally heating an aqueous suspension of gaseous precursor and lipid, optionally venting the vessel containing the suspension, optionally shaking or permitting the gaseous precursor vesicles to form spontaneously and cooling down the gaseous precursor filled vesicle suspension, and optionally extruding an aqueous suspension of gaseous precursor and lipid through a filter of about $0.22\mu$, alternatively, filtering may be performed during in vivo administration of the resulting vesicles such that a filter of about $0.22\mu$ is employed;

(b) a microemulsification method whereby an aqueous suspension of gaseous precursor-filled vesicles of the present invention are emulsified by agitation and heated to form vesicles prior to administration to a patient; and (c) forming a gaseous precursor in lipid suspension by heating, and/or agitation, whereby the less dense gaseous precursor-filled vesicles float to the top of the solution by expanding and displacing other vesicles in the vessel and venting the vessel to release air; and (d) in any of the above methods, utilizing a sealed vessel to hold the aqueous suspension of gaseous precursor and stabilizing compound such as biocompatible lipid, said suspension being maintained at a temperature below the phase transition temperature of the gaseous precursor, followed by autoclaving to move the temperature above the phase transition temperature, optionally with shaking, or permitting the gaseous precursor vesicles to form spontaneously, whereby the expanded gaseous precursor in the sealed vessel increases the pressure in said vessel, and cooling down the gas filled vesicle suspension.

Freeze drying is useful to remove water and organic materials from the stabilizing compounds prior to the shaking gas instillation method. Drying-gas instillation methods may be used to remove water from vesicles. By pre-entrapping the gaseous precursor in the dried vesicles (i.e., prior to drying) after warming, the gaseous precursor may expand to fill the vesicle. Gaseous precursors can also be used to fill dried vesicles after they have been subjected to vacuum. As the dried vesicles are kept at a temperature below their gel state to liquid crystalline temperature, the drying chamber can be slowly filled with the gaseous precursor in its gaseous state, e.g., perfluorobutane can be used to fill dried vesicles composed of dipalmitoylphosphatidylcholine (DPPC) at temperatures between 4° C. (the boiling point of perfluorobutane) and below 40° C., the phase transition temperature of the biocompatible lipid. In this case, it would be most preferred to fill the vesicles at a temperature about 4° C. to about 5° C.

Preferred methods for preparing the temperature activated gaseous precursor-filled vesicles comprise shaking an aqueous solution having a stabilizing compound such as a biocompatible lipid in the presence of a gaseous precursor at a temperature below the gel state to liquid crystalline state phase transition temperature of the lipid. The present invention also contemplates the use of a method for preparing gaseous precursor-filled vesicles comprising shaking an aqueous solution comprising a stabilizing compound such as a biocompatible lipid in the presence of a gaseous precursor, and separating the resulting gaseous precursor-filled vesicles for MRI imaging use. Vesicles prepared by the foregoing methods are referred to herein as gaseous precursor-filled vesicles prepared by a gel state shaking gaseous precursor instillation method.

Conventional, aqueous-filled liposomes of the prior art are routinely formed at a temperature above the phase transition temperature of the lipids used to make them, since they are more flexible and thus useful in biological systems in the liquid crystalline state. See, for example, Szoka and Papahadjopoulos, *Proc. Natl. Acad. Sci.* 1978, 75, 4194–4198. In contrast, the vesicles made according to preferred embodiments described herein are gaseous precursor-filled, which imparts greater flexibility, since gaseous precursors after gas formation are more compressible and compliant than an aqueous solution. Thus, the gaseous precursor-filled vesicles may be utilized in biological systems when formed at a temperature below the phase transition temperature of the lipid, even though the gel phase is more rigid.

The methods contemplated by the present invention provide for shaking an aqueous solution comprising a stabilizing compound such as a biocompatible lipid in the presence of a temperature activated gaseous precursor. Shaking, as used herein, is defined as a motion that agitates an aqueous solution such that gaseous precursor is introduced from the local ambient environment into the aqueous solution. Any type of motion that agitates the aqueous solution and results in the introduction of gaseous precursor may be used for the shaking. The shaking must be of sufficient force to allow the formation of a suitable number of vesicles after a period of time. Preferably, the shaking is of sufficient force such that vesicles are formed within a short period of time, such as 30 minutes, and preferably within 20 minutes, and more preferably, within 10 minutes. The shaking may be by microemulsifying, by microfluidizing, for example, swirling (such as by vortexing), side-to-side, or up and down motion. In the case of the addition of gaseous precursor in the liquid state, sonication may be used in addition to the shaking methods set forth above. Further, different types of motion may be combined. Also, the shaking may occur by shaking the container holding the aqueous lipid solution, or by shaking the aqueous solution within the container without shaking the container itself. Further, the shaking may occur manually or by machine. Mechanical shakers that may be used include, for example, a shaker table, such as a VWR Scientific (Cerritos, Calif.) shaker table, a microfluidizer, Wig-L-Bug™ (Crescent Dental Manufacturing, Inc., Lyons, Ill.), which has been found to give particularly good results, and a mechanical paint mixer, as well as other known machines. Another means for producing shaking includes the action of gaseous precursor emitted under high velocity or pressure. It will also be understood that preferably, with a larger volume of aqueous solution, the total amount of force will be correspondingly increased. Vigorous shaking is defined as at least about 60 shaking motions per minute, and is preferred. Vortexing at least 1000 revolutions per minute, an example of vigorous shaking, is more preferred. Vortexing at 1800 revolutions per minute is most preferred.

The formation of gaseous precursor-filled vesicles upon shaking can be detected by the presence of a foam on the top of the aqueous solution. This is coupled with a decrease in the volume of the aqueous solution upon the formation of foam. Preferably, the final volume of the foam is at least about two times the initial volume of the aqueous lipid solution; more preferably, the final volume of the foam is at least about three times the initial volume of the aqueous solution; even more preferably, the final volume of the foam is at least about four times the initial volume of the aqueous solution; and most preferably, all of the aqueous lipid solution is converted to foam.

The required duration of shaking time may be determined by detection of the formation of foam. For example, 10 ml of lipid solution in a 50 ml centrifuge tube may be vortexed for approximately 15–20 minutes or until the viscosity of the gaseous precursor-filled vesicles becomes sufficiently thick so that it no longer clings to the side walls as it is swirled. At this time, the foam may cause the solution containing the gaseous precursor-filled vesicles to raise to a level of 30 to 35 ml.

The concentration of stabilizing compound, especially lipid required to form a preferred foam level will vary depending upon the type of stabilizing compound such as biocompatible lipid used, and may be readily determined by one skilled in the art, once armed with the present disclosure. For example, in preferred embodiments, the concentration of 1,2-dipalimitoylphosphatidylcholine (DPPC) used to form gaseous precursor-filled vesicles according to methods contemplated by the present invention is about 20 mg/ml to about 30 mg/ml saline solution. The concentration of distearoylphosphatidylcholine (DSPC) used in preferred embodiments is about 5 mg/ml to about 10 mg/ml saline solution.

Specifically, DPPC in a concentration of 20 mg/ml to 30 mg/ml, upon shaking, yields a total suspension and entrapped gaseous precursor volume four times greater than the suspension volume alone. DSPC in a concentration of 10 mg/ml, upon shaking, yields a total volume completely devoid of any liquid suspension volume and contains entirely foam.

It will be understood by one skilled in the art, once armed with the present disclosure, that the lipids and other stabilizing compounds used as starting materials, or the vesicle final products, may be manipulated prior and subsequent to being subjected to the methods contemplated by the present invention. For example, the stabilizing compound such as a biocompatible lipid may be hydrated and then lyophilized, processed through freeze and thaw cycles, or simply hydrated. In preferred embodiments, the lipid is hydrated and then lyophilized, or hydrated, then processed through freeze and thaw cycles and then lyophilized, prior to the formation of gaseous precursor-filled vesicles.

According to the methods contemplated by the present invention, the presence of gas, such as and not limited to air, may also be provided by the local ambient atmosphere. The local ambient atmosphere may be the atmosphere within a sealed container, or in an unsealed container, may be the external environment. Alternatively, for example, a gas may be injected into or otherwise added to the container having the aqueous lipid solution or into the aqueous lipid solution itself in order to provide a gas other than air. Gases that are not heavier than air may be added to a sealed container while gases heavier than air may be added to a sealed or an unsealed container. Accordingly, the present invention includes co-entrapment of air and/or other gases along with gaseous precursors.

As already described above in the section dealing with the stabilizing compound, the preferred methods contemplated by the present invention are carried out at a temperature below the gel state to liquid crystalline state phase transition temperature of the lipid employed. By "gel state-to liquid crystalline state phase transition temperature", it is meant the temperature at which a lipid bilayer will convert from a gel state to a liquid crystalline state. See, for example, Chapman et al., *J. Biol. Chem.* 1974, 249, 2512–2521.

Hence, the stabilized vesicle precursors described above, can be used in the same manner as the other stabilized vesicles used in the present invention, once activated by application to the tissues of a host, where such factors as temperature or pH may be used to cause generation of the gas. It is preferred that this embodiment is one wherein the gaseous precursors undergo phase transitions from liquid to gaseous states at near the normal body temperature of said host, and are thereby activated by the temperature of said host tissues so as to undergo transition to the gaseous phase therein. More preferably still, this method is one wherein the host tissue is human tissue having a normal temperature of about 37° C., and wherein the gaseous precursors undergo phase transitions from liquid to gaseous states near 37° C.

All of the above embodiments involving preparations of the stabilized gas filled vesicles used in the present invention, may be sterilized by autoclave or sterile filtration if these processes are performed before either the gas instillation step or prior to temperature mediated gas conversion of the temperature sensitive gaseous precursors within the suspension. Alternatively, one or more antibactericidal agents and/or preservatives may be included in the formulation of the contrast medium, such as sodium benzoate, all quaternary ammonium salts, sodium azide, methyl paraben, propyl paraben, sorbic acid, ascorbylpalmitate, butylated hydroxyanisole, butylated hydroxytoluene, chlorobutanol, dehydroacetic acid, ethylenediamine, monothioglycerol, potassium benzoate, potassium metabisulfite, potassium sorbate, sodium bisulfite, sulfur dioxide, and organic mercurial salts. Such sterilization, which may also be achieved by other conventional means, such as by irradiation, will be necessary where the stabilized microspheres are used for imaging under invasive circumstances, e.g., intravascularly or intraperitonealy. The appropriate means of sterilization will be apparent to the artisan instructed by the present description of the stabilized gas filled vesicles and their use. The contrast medium is generally stored as an aqueous suspension but in the case of dried vesicles or dried lipidic spheres the contrast medium may be stored as a dried powder ready to be reconstituted prior to use.

The invention is further demonstrated in the following prophetic Examples 1–11. The examples, however, are not intended to in any way limit the scope of the present invention.

EXAMPLES

Example 1

Transferring is coupled to dextran and this is added to a solution of iron salts. The solution of superparamagnetic iron oxides is prepared by dissolving a mixture of ferrous and ferric iron salts in water and HCl at pH 1.0 in an anaerobic environment in the chamber of a Heat Systems Probe (Heat Systems, Farmingdale, N.Y.) sonicator equipped with an atmosphere and pressure chamber. The sonicator is activated using the standard sized horn on medium/high power and as oxygen gas is bubbled through the solution the pH is raised suddenly to pH=12. The result is iron oxide nanoparticles composed of magnetite, $Fe_3O_4$. The nanoparticles are washed in normal saline and differential centrifugation is used to harvest the nanoparticles with diameter of 20 nm and less. These nanoparticles are suspended in n-hexane at a concentration of 10 mg per ml nanoparticles with 10 mg per ml dipalmitoylphospatidylcholine. The n-hexane is evaporated and the lipid coated iron oxide nanoparticles are lyophilized. Accordingly, iron oxide nanoparticles are prepared which are coated with dextran bearing transferrin. The superparamagnetic iron oxide nanoparticles at a concentration of 10 mg per ml are mixed with 2 mg per ml perfluoropentane and 20 mg per ml pluronic F-68 with 10 mg per ml dioleoylphosphatidylcholine in sterile water with 5.5% by weight mannitol. This is microfluidized and results in a colloidal suspension of perfluoropentane coated with transferrin labeled magnetite particles. This is administered i.v. (dose=5 ml) to a 25 year old female patient with suspected ectopic pregnancy. The magnetically labeled vesicles localize in the ectopic pregnancy as the transferrin binds to the fetal tissue and this is visualized by MRI. High energy continuous wave ultrasound, 2 MHz, 2.5 Watts/cm is applied to the ectopic fetal tissue. By virtue of increased absorption if sound energy caused by the vesicles the ectopic fetal tissue is then destroyed by the ultrasound energy. This avoids an open procedure such as laparotomy or a more invasive procedure such as laparoscopy as the therapeutic ultrasound under magnetic resonance guidance can generally be performed transcutaneously without having to gain surgical access.

Example 2

A colloidal suspension of perfluorohexane (0.2 mg per ml) and perfluorpentane (0.2 mg per ml) is prepared in 10 mg per ml phospholipid (82 mole percent DPPC, 7 mole percent DPPE-PEG 5000 and 10 mole percent DPPA and 1 mole % DPPE-PEG 5000-anti fibrin antibody) with 20 mg per ml pluronic F-68 and 5.5% by weight mannitol. To this is added 5 mg per ml of iron oxide nanoparticles and this material is microfluidized as disclosed in preceding examples. This material is administered i.v. to a patient with suspected vascular thromobosis. A magnetometer superconducting quantum inferometry device (SQUID), a type of magnetic imaging, is scanned over the patient's body, localizing an apparent region of increased magnetic susceptibility to the patient's ilial veins. The presence of clot is confirmed via ultrasound imaging. High energy ultrasound, 500 milliwatts per cm$^2$ is then applied to the regions of clot to which the vesicles are bound. Sonication is performed under the guidance of the SQUID or magnetometer. The ultrasound transducer might be equipped with a SQUID as a part of the transducer. As the sonication occurs, a change in the magnetic susceptibility is detected by the magnetometer. The microvesicles cause increased absorption of sonic energy; the liquid to gaseous phase conversion of the perflourohexane in the emulsion is readily visible on either ultrasound or by magnetic imaging as the vesicles expand during the heat expansion process and this results in local lysis of the clot and noninvasive surgical alleviation of the thrombosis.

Example 3

Gas filled microvesicles impregnated with paramagnetic iron oxide particles in the microvesicle membrane are injected into the antecubital fossa. The vesicles are preferential taken up by the lymphatic vessels which could be identified on magnetic resonance with a superconducting quantum inferometry device (SQUID) as clear outlines of tumor burdened nodes. Upon identification of the nodes, a focused ultrasound transducer is then aimed at the site of the identified tumor burden and a continuous wave train of ultrasound is applied under SQUID guidance. The microvesicles are made to resonate and release energy in the form of thermal energy, thereby heating and subsequently destroying the tumor. Upon re-imaging by magnetic imaging using the SQUID device, the image of the tumor burden in the lymphatic is no longer identifiable, indicating destruction of the tumor, thereby providing a noninvasive surgical technique.

Example 4

Gas filled microvesicles prepared with manganese N,N'-Bis-(carboxy-decylamidomethyl-N-2,3-dihydroxypropyl)-ethylenediamine-N,N'-diacetate, (MN-EDTA-DDP), and Mn-EDTA-ODP, a paramagnetic complex disclosed in U.S. Pat. No. 5,312,617, the disclosure of which is incorporated herein by reference in its entirety, is injected into a patient with malignant melanoma. The exact size and location of the tumor in the lymph chain is identified on MRI and treated with real time simultaneous magnetic resonance imaging and sonication using a magnetic resonance compatible transducer operating at 1.5 Watts per cm$^2$ and a frequency of 0.75 MHz. The presence of the bubbles results in increased deposition of energy, heating of the tissue as well as local cavitation. The degree of tissue necrosis as well as the temperature of the tissue is monitored non-invasively by simultaneous real time magnetic resonance imaging on a machine equipped with echoplanar imaging gradients, thus effecting noninvasive surgery.

Example 5

In a patient with a cerebral arteriovenous malformation (AVM), a skull flap is created and the dura is surgically exposed. The patient is placed in an MRT-0.5 Tesla, interventional magnetic resonance imaging system, (GE Medical Systems, Milwaukee, Wis.). This magnetic resonance system allows access to the patient during surgical procedures while simultaneous magnetic resonance imaging. The patient is injected with 0.2 ml per kg of Aerosomes™ composed of 2 mg per ml of lipid containing 75 mole % DPPC, 8 mole % DPPA and 8 mole % DPPE-PEG 5000 with 9 mole % Platelet-Activation Factor (PAF), Avanti Polar Lipids, Alabaster Alabama entrapping a mixture of air and perfluorobutane gas. The purpose of the PAF is to activate platelets after release of the PAF from the Aerosomes™ to stimulate thrombosis of the AVM. During magnetic resonance imaging a high energy magnetic resonance compatible ultrasound transducer equipped with imaging and therapy functions is positioned over the AVM. After the Aerosomes™ are injected I.V. they pass through the large vessels and microcirculation supplying the AVM. The microbubbles are readily visualized by both magnetic resonance and ultrasound. On magnetic resonance the bubbles are portrayed as signal voids on gradient echo bright blood images obtained during transit through the AVM and on ultrasound as a snow-storm of specular reflections. The ultrasound transducer is focussed onto the AVM such that the focal zone of the ultrasound corresponds to the vascular nidus. Simultaneous magnetic resonance imaging and ultrasound are performed as the power level on ultrasound is increased (e.g. up to several watts). While emissions from cavitation obscure visualization of much of the anatomy on ultrasound, magnetic resonance still shows the surrounding tissues with exquisite detail. The surgeon operating the high energy ultrasound is therefore much better able to control the aiming, firing and energy levels of the high energy transducer and avoid damaging critical surrounding cerebral vascular structures. The procedure results in ablation of the AVM, regions of coagulative necrosis as well as thrombosis of the vascular nidus. At the end of the procedure much of the anatomy is obscured on ultrasound due to the coagulative necrosis and collections of microbubbles within the tissue, but magnetic resonance shows the entire surgical field as well as the surgical effects on the treated and surrounding tissues.

Example 6

A trauma victim with suspected hemorrhage is scanned by MRI. The scan shows a hemorrhage from the spleen. Aerosomes as in the example above except that the Aerosomes also entrap 1 mg per ml of thrombin are injected I.V. and simultaneous magnetic resonance and ultrasound imaging are performed. As the Aerosomes pass through the splenic artery the ultrasound power on the magnetic resonance compatible ultrasound transducer is increased by the surgeon to about 1.0 Watt per $cm^2$ and the Aerosomes pop releasing PAF and thrombin. Thrombosis is achieved and the hemorrhage is stopped. Simultaneous magnetic resonance angiography confirms the thrombosis of the splenic artery. This minimally invasive procedure is cheaper and caused less morbidity than conventional open surgery.

Example 7

100 ml of perfluoropentane vesicles coated with phospholipid, 82 mole % DPPC, 8 mole % DPPE-PEG 2000 and 10 mole % DPPA (mean diameter=about 1 micron) with 10 mole percent alkylated complexes of manganese (Mn-EDTA-ODP) bearing antibodies, Monoclonal Antibody to Breast Cancer (human) CA-15-3, IgG1, (SIGNET LABS, Dedham, Mass.) to human breast carcinoma is administered intravenously to a patient with breast carcinoma. The vesicles also contain 10 mole percent alkylated derivative of doxorubicin bound to the vesicle membranes. Four hours later the patient is scanned via MRI. Enhancing lymph nodes are identified in the axilla indicating metastatic disease. A magnetic resonance compatible 1 MHz ultrasound probe is positioned over the lymph nodes and high energy continuous wave ultrasound at 200 $mW/cm^2$ is applied to the lymph nodes. Simultaneous real time magnetic resonance imaging is performed on a commercially available magnet, e.g. 1.5 Tesla (GE Signa, Milwaukee, Wis.), using rapid pulse sequences, e.g. Spoiled GRASS, TR=30 msec and TE=5 msec with a 30° flip angle.

As the vesicles expand during heating they are seen as an increased region of low signal intensity on the magnetic resonance images corresponding to the zone of magnetic susceptibility caused by the vesicles. As the vesicles "pop" this is seen as a transient region of even more demonstrable hypointensity. Thereafter the vesicles disappear after they have "popped" and cleared. As the vesicles pop, the doxorubicin pro-drug is released and activated in the neoplastic lymph nodes.

Example 8

Superparamagnetic iron oxides are prepared by dissolving a mixture of ferrous and ferric iron salts in water and HCl at pH 1.0 in an anaerobic environment in the chamber of a Heat Systems Probe (Heat Systems, Farmingdale, N.Y.) sonicator equipped with an atmosphere and pressure chamber. The sonicator is activated using the standard sized horn on medium/high power and as oxygen gas is bubbled through the solution the pH is raised suddenly to pH=12. The result is iron oxide nanoparticles composed of magnetite, $Fe_3O_4$. The nanoparticles are washed in normal saline and differential centrifugation is used to harvest the nanoparticles with diameter of 20 nm and less. These nanoparticles are suspended in n-hexane at a concentration of 10 mg per ml nanoparticles with 10 mg per ml dipalmitoylphospatidylcholine. The n-hexane is evaporated and the lipid coated iron oxide nanoparticles are lyophilized. The lipid coated iron oxide nanoparticles are then added 10% by weight to 1 mg per ml of phospholipid composed of 82 mole % dipalmitoylphosphatidylcholine (DPPC) with 8 mole percent dipalmitylphosphatidylethanolamine-PEG 5,000 (DPPE-PEG 500) and 8 mole percent dipalmitoylphosphatidic acid (DPPA) with 2 mole percent palmitoylated cis-platinum derivative. This mixture of lipids, lipid coated iron oxides and palmitoylated pro-drug is suspended at a final lipid concentration of 1 mg per ml in normal saline in a sealed sterile container with a head space of perfluorobutane gas. The material is shaken for 2 minutes on a Wig-L-Bug™ at 4,200 r.p.m and results in lipid coated pro-drug bearing vesicles, the surfaces of which are studded with iron oxide nanoparticles. A dose of 20 ml of these vesicles (mean diameter=about 2 microns, bubble conc.=$1 \times 10^9$ per ml) is injected intravenously into a patient and magnetic resonance imaging is performed obtaining rapid GRASS sequences. The iron oxide labeled vesicles are easily seen on magnetic resonance as susceptibility agents causing regions of hypointensity. The pro-drug vesicle based contrast agent is shown to accumulate in regions of vascularized tumors involving the lymph nodes and other tissues. Ultrasound 1 MHz is applied as above to "pop" the vesicles under magnetic resonance guidance and achieve local drug delivery.

Example 9

Anti-myosin antibody, anti-myosin antibody, Chicken Muscle, Catalogue No. 476123, (CAL BIOCHEM, La Jolla, Calif.) is coupled to dipalmitolyphosphatidyl-ethanolamine. This is added 0.1 mg per ml to a concentration of 0.1 mg per ml perfluoropentane and 5 mg per ml of phospholipid (90 mole % DPPC with 10 mole % DPPA) in 5.5% by weight mannitol in sterile water. This mixture is bubbled with oxygen and oxygen-17 and then microemulsified using a microfluidizer (Microfluidics, Newton, Mass.) at 16,000 psi for 20 passes resulting in emulsified antibody bearing colloids of perfluoropentane. Ten cc of this material is injected into a patient with suspected myocardial infarction and magnetic resonance imaging is performed. A region of enhanced susceptibility is shown in the area of infarcted myocardium on the rapid GRASS magnetic resonance images. An magnetic resonance compatible continuous wave ultrasound transducer is positioned over the myocardium and the myocardium is treated with 0.100 watts per $cm^2$ ultrasound energy. This causes the bubbles to pop and release oxygen locally into the ischemic tissue.

Example 10

A vesicle is prepared as in Example 9, except that the cationic lipid DOTMA, N-[1(-2,3-dioleoyloxy)propyl]N,N-trimethylammonium chloride is substituted for DPPA and the DPPC is substituted with DPPE. The antibody bearing colloidal particles of perfluoropentane are then prepared as above and loaded with Oxygen-17 gas within the perfluoropentane. Then 10 micrograms per ml of DNA encoding the gene for vascular endothelial growth factor (VEGF) is added and the suspension is vortexed at low power setting for 2 minutes at 4° C. Magnetic resonance imaging is performed in a patient with suspected myocardial infarction. A region of low signal intensity is identified in the myocardium about 30 minutes after administration of the contrast agent. A magnetic resonance compatible ultrasound transducer is focused on the region of ischemic/infarcted myocardium and the perfluoropentane microbubbles are "popped" under real time simultaneous magnetic resonance imaging using a gradient echo echoplanar imaging technique in a magnetic resonance system equipped with resonating gradients, (Advanced NMR, Woburn, Mass), retrofit 1.5 Tesla, (GE Signa System, Milwaukee, Wis). This results in local integration of the gene for VEGF within the infarcted/ischemic myocardium and local gene expression. New blood vessels proliferate in response to the VEGF and there is increased growth of new blood vessels. This results in healthier regional myocardium.

Example 11

Cationic vesicles are prepared by shaking a mixture of lipid 82 mole % DPPC with 7 mole % DPPE-PEG 5,000 with 5 mole % DPPA and 6 mole % DOTMA with a head space of gas prepared from a mixture of perfluorobutane and oxygen- 16. After shaking, as disclosed in preceding examples with the Wig-L-Bug™, 100 micrograms per ml of DNA for the VEGF gene is added and the mixture is gently vortexed for 1 minute. This results in absorption of the DNA onto the surface of the microvesicles. A somewhat higher amount of vesicles is necessary for visualization under magnetic resonance than the magnetically labeled vesicles but the vesicles are still detectable on T2 weighted spin echo or fast spin echo or gradient echo pulse sequences. Magnetic resonance angiography (MRA), a type of magnetic resonance imaging, using a 2D Time of Flight pulse sequence is performed an a diabetic patient with peripheral vascular disease involving the lower extremities. A significant stenosis is shown in the popliteal artery. The microvesicles bearing DNA are administered i.v. and on the basis of the vesicle signals from MRI and ultrasound, high energy ultrasound is applied under magnetic resonance imaging guidance from the skin surface to focus energy on the region of stenosis in the popliteal artery. This results in localized bubble rupture and gene release at the site of arterial stenosis. Localized expression of VEGF encourages collateral and new vessel formation improving blood flow to the distal leg.

The disclosures of each patent, patent application and publication cited or described in this document are hereby incorporated herein by reference, in their entirety.

Various modification of the invention, in addition to those described herein, will be apparent to those skilled in the art from the foregoing description. Such modifications are also intended to fall within the scope of the appended claims.

What is claimed is:

1. A method for the controlled delivery of therapeutic compounds to a region of a patient using magnetic resonance focused therapeutic ultrasound comprising:

administering a contrast medium for magnetic resonance imaging comprising gas filled vesicles which comprise a therapeutic compound to a patient;

scanning said patient with magnetic resonance imaging using said contrast medium to determine the presence of the vesicles in the region; and applying ultrasound to said region to rupture said vesicles to release the therapeutic compound in the region.

2. A method of claim 1 wherein said application of ultrasound is simultaneous with a second scanning step whereby said patient is scanned with magnetic resonance imaging.

3. A method of claim 1 wherein said application of ultrasound is followed by a second scanning step whereby said patient is scanned with magnetic resonance imaging.

4. A method of claim 1 wherein said region of a patient is selected from the group consisting of: cardiovascular region; gastrointestinal region; intranasal tract; auditory canal; intraocular region; intraperitoneal region; kidneys; urethra; genitourinary tract, brain, spine, pulmonary region, and soft tissues.

5. A method of claim 1 wherein said gas-filled vesicles comprise a targeting agent.

6. A method of claim 1 wherein said therapeutic compound is selected from the group consisting of an oligonucleotide sequence, an antisense sequence, an antibody, and a chemotherapeutic agent.

7. A method of claim 1 wherein said gas filled vesicles are administered intravenously.

8. A method of claim 1 wherein said gas is selected from the group consisting of air, nitrogen, carbon dioxide, oxygen, fluorine, helium, argon, xenon, neon, and combinations thereof.

9. A method of claim 1 wherein said gas comprises a fluorinated gas.

10. A method of claim 9 wherein the fluorinated gas comprises a perfluorocarbon or sulfur hexafluoride.

11. A method of claim 10 wherein the perfluorocarbon gas is selected from the group consisting of perfluoropropane, perfluorobutane, perfluorocyclobutane, perfluoromethane, perfluoroethane, perfluorohexane, and perfluoropentane.

12. A method of claim 1 wherein said gas comprises $^{17}O$.

13. A method of claim 1 wherein said contrast medium further comprises a paramagnetic agent or a superparamagnetic agent.

14. A method of claim 13 wherein the contrast medium comprises a paramagnetic agent.

15. A method of claim 14 wherein the paramagnetic agent comprises a paramagnetic ion selected from the group consisting of transition, lanthanide and actinide elements.

16. A method of claim 15 wherein the paramagnetic ion is selected from the group consisting of Gd(III), Mn(II), Cu(II), Cr(III), Fe(II), Fe(III), Co(II), Er(II), Ni(II), Eu(III) and Dy(III).

17. A method of claim 16 wherein the paramagnetic ion is Mn(II).

18. A method of claim 14 wherein the paramagnetic agent comprises a nitroxide.

19. A method of claim 13 wherein the contrast medium comprises a superparamagnetic agent.

20. A method of claim 19 wherein the superparamagnetic agent comprises a metal oxide or metal sulfide.

21. A method of claim 20 wherein the superparamagnetic agent comprises a metal oxide wherein the metal is iron.

22. A method of claim 20 wherein the superparamagnetic agent is selected from the group consisting of ferritin, iron, magnetic iron oxide, $\gamma$-$Fe_2O_3$, manganese ferrite, cobalt ferrite and nickel ferrite.

23. A method of claim 1 wherein said gas filled vesicles comprise $^{19}F$ and said magnetic resonance imaging is nuclear magnetic resonance.

24. A method of claim 1 wherein said gas filled vesicles are administered interstitially.

25. A method of claim 1 wherein said gas is selected from the group consisting of hyperpolarized xenon, hyperpolarized argon, hyperpolarized helium, and hyperpolarized neon.

26. A method of claim 1 wherein said vesicles comprise liposomes.

27. A method of claim 26 wherein said liposomes comprise crosslinked or polymerized liposomes.

28. A method of claim 26 wherein said liposomes comprise polymerized lipids.

29. A method of claim 26 wherein said liposomes further comprise polyethylene glycol.

30. A method of claim 1 wherein said vesicles comprise a monolayer.

31. A method of claim 30, wherein said monolayer comprises a phospholipid.

32. A method of claim 31, wherein said gas comprises perfluoropropane, perfluorobutane, perfluoropentane, perfluorohexane, or sulfur hexafluoride.

33. A method of claim 31, wherein said monolayer comprises a phospholipid and said gas comprises perfluoropentane.

34. A method of claim 31, wherein said monolayer comprises a phospholipid and said gas comprises sulfur hexafluoride.

35. A method of claim 31, wherein said monolayer comprises a phospholipid and said gas comprises perfluoropropane.

36. A method of claim 1, wherein said vesicles comprise a polymer.

37. A method of claim 36, wherein said polymer comprises an acrylate.

38. A method of claim 37, wherein said gas comprises air.

39. A method of claim 36, wherein said polymer comprises a methacrylate.

40. A method of claim 39, wherein said gas comprises air.

41. A method of claim 36, wherein said polymer comprises a cyanoacrylate.

42. A method of claim 41 wherein said gas comprises air.

43. A method of claim 1, wherein said vesicles comprise a polysaccharide.

44. A method of claim 43, wherein said polysaccharide comprises galactose.

45. A method of claim 44, wherein said gas is nitrogen.

46. A method of claim 1, wherein said vesicles comprise a surfactant.

47. A method of claim 46, wherein said gas comprises perfluoropropane, perfluorobutane, perfluoropentane, perfluorohexane, sulfur hexafluoride, nitrogen, or mixtures thereof.

48. A method of claim 47, wherein said gas comprises a mixture of perfluoropropane and nitrogen.

49. A method of claim 48, wherein said gas comprises a mixture of perfluorohexane and nitrogen.

50. A method of claim 46, wherein said vesicles have been rehydrated from lyophilized vesicles.

51. A method of claim 1, wherein said therapeutic compound comprises a bioactive agent.

* * * * *